United States Patent [19]

Martel et al.

[11] 4,356,187

[45] Oct. 26, 1982

[54] NOVEL ESTERS OF 2-METHYL-3-ALLYL-4-SUBSTITUTED-CYCLOPENT-2-ENE-1-YL

[75] Inventors: Jacques Martel, Bondy; Jean Tessier, Vincennes; Andre Teche, Nanterre, all of France

[73] Assignee: Roussel Uclaf, Paris, France

[21] Appl. No.: 141,201

[22] Filed: Apr. 17, 1980

[30] Foreign Application Priority Data

Apr. 26, 1979 [FR] France .................. 79 10651

[51] Int. Cl.³ .................. C07C 121/48; C07C 121/66; C07C 69/743; A01N 37/08
[52] U.S. Cl. .................. 424/304; 260/464; 260/465 D; 560/17; 542/429; 560/53; 560/61; 560/62; 560/106; 560/107; 560/118; 560/124; 424/306; 424/308; 424/275; 424/279; 424/305
[58] Field of Search .................. 260/464, 465 D; 560/105, 118, 124, 17, 53, 61, 62, 106, 107; 542/429; 424/304, 305, 308, 275, 279, 306

[56] References Cited

U.S. PATENT DOCUMENTS

| | | | |
|---|---|---|---|
| 2,717,262 | 9/1955 | Cole .................. | 560/124 |
| 2,768,965 | 10/1956 | Stansbury, Jr., et al. .......... | 560/124 |
| 2,815,362 | 12/1957 | Harper .................. | 260/464 |
| 3,009,946 | 11/1961 | Takei et al. .................. | 560/124 |
| 3,636,059 | 1/1972 | Matsui et al. .................. | 560/124 X |
| 3,678,172 | 7/1972 | Hill et al. .................. | 560/124 X |
| 3,679,667 | 7/1972 | Fanta .................. | 542/429 X |
| 3,823,177 | 7/1974 | Fanta et al. .................. | 560/118 |
| 3,876,681 | 4/1975 | Okuno et al. .................. | 560/124 |
| 4,281,170 | 7/1981 | Szekely et al. .................. | 560/124 |

FOREIGN PATENT DOCUMENTS 874392 1/1979 Belgium .

Primary Examiner—Joseph Paul Brust
Attorney, Agent, or Firm—Hammond & Littell, Weissenberger and Muserlian

[57] ABSTRACT

Novel esters of the formula

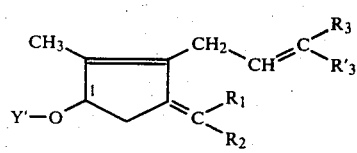

wherein $R_1$ and $R_2$ are individually selected from the group consisting of carbamoyl and $R_1'$ and $R_2'$, $R_1'$ and $R_2'$ are individually selected from the group consisting of hydrogen, halogen, alkyl of 1 to 6 carbon atoms, aryl of 6 to 10 carbon atoms, aralkyl of 7 to 13 carbon atoms, alkoxycarbonyl of 2 to 5 carbon atoms and —CN, $R_3$ and $R_3'$ are individually selected from the group consisting of hydrogen, halogen, alkenyl of 2 to 3 carbon atoms and alkyl of 1 to 3 carbon atoms, $Y'$ is selected from the group consisting of

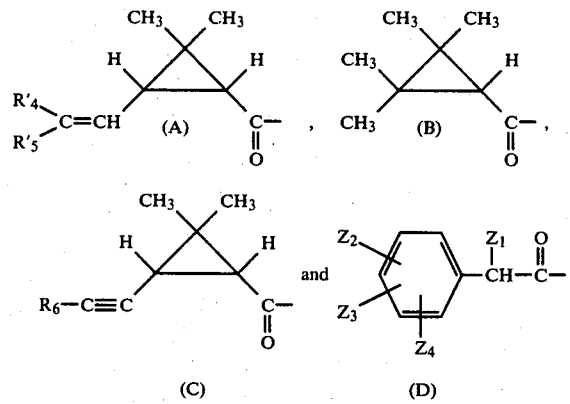

$R_4'$ and $R_5'$ are individually selected from the group consisting of hydrogen, alkyl of 1 to 4 carbon atoms, fluorine, bromine, chlorine and $R_4'$ and $R_5'$ together with the carbon atom to which they are attached form an optionally unsaturated hydrocarbon ring or heterocycle of 3 to 7 chain members and a heterocycle of the formula

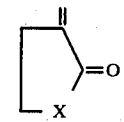

X is selected from the group consisting of sulfur and oxygen or $R_4'$ is cyano and $R_5'$ is phenyl or $R_4'$ is hydrogen and $R_5'$ is selected from the group consisting of cyano,

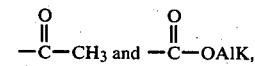

AlK is alkyl of 1 to 4 carbon atoms, the double bond in the 1- position of the vinyl side chain of formula (A) having (E) or (Z) configuration, $R_6$ is selected from the group consisting of hydrogen, alkyl of 1 to 4 carbon atoms and alkoxycarbonyl of 2 to 5 carbon atoms, the substituents on the cyclopropane ring of formula (A) and (C) have the cis or trans, racemic or optically active configuration, $Z_1$ is alkyl of 1 to 4 carbon atoms, $Z_2$, $Z_3$ and $Z_4$ are individually selected from the group consisting of hydrogen, alkyl of 1 to 4 carbon atoms, alkoxy of 1 to 4 carbon atoms, alkylthio of 1 to 4 carbon atoms and halogen and the asymetric carbon of formula (D) may be (S) or (R) configuration or a racemic mixture thereof and the carbon atom in the 1-position of the alcohol moiety may have (R), (S) or racemic configuration having insecticidal properties and their preparations.

28 Claims, No Drawings

12341234
NOVEL ESTERS OF 2-METHYL-3-ALLYL-4-SUBSTITUTED-CYCLOPENT-2-ENE-1-YL

STATE OF THE ART

Belgium Pat. No. 874,392 relates to insecticidal compositions.

OBJECTS OF THE INVENTION

It is an object of the invention to provide the novel esters of formula I' and a novel process for their preparation.

It is another object of the invention to provide novel insecticidal compositions and to a novel method of killing insects.

These and other objects and advantages of the invention will become obvious from the following detailed description.

THE INVENTION

The novel esters of the invention have the formula

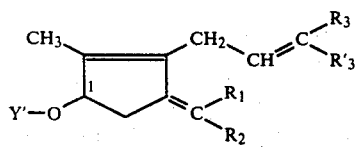

wherein $R_1$ and $R_2$ are individually selected from the group consisting of carbamoyl and $R_1'$ and $R_2'$, $R_1'$ and $R_2'$ are individually selected from the group consisting of hydrogen, halogen, alkyl of 1 to 6 carbon atoms, aryl of 6 to 10 carbon atoms, aralkyl of 7 to 13 carbon atoms, alkoxy-carbonyl of 2 to 5 carbon atoms and —CN, $R_3$ and $R_3'$ are individually selected from the group consisting of hydrogen, halogen, alkenyl of 2 to 3 carbon atoms and alkyl of 1 to 3 carbon atoms, Y' is selected from the group consisting of

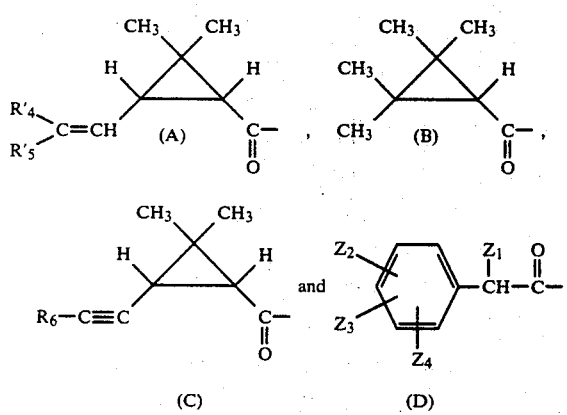

$R_4'$ and $R_5'$ are individually selected from the group consisting of hydrogen, alkyl of 1 to 4 carbon atoms, fluorine, bromine, chlorine and $R_4'$ and $R_5'$ together with the carbon atom to which they are attached form an optionally unsaturated hydrocarbon ring or heterocycle of 3 to 7 chain members and a heterocycle of the formula

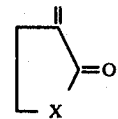

X is selected from the group consisting of sulfur and oxygen or $R_4'$ is cyano and $R_5'$ is phenyl or $R_4'$ is hydrogen and $R_5'$ is selected from the group consisting of cyano,

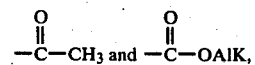

Alk is alkyl of 1 to 4 carbon atoms, the double bond in the 1-position of the vinyl side chain of formula (A) having (E) or (Z) configuration, $R_6$ is selected from the group consisting of hydrogen, alkyl of 1 to 4 carbon atoms and alkoxycarbonyl of 2 to 5 carbon atoms, the substituents on the cyclopropane ring of formulae (A) and (C) have the cis or trans, racemic or optically active configuration, $Z_1$ is alkyl of 1 to 4 carbon atoms, $Z_2$, $Z_3$ and $Z_4$ are individually selected from the group consisting of hydrogen, alkyl of 1 to 4 carbon atoms, alkoxy of 1 to 4 carbon atoms, alkylthio of 1 to 4 carbon atoms and halogen and the asymetric carbon of formula (D) may be (S) or (R) configuration or a racemic mixture thereof and the carbon atom in the 1-position of the alcohol moiety may have (R), (S) or racemic configuration.

Preferred esters of the invention have the formula

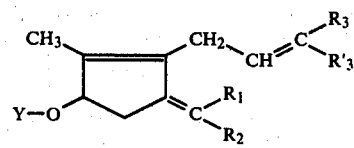

wherein $R_1$, $R_2$, $R_3$ and $R_3'$ have the above definition and Y is selected from the group consisting of

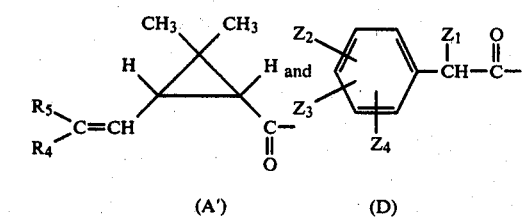

wherein $Z_1$, $Z_2$, $Z_3$ and $Z_4$ have the above definitions, $R_4$ and $R_5$ are individually selected from the group consisting of hydrogen, alkyl of 1 to 4 carbon atoms, fluorine, chlorine and bromine or $R_4$ is hydrogen and $R_5$ is selected from the group consisting of

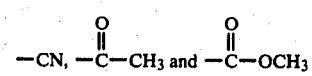

or $R_4$ and $R_5$ together with the carbon atom to which they are attached form an optionally unsaturated hydrocarbon or heterocyclic ring of 3 to 7 ring members and

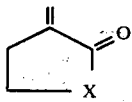

and X has the above definition and the substituent of A' on the cyclopropane ring gives a cis or trans or racemic or optically active configuration, the double bond in the 1-position of the side chain may have (E) or (Z) configuration and the alcohol moiety may have the (R) or (S) or racemic configuration.

Among the more preferred compounds of formula I are those wherein Y has the formula

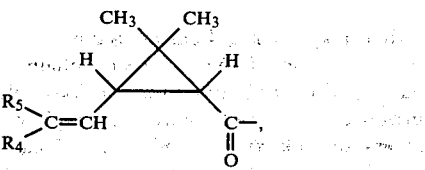

those wherein Y has the formula

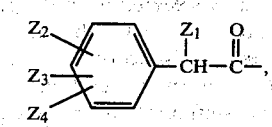

those wherein Y is group A' and $R_1$ and $R_2$ are halogen and $R_3$ and $R_3'$ are hydrogen and $R_4$ and $R_5$ are halogen, those of formula I wherein Y is group A', $R_1$, $R_2$, $R_3$ and $R_3'$ are hydrogen and $R_4$ and $R_5$ together with the carbon atoms to which they are attached form a hydrocarbon ring and those of formula I wherein Y is group A', $R_1$, $R_2$, $R_3$ and $R_3'$ are hydrogen and $R_4$ and $R_5$ are halogen.

Specific preferred compounds of formula I are (1S) 2-methyl-3-allyl-4-methylene-cyclopent-2-ene-1-yl (1R, trans) 2,2-dimethyl-3-cyclopentylidenemethyl-cyclopropane-1-carboxylate, (1S) 2-methyl-3-allyl-4-methylene-cyclopent-2-en-1-yl (1R, trans) 2,2-dimethyl-3-(2,2-difluoroethenyl)-cyclopropane-1-carboxylate, (1S) 2-methyl-3-allyl-4-methylene-cyclopent-2-ene-1-yl (1R, trans) 2,2-dimethyl-3-(2,2-dichloroethenyl)cyclopropane-1-carboxylate, (1S) 2-methyl-3-allyl-4-methylenecyclopent-2-ene-1-yl (1R, trans) 2,2-dimethyl-3-[2-(Z)-cyanoethenyl]-cyclopropane-1-carboxylate, (1S) 2-methyl-3-allyl-4-methylene-cyclopent-2-ene-1-yl (1R, trans) 2,2-dimethyl-3-(2-chloro-2-fluoro-ethenyl)-cyclopropane-1-carboxylate, (1S) 2-methyl-3-allyl-4-methylene-cyclopent-2-ene-1-yl (1R, trans) 2,2-dimethyl-3-cyclobutylidenemethyl-cyclopropane-1-carboxylate and (1S) 2-methyl-3-allyl-4-methyene-cyclopent-2-ene-1-yl (1R, cis) 2,2-dimethyl-3-ethynyl-cyclopropane-1-carboxylate.

Examples of $R_1$ and $R_2$ are hydrogen, fluorine, bromine, chlorine, methyl, ethyl, propyl, isopropyl, straight or branched butyl, pentyl or hexyl, alkoxycarbonyl such as methoxycarbonyl, ethoxycarbonyl, propoxycarbonyl, isopropoxycarbonyl, branched or linear butoxycarbonyl, carbamoyl, phenyl, naphthayl or cyano; of $R_3$ and $R_3'$ are hydrogen, methyl, ethyl, propyl, isopropyl, vinyl, propen-1-yl and allyl; of $R_4'$ and $R_5'$ are hydrogen, methyl, ethyl, propyl, isopropyl, fluorine, chlorine or bromine or $R_4'$ and $R_5'$ together with the carbon atom to which they are attached form cyclopropyl, cyclobutyl, cyclopentyl, cycylohexyl or cycloheptyl or an optionally unsaturated heterocycle of 3 to 7 ring atoms, especially of the structure

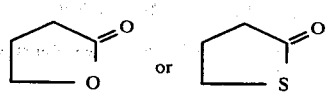

of $Z_1$ are methyl, ethyl, propyl, isopropyl or branched or linear butyl and of $Z_2$, $Z_3$ and $Z_4$ are hydrogen, methyl, ethyl, propyl, isopropyl, branched or linear butyl, alkoxy such as methoxy, ethoxy, propoxy, isopropoxy, branched or linear butoxy, alkylthio such as methylthio, ethylthio, propylthio, isopropylthio or branched or linear butylthio, fluorine, chlorine, bromine or iodine.

The novel process of this invention for the preparation of formula I comprises reacting an (R), (S) or racemate of formula II

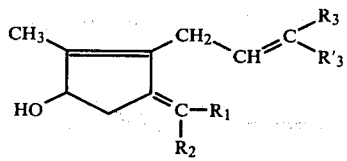

wherein $R_1$, $R_2$, $R_3$ and $R_3'$ have the above definitions or a functional derivative thereof with a carboxylic acid of the formula Y'—OH III or a functional derivative thereof such as an acid halide, acid anhydride, mixed anhydride or a salt thereof of an organic or inorganic base.

Preferably, the functional derivative of formula II is a metallic salt such as an alkali metal said or silver salt or a salt of an organic base. The acid derivative is preferably an acid chloride and the esterification is effected in benzene in the presence of pyridine.

A process for the preparation of a compound of formula I' comprises reacting a compound of the formula

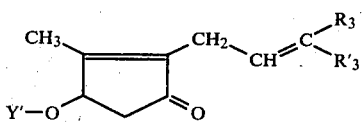

wherein $R_3$, $R_3'$ and Y' have the above definitions with a reactant of the formula

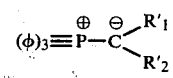

wherein $R_1'$ and $R_2'$ have the above definitions and then when $R_1'$ and/or $R_2'$ are alkoxycarbonyl which are the corresponding compounds of formula I' containing one or 2 ester groups with ammonia to obtain the corresponding compound of formula I' containing one or 2 carbamoyl groups.

The compounds of formula V may be obtained by reacting a substituted triphenyl phosphonium halide with a strong base in a solvent or when $R_1'$ or $R_2'$ is halogen, reacting a triphenyl phosphine and a haloform with a strong base in an organic solvent.

A suitable mode of the process comprises reacting a substituted triphenyl phosphonium chloride as the phosphonium salt with butyllithium as the strong base with ether as the solvent.

Examples of suitable strong bases are alkali metal hydrides, alkali metal amides, alkali metal alcoholates and alkyllithiums and the solvent may be ether, dimethylsulfoxide, tetrahydrofuran, dimethoxyethane, alkanols, monomethyl ether of diethyleneglycol and diethyl ether of diethylene glycol.

Esters of allethrolone and cyclopropane carboxylic acids such as dl allethrolone d-trans chrysanthemate or bioallethrine are known to possess insecticidal properties. The said known compounds have an interesting knockdown activity but have a relatively weak lethal activity.

In contrast to the known esters, the esters of formula I' are an especially interesting class possessing particularly interesting insecticidal, acaricidal, ixodicidal and nematocidal activity having both an elevated knockdown and lethal activities so that the compounds are particularly superior to the known compounds.

The novel preferred insecticidal composition are comprised of an insectically effective amount of at least one compound of formula I', an optionally present synergistic agent and an inert carrier. The compositions may also contain other pesticidal agents. The compositions may be in the form of powders, granules, suspensions, emulsions, solutions, aerosol solutions, combustible strips, baits and other classical preparations used for the genre of the compounds. Especially preferred are compounds of formula I. Preferably, the compositions contain 0.005% to 10% by weight of the active material.

Examples of suitable compounds are (1S) 2-methyl-3-allyl-4-methylene-cyclopent-2-ene-1-yl (1R, trans) 2,2-dimethyl-3-cyclopentylidenemethyl-cyclopropane-1-carboxylate, (1S) 2-methyl-3-allyl-4-methylene-cyclopent-2-ene-1-yl (1R, trans) 2,2-dimethyl-3-(2,2-difluoroethenyl)-cyclopropane-1-carboxylate, (1S) 2-methyl-3-allyl-4-methylene-cyclopent-2-ene-1-yl (1R, trans) 2,2-dimethyl-3-(2,2-dichloroethenyl)-cyclopropane-1-carboxylate, (1S) 2-methyl-3-allyl-4-methylene-cyclopent-2-ene-1-yl (1R, trans) 2,2-dimethyl-3-[2-(Z)-cyanoethenyl]-cyclopropane-1-carboxylate, (1S) 2-methyl-3-allyl-4-methylene-cyclopent-2-ene-1-yl (1R, trans) 2,2-dimethyl-3-(2-chloro-2-fluoro-ethenyl)-cyclopropane-1-carboxylate, (1S) 2-methyl-3-allyl-4-methylene-cyclopent-2-ene-1-yl (1R, trans) 2,2-dimethyl-3-cyclobutylidenemethyl-cyclopropane-1-carboxylate and (1S) 2-methyl-3-allyl-4-methylene-cyclopent-2-ene-1-yl (1R, cis) 2,2-dimethyl-3-ethynyl-cyclopropane-1-carboxylate.

The compositions are useful as insecticides against houseflies and mosquitoes with an elevated knockdown and lethal activity. The compositions are equally useful against Spodoptera Littoralis, Epilachna Varivestris, Sitophilus Granarius, Tribolium Castaneum, Blatella Germanica and Aphis Fabae.

The compositions may contain a vehicle and/or a non-ionic surface active agent to ensure a uniform dispersion of the components of the mixture. The vehicle may be a liquid such as water, alcohol, hydrocarbons or other organic solvents, animal, vegetable or mineral oil or a powder such as talc, clays, silicates, Kieselguhr or a combustible solid such as tabu powder or pyrethrum stalks.

The optional synergistic agents may be those classially used for pyrethrinoids such as 1-(2,5,8-trioxadodecyl-2-propyl-4,5-methylenedioxy-benzene or piperonyl butoxide, N-(2-ethylheptyl)-bicyclo-[2,2,1]-5-heptene-2,3-dicarboximide and piperonyl-bis-2-(2'-n-butoxyethoxy)-ethylacetal or tropical.

The novel method of the invention for killing insects comprises contacting insects with an insecticidally effective amount of at least one compound of formula I'

The novel acaricidal compositions of the invention are comprised of an acaricidally effective amount of at least one compound of formula I' and an inert carrier. The compositions may also contain one or more than pesticides and/or a synergist. The compositions may be in the form of powders, granules, suspensions, emulsions or solutions. When in the form of wettable powders for foliar spraying, the compositions preferably contain 1 to 80% by weight of the active ingredient and when in the form of liquids for foliar spraying, the compositions preferably contain 1 to 500 g/liter of the active material. When in the form of a powder for foliar dusting, the compositions preferably contain 0.05 to 10% by weight of the active ingredient.

Tests have shown that the acaricidal compositions are effective against Tetranyclus Urticae and have a double action, namely the classical lethal activity as well as an repulsive activity which is particularly interesting from an ecological angle.

The novel method of the invention of protecting plants against parasitic acariens comprises applying to plants sufficient amounts of at least one compound of formula I' to kill and/or repulse acariens. The usual effective amount is 1 to 100 g of active compound per hectare.

The novel nematocidal compositions of the invention are comprised of a nematocidally effective amount of at least one compound of formula I' and an inert carrier. The compositions are preferably in the form of liquids for treatment of the soil containing 300 to 500 g per liter of the active material. Tests have shown the compositions to be effective against Panagrellus Silusiae.

The novel method of the invention of combatting nematodes comprises applying to the soil a nematocidally effective amount of at least one compound of formula I'. The usual effective amount is 1 to 100 g of active material per hectare.

The novel antifungel compositions of the invention are comprised of an antifungally effective amount of at least one compound of formula I' and an inert carrier. The compositions are preferably in the form of powders for foliar spraying containing 25 to 95% by weight of the active ingredient or powders for foliar dusting containing 2.5 to 99% by weight of the active ingredient. Tests have shown the compounds to be effective against Aerobacter Aerogenes, Pseudomonas Aeruginosa, Botrytis Cinerea and Fusarium Rosenum.

The novel method of the invention for combatting fungi comprises contacting fungi with a fungicidally effective amount of at least one compound of formula I'. Preferably the active material is applied to plants to be protected.

The veterinary compositions of the invention for combatting animal parasitic acariens comprises an acaricidally effective amount of at least one compound of formula I' and a veterinary carrier. The compositions may be in a suitable form for external application or in a form for parenteral or digestive administration. The compositions may also contain the usual pyrethrinoid synergists.

The compositions have been shown to be effective against Rhipicephalus Sanguinems in dogs and are useful against all types of mange such as sarcoptic mange, psoroptic mange and chorioptic mange as well as against all types of ticks such as Boophilus species, Hyalomnia species, Amblyoma species and Rhipicephalus species.

The novel method of the invention of protecting animals against acariens comprises administering to warm-blooded animals an acaricidally effective amount of at least one compound of formula I'. The compounds may be applied topically, parenterally or orally.

A preferred mode of the invention is to incorporate the active material of formula I' into the animal feeds. For example, the animal feed may contain 0.01 to 2% by weight of (1S) 2-methyl-3-allyl-4-methylene-cyclopent-2-ene-1-yl 2,2-dimethyl-3S-(2,2-difluoroethenyl)-cyclopropane-1R-carboxylate.

Preferred pesticidal compositions of the invention comprise a mixture of (A) a pesticidally effective amount of at least one compound of formula I' and (B) at least one pyrethrinoid ester selected from the group consisting of esters of allethrolones, 3,4,5,6-tetrahydrophthalimido-methyl alcohol, 5-benzyl-3-furyl methanol, 3-phenoxy-benzyl alcohol and α-cyano-3-phenoxy-benzyl alcohols with chrysanthemic acids, esters of 5-benzyl-3-furyl methanol and 2,2-dimethyl-3-(2-oxo-3-tetrahydrothiophenylidenemethyl)-cyclopropane-1-carboxylic acids, esters of 3-phenoxy-benzyl alcohol or α-cyano-3-phenoxy-benzyl alcohols and 2,2-dimethyl-3-(2,2-dichlorovinyl)-cyclopropane-1-carboxylic acids, esters of α-cyano-3-phenoxy-benzyl alcohols and 2,2-dimethyl-3-(2,2-dibromovinyl)-cyclopropane-1-carboxylic acids, esters of 3-phenoxy-benzyl alcohol and 2-(p-chlorophenyl)-2-isopropyl-acetic acids and esters of allethrolones, 3,4,5,6-tetrahydrophthalimidomethanol, 5-benzyl-3-furyl-methanol, 3-phenoxy-benzyl alcohol and α-cyano-3-phenoxy-benzyl alcohols and 2,2-dimethyl-3-(1,2,2,2-tetrahalo)-cyclopropane-1-carboxylic acids wherein the halogens may be fluorine, chlorine or bromine, where both the compounds of formula I' and the pyrethrinoid esters may exist in their various possible stereoisomeric forms.

The mixed compositions of the invention are especially interesting since they permit a variety of activity against more than one pesticide and/or have a synergistic effect. The weight ratio of A to B is preferably 250 to 100.

The starting compounds of formula II are described in commonly assigned U.S. patent application Ser. No. 141,200, now U.S. Pat. No. 4,304,733, filed on even date herewith by reacting a compound of the formula

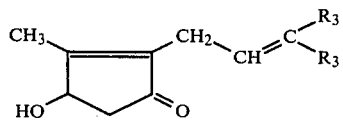

V with a compound of the formula

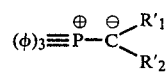

wherein $R_1'$, $R_2'$, $R_3$ and $R_3'$ have the above definition after protecting the hydroxyl group in the form of an ester with boric acid or an alkanoic acid of 2 to 4 carbon atoms or an ether. The compounds of formula II wherein $R_1$ and/or $R_2$ are carbamoyl can be prepared by reacting a compound of formula II with the hydroxy group blocked and wherein $R_1'$ and/or $R_2'$ is alkoxycarbonyl with ammonium hydroxide and the hydroxy group is then deblocked.

The compounds of formulae III and IV are generally known and may be prepared by processes described in the literature. The functional derivatives of formula III may be prepared by procedures known to those skilled in the art. Esterification of carboxylic acids with allethrolone or derivatives of allethrolone substituted on the allyl chain are known.

In the following examples there are described several preferred embodiments to illustrate the invention. However, it should be understood that the invention is not intended to be limited to the specific embodiments.

EXAMPLE 1

(1S) 2-methyl-3-allyl-4-methylene-cyclopent-2-ene-1-yl (1R, cis) 2,2-dimethyl-3-(2-methyl-1-propenyl)-cyclopropane-1-carboxylate

STEP A:

1S-hydroxy-2-methyl-3-allyl-4-methylene-cyclopent-2-ene 31.4 g of potassium tert-butylate were added in 4 portions over 10 minutes to a stirred mixture of 250 ml of ether, 26.4 ml of tert.-butanol and 100 g of triphenylmethylphosphonium bromide under an inert atmosphere and the reaction mixture was allowed to stand at room temperature for 5 hours. The mixture was cooled to 0° to 5° C. and a solution of 31.9 g of 1-S-hydroxy-2-methyl-3-allyl-4-oxo-cyclopent-2-ene in 30 ml of ether was added thereto over 20 minutes. The mixture was held at 0° to 5° C. for 2 hours and the temperature was raised to room temperature for 17 hours and the mixture was then poured into an aqueous saturated monosodium phosphate solution. The decanted aqueous phase was extracted with ether and the combined organic phases were dried over magnesium sulfate and evaporated to dryness. The residue was taken up in ether and the mixture was stirred a few minutes and was then filtered. The filtrate was evaporated to dryness under reduced pressure and the residue was chromatographed over silica gel. Elution with a 6-4 cyclohexane-ethyl acetate containing 2°/₀₀ of triethylamine yielded 26.05 g of 1S-hydroxy-2-methyl-3-allyl-4-methylene-cyclopent-2-ene. After crystallization from petroleum ether (B.p.=40°-70° C.), the product melted at 23° C. and had a specific rotation of $[\alpha]_D^{20} = -110° \pm 2°$ (c=0.8% in chloroform).

IR Spectrum (CHCl₃): Absorption at 3586 cm⁻¹ (OH); at 865 cm⁻¹ (=CH₂); at 1637 cm⁻¹ (>C=C); at 916 cm⁻¹ (—CH=CH₂).

STEP B: (1S) 2-methyl-3-allyl-4-methylene-cyclopent-2-ene-1-yl (1R, cis) 2,2-dimethyl-3-(2-methyl-1-propenyl)-cyclopropane-1-carboxylate A solution of 5 g of the product of Step A in 10 ml of benzene was added over 30 minutes at room temperature to a mixture of 6.5 g (1R, cis) 2,2-dimethyl-3-(2-methyl-1-propenyl)-cyclopropane-1-carboxylic acid chloride, 20 ml of benzene and 4 ml of pyridine and the mixture was stirred at 20° C. for 20 hours. The mixture was poured into water and the decanted aqueous phase was extracted with benzene. The combined benzene phases were washed with water, dried over magnesium sulfate and were filtered. The filtrate was evaporated to dryness under reduced pressure and the residue was chromatographed over silica gel. Elution with a 9-1 cyclohexane-ethyl acetate mixture containing 1‰ of triethylamine yielded 9.41 g of (1S) 2-methyl-3-allyl-4-methylene-cyclopent-2-ene-1-yl (1R, cis) 2,2-dimethyl-3-(2-methyl-1-propenyl)-cyclopropane-1-carboxylate with a specific rotation of $[\alpha]_D^{20} = -32° \pm 1°$ (c=1.3% in ethanol).

Analysis: $C_{20}H_{28}O_2$: Calculated: %C 79.95 %H 9.39, Found: 79.8 9.5.

IR Spectrum (chloroform): Absorption at 1720 cm$^{-1}$ (carbonyl of ester); at 1639 cm$^{-1}$ (C=C); at 993–916 cm$^{-1}$ (—C=CH$_2$); at 864 cm$^{-1}$ (=CH$_2$).

EXAMPLE 2

(1S) 2-methyl-3-allyl-4-methylene-cyclopent-2-ene-1-yl
(1R, trans)
2,2-dimethyl-3-(2-methyl-1-propenyl)-cyclopropane-1-carboxylate 50 ml of 1.4 N butyllithium were added over 20 minutes at room temperature to a suspension of 26 g of triphenylmethylphosphonium bromide in 150 ml of ether under an inert atmosphere and the mixture was stirred for 30 minutes and was then cooled to 5° C. A solution of 10.9 g of (1S) 2-methyl-3-allyl-4-oxo-cyclopent-2-ene-1-yl (1R, trans) 2,2-dimethyl-3-(2-methyl-1-propenyl)-cyclopropane-1-carboxylate in 60 ml of ether were added to the mixture over 25 minutes and after standing at 5° C. for 30 minutes, the mixture was poured into an iced aqueous monosodium phosphate solution. The aqueous phase was extracted with ether and the combined organic phases were washed with water until the wash water was neutral, dried over magnesium sulfate and evaporated to dryness under reduced pressure. The residue was chromatographed over silica gel and was eluted with a 9-1 cyclohexane-ethyl acetate mixture containing 1‰ triethylamine to obtain 1.03 g of (1S) 2-methyl-3-allyl-4-methylene-cyclopent-2-ene-1-yl (1R, trans) 2,2-dimethyl-3-(2-methyl-1-propenyl)-cyclopropane-1-carboxylate.

IR Spectrum (chloroform): Absorption at 1715 cm$^{-1}$ (carbonyl of ester); at 1639 cm$^{-1}$ (C=C); at 867 cm$^{-1}$ (>C=CH$_2$).

NMR Spectrum (CDCl$_3$-60 MHz): Peaks at 1.20 ppm (doublet J=7.5 Hz) (hydrogens of 2-CH$_3$ of cyclopropane); at 1.7 ppm (hydrogens of methyls in chain of 3-position of cyclopropane); at 1.78 ppm (hydrogens of 2-CH$_3$ of cyclopentene).

EXAMPLE 3

(1S) 2-methyl-3-allyl-4-methylene-cyclopent-2-ene-1-yl
(1R, trans)
2,2-dimethyl-3-(2-methyl-1-propenyl)-cyclopropane-1-carboxylate A solution of 5 g of 1S-hydroxy-2-methyl-3-allyl-4-methylene-cyclopent-2-ene in 5 ml of benzene were added over 10 minutes at 20° C. to a mixture of 7 g of (1R, trans) 2,2-dimethyl-3-(2-methyl-1-propenyl)-cyclopropane-1-carboxylic acid chloride, 20 ml of benzene and 5 ml of pyridine and the mixture was stirred for 4 hours at 20°–25° C. 50 ml of water were added to the mixture and the mixture was stirred for 10 minutes. The decanted aqueous phase was extracted with benzene. The combined organic phases were washed with water, dried over magnesium sulfate and was filtered. The filtrate was evaporated to dryness under reduced pressure and the residue was chromatographed over silica gel. Elution with a 9-1 cyclohexane-ethyl acetate mixture containing 1‰ triethylamine yielded 8.76 g of (1S)-2-methyl-3-allyl-4-methylene-cyclopent-2-ene-1-yl (1R, trans) 2,2-dimethyl-3-(2-methyl-1-propenyl)-cyclopropane-1-carboxylate which was identical to the product of Example 2 having the same constants.

EXAMPLE 4

(1S) 2-methyl-3-allyl-4-methylene-cyclopent-2-ene-1-yl
(1R,cis)
2,2-dimethyl-3-cyclopentylidenemethyl-cyclopropane-1-carboxylate 30 ml of a benzene solution of (1R, cis) 2,2-dimethyl-3-cyclopentylidenemethyl-cyclopropane-1-carboxylic acid chloride prepared from 7 g of the corresponding acid were added at 20° C. over 15 minutes to a mixture of 4 g of 1S-hydroxy-2-methyl-3-allyl-4-methylene-cyclopent-2-ene, 10 ml of benzene and 5 ml of pyridine and the mixture was stirred at 20° C. for 20 hours and was then poured into 30 ml of water. The mixture was stirred for 10 minutes and was then extracted with methylene chloride. The combined organic phases were washed with water, dried over magnesium sulfate and filtered. The filtrate was evaporated to dryness under reduced pressure and the residue was chromatographed over silica gel. Elution with a 95-5 cyclohexane-ethyl acetate mixture containing 1‰ triethylamine yielded 4.1 g of (1S) 2-methyl-3-allyl-4-methylene-cyclopent-2-ene-1-yl (1R, cis) 2,2-dimethyl-3-cyclopentylidenemethyl-cyclopropane-1-carboxylate.

Analysis: $C_{22}H_{30}O_2$: Calculated: %C 80.93, %H 9.26; Found: 81.2, 9.4.

IR Spectrum (chloroform): Absorption at 1715 cm$^{-1}$ (carbonyl of ester); at 1635 cm$^{-1}$ (C=C); at 918–995 cm$^{-1}$ (>C=CH$_2$).

EXAMPLE 5

(1S) 2-methyl-3-allyl-4-methylene-cyclopent-2-ene-1-yl
(1R, trans)
2,2-dimethyl-3-cyclopentylidenemethyl-cyclopropane-1-carboxylate A solution of 7.08 g of (1R, trans) 2,2-dimethyl-3-cyclopentylidenemethyl-cyclopropane-1-carboxylic acid chloride in 3 ml of benzene was added over 10 minutes at 28° C. to a suspension of 5 g of 1S-hydroxy-2-methyl-3-allyl-4-methylene-cyclopent-2-ene in 15 ml of benzene and 2.96 ml of pyridine and the mixture was stirred at 20° C. for 17 hours. 20 ml of water were added to the mixture which was stirred for 10 minutes and the decanted aqueous phase was extracted with benzene. The combined organic phases were washed with water and the wash waters were extracted with benzene. The combined organic phases were dried over magnesium sulfate and were filtered and the filtrate was evaporated to dryness under reduced pressure. The residue was chromatographed over silica gel and was eluted with a 95-5 cyclohexane-ethyl acetate mixture containing 1‰ triethylamine to obtain 8.24 g of (1S) 2-methyl-3-allyl-4-methylene-cyclopent-2-ene-1-yl (1R, trans) 2,2-dimethyl-3-cyclopentylidenemethyl-cyclopropane-1-carboxylate with a specific rotation of $[\alpha]_D^{20} = -87° \pm 1°$ (c=0.9% in ethanol).

IR Spectrum (chloroform): Absorption at 1715 cm$^{-1}$ (carbonyl of ester); at 1635 cm$^{-1}$ (C=C); at 865 cm$^{-1}$ (>C=CH$_2$).

EXAMPLE 6

(1S) 2-methyl-3-allyl-4-methylene-cyclopent-2-ene-1-yl
(1R, cis)
2,2-dimethyl-3-(2-oxo-3-tetrahydrofuranylidenemethyl)cyclopropane-1-carboxylate A solution of 4.40 g of 1S-hydroxy-2-methyl-3-allyl-4-methylene-cyclopent-2-ene in 10 ml of benzene was added at 10° C. over 10 minutes to a suspension of 7.6 g of (1R, cis) 2,2-dimethyl-3-(2-oxo-3-tetrahydrofuranylidenemethyl)-cyclopropane-1-carboxylic acid chloride in 30 ml of benzene and 2.6 ml of pyridine and the mixture was held at 20° C. for 16 hours. 20 ml of water were added to the mixture followed by 20 ml of methylene chloride. The mixture was stirred and the aqueous phase was extracted with methylene chloride. The combined organic phases were washed with water, dried over magnesium sulfate and was filtered and the filtrate was evaporated to dryness under reduced pressure. The gelatinous residue was empasted with essence G (b.p.=40°-70° C.) and was then chromatographed over silica gel and was eluted with a 9-1 benzene-ethyl acetate mixture to obtain 4.01 g of (1S) 2-methyl-3-allyl-4-methylene-cyclopent-2-ene-1-yl (1R, cis) 2,2-dimethyl-3-(2-oxo-3-tetrahydrofuranylidene methyl)-cyclopropane-1-carboxylate melting at 93° C.

Analysis: $C_{21}H_{26}O_4$: Calculated: %C 73.66, %H 7.66; Found: 73.4, 7.5.

IR Spectrum (chloroform): Absorptions at 1750-1720 cm$^{-1}$ (carbonyls of lactone and ester); at 1667-1633 cm$^{-1}$ (C=C); at 992-916 cm$^{-1}$ (—CH=CH$_2$).

EXAMPLE 7

(1S) 2-methyl-3-allyl-4-methylene-cyclopent-2-ene-1-yl
(1R, trans)
2,2-dimethyl-3-(2-oxo-3-tetrahydrofuranylidenemethyl)cyclopropane-1-carboxylate A solution of 5.4 g of (1R, trans) 2,2-dimethyl-3-(2-oxo-3-tetrahydrofuranylidenemethyl)-cyclopropane-1-carboxylic acid chloride in 50 ml of benzene was added at less than 25° C. over 15 minutes to a suspension of 3 g of (1S)-hydroxy-2-methyl-3-allyl-4-methylene-cyclopent-2-ene in 10 ml of benzene and 3 ml of pyridine at 20° C. and the mixture was stirred at 20° C. for 20 hours. 30 ml of water were added and the mixture was stirred for 15 minutes. The decanted aqueous phase was extracted with benzene and the combined organic phases were washed with water, dried over magnesium sulfate and filtered. The filtrate was evaporated to dryness under reduced pressure and the residue was chromatographed over silica gel. Elution with a 7-3 cyclohexane-ethyl acetate mixture containing 1°/$_{oo}$ triethylamine yielded 2.61 g of (1S) 2-methyl-3-allyl-4-methylene-cyclopent-2-ene-1-yl (1R, trans) 2,2-dimethyl-3-(2-oxo-3-tetrahydrofuranylidenemethyl)-cyclopropane-1-carboxylate with a specific rotation of $[\alpha]_D^{20} = -28.5° \pm 2.5°$ (c=0.5% in ethanol).

Analysis: $C_{21}H_{26}O_4$: Calculated: %C 73.65, %H 7.65; Found: 73.9, 7.7.

IR Spectrum (chloroform): Absorptions at 1753 cm$^{-1}$-1718 cm$^{-1}$ (carbonyls of lactone and ester); at 1673 cm$^{-1}$-1633 cm$^{-1}$ (C=C); at 992-916 cm$^{-1}$ (—CH=CH$_2$).

EXAMPLE 8

(1S) 2-methyl-3-allyl-4-methylene-cyclopent-2-ene-1-yl
(1R, cis)
2,2-dimethyl-3-(2-oxo-3-tetrahydrothienylidenemethyl)cyclopropane-1-carboxylate 50 ml of a benzene solution of (1R, cis) 2,2-dimethyl-3-(2-oxo-3-tetrahydrothienylidenemethyl)-cyclopropane-1-carboxylic acid chloride prepared from 8.5 g of the corresponding acid were added at 20°-25° C. over 15 to 20 minutes to a suspension of 5 g of 1S-hydroxy-2-methyl-3-allyl-4-methylenecyclopent-2-ene in 10 ml of benzene and 5 ml of pyridine and the mixture was stirred at room temperature for 18 hours. 50 ml of water were added to the mixture and the mixture was stirred for 15 minutes. The decanted aqueous phase was extracted with 50 ml of methylene chloride and the combined organic phases were washed with water, dried over sodium sulfate and filtered. The filtrate was evaporated to dryness under reduced pressure and the residue was chromatographed over silica gel. Elution with a 9-1 benzene-ethyl acetate mixture containing 1°/$_{oo}$ triethylamine yielded 7.8 g of (1S) 2-methyl-3-allyl-4-methylene-cyclopent-2-ene-1-yl (1R, cis) 2,2-dimethyl-3-(2-oxo-3-tetrahydrothienylidenemethyl)cyclopropane-1-carboxylate which after crystallization from petroleum ether melted at 55° C. and had a specific rotation of $[\alpha]_D^{20} = -12° \pm 2°$ (c=0.8% in ethanol).

Analysis: $C_{21}H_{26}O_3S$: Calculated: %C 70.35, %H 7.31, %S 8.94; Found: 70.3, 7.4, 8.6.

NMR Spectrum (CDCl$_3$-60 MHz): Peaks at 1.29 ppm (doublet J=5.5 Hz) (hydrogens of geminal methyls); at 1.73 ppm (hydrogens of —C=C—CH$_3$); at 1.58 to 3.58 ppm (hydrogens of cyclopropane, of —CH$_2$—CH=CH$_2$ and CH$_2$—S—); at 4.67 to 6.17 ppm (hydrogens of —CH=CH$_2$ and 1-position of cyclopropane).

EXAMPLE 9

(1S) 2-methyl-3-allyl-4-methylene-cyclopent-2-ene-1-yl
(1R, trans)
2,2-dimethyl-3-(2-oxo-3-tetrahydrothienylidenemethyl)cyclopropane-1-carboxylate 50 ml of a benzene solution of (1R, trans) 2,2-dimethyl-3-(2-oxo-3-tetrahydrothienylidenemethyl)-cyclopropane-1-carboxylic acid chloride prepared from 8.5 g of the corresponding acid were added at 20°-25° C. over 15 to 20 minutes to a suspension of 5 g of 1S-hydroxy-2-methyl-3-allyl-4-methylene-cyclopent-2-ene in 20 ml of benzene and 2 ml of pyridine and the mixture was stirred at room temperature for 18 hours. 50 ml of water were added to the mixture which was then stirred for 10 minutes. The decanted aqueous phase was extracted with methylene chloride and the combined organic phases were washed with water, dried over magnesium sulfate and filtered. The filtrate was evaporated to dryness and the residue was chromatographed over silica gel. Elution with an 8-2 cyclohexane-ethyl acetate mixture containing 1°/$_{oo}$ triethylamine yielded 7.47 g of pure (1S) 2-methyl-3-allyl-4-methylenecyclopent-2-ene-1-yl (1R, trans) 2,2-dimethyl-3-(2-oxo-3-tetrahydrothienylidenemethyl)-cyclopropane-1-carboxylate with a specific rotation of $[\alpha]_D^{20} = -61.5° \pm 15°$ (c=0.8% in ethanol).

Analysis: $C_{21}H_{26}O_3S$: Calculated: %C 70.35, %H 7.31, %S 8.94; Found: 70.2, 7.6, 8.6.

NMR Spectrum ($CDCl_3$-60 MHz): Peaks at 1.28 ppm (doublet J=3.5 Hz) (geminal methyls); at 1.78 ppm (hydrogens of $CH_3$—C=); at 2.64 ppm (doublet J=13 Hz) (hydrogens of cyclopropane and —$CH_2S$—); at 4.67 to 5.25 ppm (hydrogens of =$CH_2$); at 6.2 ppm (doublet J=10 Hz) (ethylenic hydrogens); at 5.5 to 6.33 ppm (hydrogens of —CH=$CH_2$ and —COO—CH).

EXAMPLE 10

E and Z isomers of (1S) 2-methyl-3-allyl-4-methylene-cyclopent-2-ene-1-yl (1R, cis) 2,2-dimethyl-3-(2-cyanoethenyl)cyclopropane-1-carboxylate A solution of the E and Z isomers of (1R, cis) 2,2-dimethyl-3-(2-cyanoethenyl)-cyclopropane-1-carboxylic acid chloride in 10 ml of benzene was added with stirring at room temperature to a suspension of 6.1 g of 1S-hydroxy-2-methyl-3-allyl-4-methylene-cyclopent-2-ene in 60 ml of benzene and 8 ml of pyridine and the mixture was stirred for one hour and was then poured into water. The aqueous phase was extracted with isopropyl ether and the combined organic phases were washed with water, dried over sodium sulfate and evaporated to dryness under reduced pressure. The residue was chromatographed over silica gel and was eluted with benzene containing 1‰ triethylamine to obtain 2.5 g of Z isomer of (1S) 2-methyl-3-allyl-4-methylene-cyclopent-2-ene-1-yl (1R, cis) 2,2-dimethyl-3-(2-cyanoethenyl)-cyclopropane-1-carboxylate with a specific rotation of $[\alpha]_D^{20} = +66.5° \pm 2.5°$ (c=0.6% in benzene) and 1.9 g of the E isomer of (1S) 2-methyl-3-allyl-4-methylene-cyclopent-2-ene-1-yl (1R, cis) 2,2-dimethyl-3-(2-cyanoethenyl)cyclopropane-1-carboxylate with a specific rotation of $[\alpha]_D^{20} = -58° \pm 2.5°$ (c=0.7% in benzene).

Analysis of Z isomer: $C_{19}H_{23}NO_2$: Calculated: %C 76.73, %H 7.80, %N 4.71; Found: 76.6, 7.8, 4.6.

IR Spectrum (chloroform): Absorption CN at 1714 $cm^{-1}$ (carbonyl); at 1612-973-2220 $cm^{-1}$ (>CH=CH); at 1635 $cm^{-1}$ (C=C); at 917 $cm^{-1}$ ($CH_2$=CH—); at 866-874 $cm^{-1}$ ($CH_2$=C<).

Analysis of E isomer: $C_{19}H_{23}NO_2$: Calculated: %C 76.73, %H 7.79, %N 4.71; Found: 76.3, 7.9, 4.4.

IR Spectrum (chloroform): Absorption at 2225 $cm^{-1}$ (—CN); at 1718 $cm^{-1}$ (carbonyl); at 1381 $cm^{-1}$ (geminal methyls); at 1633 $cm^{-1}$ (C=C); at 910–917 $cm^{-1}$ $CH_2$=CH).

EXAMPLE 11

(1S) 2-methyl-3-allyl-4-methylene-cyclopent-2-ene-1-yl (d) α-isopropyl-α-(4-chlorophenyl)-acetate A solution of 4.6 g of (d)α-isopropyl-α-(4-chlorophenyl)-acetic acid chloride in 5 ml of benzene was added with stirring at 20° C. to a suspension of 1S-hydroxy-2-methyl-3-allyl-4-methylene-cyclopent-2-ene in 30 ml of benzene and 5 ml of pyridine and the mixture was stirred at 20° C. for 16 hours and was then poured into water. The aqueous phase was extracted with isopropyl ether and the combined organic phases were dried over sodium sulfate and was filtered. The filtrate was evaporated to dryness under reduced pressure and the residue was chromatographed over silica gel. Elution with a 4-6 benzene-cyclohexane mixture containing 1‰ triethylamine yielded 4.8 g of pure (1S) 2-methyl-3-allyl-4-methylenecyclopent-2-ene-1-yl (d) α-isopropyl-α-(4-chlorophenyl)-acetate with a specific rotation of $[\alpha]_D^{20} = -81.5° \pm 2°$ (c=0.8% in benzene).

Analysis: $C_{21}H_{25}ClO_2$: Calculated: %C 73.13, %H 7.31, %Cl 10.28; Found: 73.2, 7.4, 10.2.

NMR Spectrum ($CDCl_3$-60 MHz): Peaks at 0.69 ppm and 1.05 ppm (2 doublets-J=6.5 Hz) (hydrogens of methyl of isopropyl); at 1.58 ppm (hydrogens of 2-$CH_3$ of cyclopentene); at 3.14 ppm (doublet J=10.5 Hz) (hydrogen α-to $COO^-$); at 5.33 to 6.17 ppm (2-hydrogen of allyl); at 4.73 to 5.07 ppm (hydrogens of 3-$CH_2$= of allyl and 4-position of cyclopentene.

EXAMPLE 12

(1S) 2-methyl-3-allyl-4-methylene-cyclopent-2-ene-1-yl (1R, trans) 2,2-dimethyl-3-(2,2-difluoroethenyl)-cyclopropane-1-carboxylate A solution of 3.88 g of (1R, trans) 2,2-dimethyl-3-(2,2-difluoroethenyl)-cyclopropane-1-carboxylic acid chloride in 5 ml of benzene was added with stirring below 30° C. to a suspension of 3 g of 1S-hydroxy-2-methyl-3-allyl-4-methylenecyclopent-2-ene in 30 ml of benzene and 4.5 ml of pyridine and the mixture was stirred at 20° C. for 4 hours and was then poured into water. The decanted aqueous phase was extracted with isopropyl ether and the combined organic phases were washed with water, dried over sodium sulfate and filtered. The filtrate was evaporated to dryness under reduced pressure and the residue was rectified under reduced pressure to obtain 2.3 g of pure (1S) 2-methyl-3-allyl-4-methylene-cyclopent-2-ene-1-yl (1R, trans) 2,2-dimethyl-3-(2,2-difluoroethenyl)cyclopropane-1-carboxylate with a boiling point of 113°-114° C. at 0.1 mm Hg and a specific rotation of $[\alpha]_D^{20} = -67° \pm 2.5°$ (c=0.6% in benzene).

Analysis: $C_{18}H_{22}F_2O_2$: Calculated: %C 70.11, %H 7.19, %F 12.32; Found: 69.8, 7.2, 12.5.

IR Spectrum (chloroform): Absorption at 1746-1716 $cm^{-1}$ (ester carbonyl and $CF_2$=C—); at 1636 $cm^{-1}$ (C=C of cyclopentene and —C=$CH_2$); at 920-991 $cm^{-1}$ (—CH=$CH_2$).

EXAMPLE 13

(1S) 2-methyl-3-allyl-4-methylene-cyclopent-2-ene-1-yl (1R, cis) 2,2-dimethyl-3-(2-fluoro-2-chloroethenyl)-cyclopropane-1-carboxylate A solution of 4.2 g of (1R, cis) 2,2-dimethyl-3-(2-fluoro-2-chloro-ethenyl)-cyclopropane-1-carboxylic acid chloride in 10 ml of benzene was added with stirring at 20° C. to a mixture of 3 g of 1S-hydroxy-2-methyl-3-allyl-4-methylene-cyclopent-2-ene in 20 ml of benzene and 5.5 ml of pyridine and the reaction mixture was stirred at 20° C. for 16 hours and was then poured into water. The decanted aqueous phase was extracted with isopropyl ether and the combined organic phases were dried over sodium sulfate and filtered. The filtrate was evaporated to dryness under reduced pressure and the residual oil was distilled to obtain 3.4 g of pure (1S) 2-methyl-3-allyl-4-methylene-cyclopent-2-ene-1-yl (1R, cis) 2,2-dimethyl-3-(2-fluoro-2-chloroethenyl)-cyclopropane-1-carboxylate with a boiling point of 125° C. at 0.1 mm Hg and a specific rotation of $[\alpha]_D^{20} = -10° \pm 2°$ (c=0.5% in benzene).

Analysis: $C_{18}H_{22}ClFO_2$: Calculated: %C 66.55, %H 6.83, %F 5.85, %Cl 10.92; Found: 65.9, 6.9, 6.0, 11.4.

IR Spectrum (chloroform): Absorption at 1716 cm$^{-1}$ (ester carbonyl); at 1675 cm$^{-1}$ (CFCl=); at 1636 cm$^{-1}$ (C=C); at 870-918-993 cm$^{-1}$ (CH$_2$=CH— and CH$_2$=C<).

EXAMPLE 14

(1S) 2-methyl-3-allyl-4-methylene-cyclopent-2-ene-1-yl
(1R, cis)
2,2-dimethyl-3-(2,2-dichloroethyl)-cyclopropane-1-carboxylate 7 g of (1R, cis) 2,2-dimethyl-3-(2,2-dichloroethenyl)-cyclopropane-1-carboxylic acid chloride were added at 10° C. to a solution of 4.40 g of 1S-hydroxy-2-methyl-3-allyl-4-methylene-cyclopent-2-ene in 15 ml of benzene and 2.6 ml of pyridine and the reaction mixture was stirred at 20° C. for 16 hours. 20 ml of water were added to the mixture and after stirring the mixture for 5 minutes, 20 ml of methylene chloride were added thereto. The decanted aqueous phase was extracted with methylene chloride and the combined organic phases were washed with water, dried over magnesium sulfate and filtered. The filtrate was evaporated to dryness under reduced pressure and the residue was chromatographed over silica gel. Elution with a 95-5 cyclohexane-ethyl acetate mixture containing 0.5°/$_{oo}$ triethylamine yielded 4.97 g of (1S) 2-methyl-3-allyl-4-methylene-cyclopent-2-ene-1-yl (1R, cis) 2,2-dimethyl-3-(2,2-dichloroethenyl)-cyclopropane-1-carboxylate with a specific rotation of $[\alpha]_D^{20} = -27.5° \pm 1.5°$ (c=0.9% in ethanol).

Analysis: C$_{18}$H$_{22}$O$_2$Cl$_2$: Calculated: %C 63.35, %H 6.49, %Cl 20.77; Found: 63.4, 6.6, 20.9.

IR Spectrum (chloroform): Shoulder at 1724-1713 cm$^{-1}$ (ester carbonyl); Absorption at 1633-1619 cm$^{-1}$ (C=C); at 995-919 cm$^{-1}$ (CH$_2$=CH—).

EXAMPLE 15

(1S) 2-methyl-3-allyl-4-methylene-cyclopent-2-ene-1-yl
(1R, trans)
2,2-dimethyl-3-(2,2-dichloroethenyl)-cyclopropane-1-carboxylate A solution of 7 g of (1R, trans) 2,2-dimethyl-3-(2,2-dichloroethenyl)-cyclopropane-1-carboxylic acid chloride in 5 ml of benzene was added over 15 minutes to a solution of 4.40 g of (1S) hydroxy-2-methyl-3-allyl-4-methylene-cyclopent-2-ene in 15 ml of benzene and 2.6 ml of pyridine and the mixture was stirred for 16 hours. 20 ml of water were added to the mixture and after stirring for 5 minutes, the decanted aqueous phase was extracted with benzene. The combined organic phases were washed with water, dried over magnesium sulfate and filtered. The filtrate was evaporated to dryness under reduced pressure and the residue was chromatographed over silica gel. Elution with a 95-5 cyclohexane-ethyl acetate mixture containing 1°/$_{oo}$ triethylamine yielded 6.99 g of pure (1S) 2-methyl-3-allyl-4-methylene-cyclopent-2-ene-1-yl (1R, trans) 2,2-dimethyl-3-(2,2-dichloroethenyl)-cyclopropane-1-carboxylate with a specific rotation of $[\alpha]_D^{20} = -45.5° \pm 1.5°$ (c=1% in ethanol).

Analysis: C$_{18}$H$_{22}$O$_2$Cl$_2$: Calculated: %C 63.35, %H 6.49, %Cl 20.77; Found: 63.3, 6.6, 20.3.

IR Spectrum (chloroform): Absorption at 1717 cm$^{-1}$ (ester carbonyl); at 1633-1618 cm$^{-1}$ (C=C); at 990-917 cm$^{-1}$ (CH$_2$=CH—).

EXAMPLE 16

(1S) 2-methyl-3-allyl-4-methylene-cyclopent-2-ene-1-yl
(1R, cis)
2,2-dimethyl-3-(2,2-dibromoethenyl)-cyclopropane-1-carboxylate A solution of 7.45 g of (1R, cis) 2,2-dimethyl-3-(2,2-dibromoethenyl)-cyclopropane-1-carboxylic acid chloride in 2 ml of benzene was added over 10 minutes at 25° C. to a suspension of 3.49 g of 1S-hydroxy-2-methyl-3-allyl-4-methylene-cyclopent-2-ene in 15 ml of benzene and 2.06 ml of pyridine and the mixture was stirred at 20° C. for 20 hours. 20 ml of water were added to the mixture which was stirred for 10 minutes and the decanted aqueous phase was extracted with 20 ml of methylene chloride. The combined organic phases were washed with water, dried over magnesium sulfate and filtered. The filtrate was evaporated to dryness under reduced pressure and the residue was twice chromatographed over silica gel. Elution with a 7-3 benzene-ethyl acetate mixture containing 1°/$_{oo}$ triethylamine and then with a 95-5 cyclohexane-ethyl acetate mixture containing 1°/$_{oo}$ triethylamine yielded 4.983 g of pure (1S) 2-methyl-3-allyl-4-methylene-cyclopent-2-ene-1-yl (1R, cis) 2,2-dimethyl-3-(2,2-dibromoethenyl)-cyclopropane-1-carboxylate with a specific rotation of $[\alpha]_D^{20} = -3.50° \pm 2°$ (c=0.7% in chloroform).

Analysis: C$_{18}$H$_{22}$O$_2$Br$_2$: Calculated: %C 50.25, %H 5.15, %Br 37.15; Found: 50.5, 5.2, 36.8.

| Circular dichroism (dioxane): | |
| --- | --- |
| Max. at 347 nm | $\Delta\epsilon = +0.005$ |
| Max. at 330 nm | $\Delta\epsilon = +0.010$ |
| Max. at 320 nm | $\Delta\epsilon = +0.012$ |
| Max. at 250 nm | $\Delta\epsilon = -3.16$ |
| Max. at 221 nm | $\Delta\epsilon = -3.92$ |

EXAMPLE 17

(1S) 2-methyl-3-allyl-4-methylene-cyclopent-2-ene-1-yl
(1R, trans)
2,2-dimethyl-3-(2,2-dibromoethenyl)-cyclopropane-1-carboxylate A solution of 9.3 g of (1R, trans) 2,2-dimethyl-3-(2,2-dibromoethenyl)-cyclopropane-1-carboxylic acid chloride in 30 ml of benzene was added over 15 minutes at 20°-25° C. to a solution of 3 g of 1S-hydroxy-2-methyl-3-allyl-4-methylenecyclopent-2-ene in 5 ml of benzene and 5 ml of pyridine and the mixture was stirred at 20° C. for 20 hours. 50 ml of water were added to the mixture which was stirred for 15 minutes and the decanted aqueous phase was extracted with benzene. The combined organic phases were washed with water, dried over magnesium sulfate and filtered. The filtrate was evaporated to dryness under reduced pressure and the residue was chromatographed over silica gel. Elution with a 95-5 cyclohexane-ethyl acetate mixture containing 1°/$_{oo}$ triethylamine yielded 4.05 g of pure (1S) 2-methyl-3-allyl-4-methylenecyclopent-2-ene-1-yl (1R, trans) 2,2-dimethyl-3-(2,2-dibromoethenyl)-cyclopropane-1-carboxylate with a specific rotation of $[\alpha]_D^{20} = -41.5° \pm 2°$ (c=1% in ethanol).

Analysis: C$_{18}$H$_{22}$O$_2$Br$_2$: Calculated: %C 50.25, %H 5.15, %Br 37.15; Found: 50.9, 5.3, 36.6.

NMR Spectrum (CDCl$_3$-60 MHz): Peaks at 1.24 ppm (doublet-J=5.5 Hz) (hydrogens of 2-CH$_3$ of cyclopropane); at 1.64 ppm (doublet=J=5 Hz) (1-hydrogen of cyclopropane); at 1.8 ppm and hydrogens of 2-CH₃ of cyclopentene); at 2.12 ppm and 2.24 ppm (2 doublets-J=6 Hz) (3-hydrogen of cyclopropane); at 4.67 to 5.17 ppm (hydrogens of 3 CH$_2$= of allyl and hydrogens of 4-methylene of cyclopentene); at 5.5 to 6.33 ppm (2-hydrogen of allyl); at 5.58 ppm (1-hydrogen of cyclopentene); at 6.17 ppm (doublet-J=7.5 Hz) (1-hydrogen of 2,2-dibromoethenyl).

EXAMPLE 18

(1RS) 2-methyl-3-(3-methyl-2-butenyl)-4-methylene-cyclopent-2-ene-1-yl (1R, trans) 2,2-dimethyl-3-(2-methyl-1-propenyl)cyclopropane-1-carboxylate STEP A: ETHYL 7-methyl-3-oxo-6-octenoate A mixture of 1.4 g of ferric nitrate in 1200 ml of liquid ammonia was formed at −60° C. and was then stirred for 5 minutes after which 2 g of sodium were added thereto at −60° C. The mixture was stirred for 10 minutes and 104 g of sodium were added at −55°±5° C. over 2½ hours. The mixture was stirred at −55° C. for one hour. 300 g of ethyl acetylacetate were added thereto over 30 minutes at less than −30° C. 1000 ml of ether at −20° C. were added to the mixture which was then stirred for 5 minutes. 289 g of 1-chloro-3-methyl-2-butene were added over 30 minutes at less than −25° C. and the mixture stood at room temperature for 17 hours. 1000 ml of ether were progressively added at less than +15° C. followed by a solution of 250 ml of acetic acid in 1000 ml of water. The decanted aqueous phase was extracted with ether and the combined organic phases were washed with 2 N hydrochloric acid, then with water, dried over sodium sulfate and evaporated to dryness under reduced pressure. The residue was rectified under reduced pressure to obtain 175.5 g of ethyl 7-methyl-3-oxo-6-octenoate with a boiling point of 98° to 107° C. at 3 mm Hg.

NMR Spectrum (CDCl₃-60 MHz): Peaks at 1.28 ppm (triplet-J=7 Hz) and at 2.9 ppm (quadruplet J=7.5 Hz) (hydrogens of —COOC₂H₅); at 3.62 ppm (hydrogens of 2-CH$_2$=); at 1.64 ppm (doublet J=3 Hz) (hydrogens of 7-CH₃); at 5.08 ppm (6-hydrogen).

STEP B: 3-hydroxy-9-methyl-8-decene-2,5-dione 97 ml of 10 N sodium hydroxide solution were added over one hour at less than 33° C. to a suspension of 175 g of ethyl 7-methyl-3-oxo-6-octenoate in 875 ml of water and the mixture was stirred at room temperature for 20 hours and 25 ml of acetic acid were added thereto to obtain a pH of 7. An aqueous solution containing 396 g of pyruvaldehyde (16.8% by weight) was added to the mixture at 20° to 25° C. while maintaining a pH of 7 and the mixture was stirred for 20 hours at room temperature during which 30 ml of acetic acid were added to keep the pH at 7. 1000 ml of methylene chloride were added thereto and the mixture was stirred for 10 minutes. The decanted aqueous phase was extracted with methylene chloride and the combined organic phases were dried over sodium sulfate and evaporated to dryness under reduced pressure to obtain 175 g of 3-hydroxy-9-methyl-8-decene-2,5-dione.

STEP C:
1RS-hydroxy-2-methyl-3-(3-methyl-2-butenyl)-4-oxocyclopent-2-ene

Nitrogen was bubbled through 875 ml of 1 N sodium hydroxide solution for one hour and then 175 mg of hydroquinone were added thereto at 3° C. 175 g of 3-hydroxy-9-methyl-8-decene-2,5-dione were added to the mixture over one hour at 2°±1° C. and the mixture was stirred for 2½ hours at that temperature. Then, 80 ml of concentrated hydro-chloric acid were added with stirring and the mixture was stirred for 30 minutes during which the temperature rose to 20° C. 200 g of sodium chloride were added to the mixture which was then stirred for 10 minutes. 1000 ml of methylene chloride were added thereto and the decanted aqueous phase was extracted with methylene chloride. The combined organic phases were dried over sodium sulfate and evaporated to dryness under reduced pressure. The residue was rectified under reduced pressure to obtain 53.4 g of 1RS-hydroxy-2-methyl-3-(3-methyl-2-butenyl)-4-oxo-cyclopent-2-ene with a boiling point of 143° to 148° C. at 0.5 mmHg.

NMR Spectrum (CDCl₃-60 MHz): Peaks at 1.72 ppm (hydrogens of —CH₃ of dimethylallyl); at 2.87 ppm (doublet - J=7 Hz) (1-hydrogens of side chain); at 4.7 ppm (α-hydrogen of OH); at 5.03 ppm (triplet - J=7 Hz) (2-hydrogen of side chain); at 2.67 ppm (hydrogen of —OH); at 2.08 to 2.92 ppm (4=CH₂ of cyclopentene).

STEP D:
1RS-hydroxy-2-methyl-3-(3-methyl-2-butenyl)-4-methylene-cyclopent-2-ene 9.93 g of potassium tert.-butylate were added in 6 fractions over 30 minutes to a stirred suspension of 29.7 g of triphenylmethylphosphonium bromide, 100 ml of ether and 7.84 ml of tert.-butanol and the reaction mixture was stirred at 20° C. under an inert atmosphere for 5 hours. The mixture was cooled to 0° C. and a solution of 10 g of 1RS-hydroxy-2-methyl-3-(3-methyl-2-butenyl)-4-oxo-cyclopent-2-ene in 10 ml of ether was added thereto over 20 minutes. The mixture was stirred at 0° C. under an inert atmosphere for 17 hours and after allowing the temperature to rise to 20° C., the mixture was stirred for another 3 hours and was then poured into an aqueous saturated monosodium phosphate solution. The mixture was stirred for 15 minutes and the decanted aqueous phase was extracted with ether. The combined organic phases were dried over magnesium sulfate, filtered and evaporated to dryness under reduced pressure. The residue was taken up in ether and the mixture was stirred at 0° C. for 10 minutes and was vacuum filtered. The recovered product was washed with ether. The combined filtrates were evaporated to dryness under reduced pressure to obtain 19.54 g of raw product which was chromatographed over silica gel. Elution with a 7-3 benzene-ethyl acetate mixture containing 1‰ triethylamine yielded 7.24 g of 1RS-hydroxy-2-methyl-3-(3-methyl-2-butenyl)-4-methylene-cyclopent-2-ene with an Rf=0.55.

IR Spectrum (chloroform): Absorption complex at 3605–3580 cm⁻¹ characteristic of OH; at 1630 cm⁻¹ (C=C); at 865 cm⁻¹ (C=CH₂).

NMR Spectrum (CDCl₃-60 MHz): Peaks at 1.7 ppm (hydrogens of —CH₃ on side chain); at 1.83 ppm (hydrogens of 2—CH₃); at 1.98 ppm (hydrogen of 1—OH); at 2.83 to 2.95 ppm (1-hydrogens of 1—CH₂ of side chain); at 5.03 ppm (triplet - J=7 Hz) (3-hydrogens of side chain); at 4.42 to 4.83 ppm (α-hydrogen of OH and 4-=CH$_2$).

STEP E: (1RS) 2-methyl-3-(3-methyl-2-butenyl)-4-methylenecyclopent-2-ene-1-yl (1R, trans) 2,2-dimethyl-3-(2-methyl-1-propenyl)-cyclopropane-1-carboxylate A solution of 3.61 g of (1R, trans) 2,2-dimethyl-3-(2-methyl-1-propenyl)-cyclopropane-1-carboxylic acid chloride in 5 ml of benzene was added over 15 minutes at 25° C. to a mixture of 3 g of the product of Step D in 10 ml of benzene and 1.64 ml of pyridine and the mixture was stirred under nitrogen at 20° C. for 16 hours. 20 ml of water were added to the mixture which was stirred for 10 minutes after which 20 ml of methylene chloride were added thereto. The mixture was stirred for 10 minutes and the decanted aqueous phase was extracted with methylene chloride. The combined organic phases were washed with water, dried over magnesium sulfate and filtered. The filtrate was evaporated to dryness under reduced pressure and the residue was chromatographed over silica gel. Elution with 95-5 cyclohexane-ethyl acetate mixture containing 0.5°/$_{oo}$ triethylamine yielded 3.564 g of pure (1RS) 2-methyl-3-(3-methyl-2-butenyl)-4-methylenecyclopent-2-ene-1-yl (1R, trans) 2,2-dimethyl-3-(2-methyl-1-propenyl)-cyclopropane-1-carboxylate with a specific rotation of $[\alpha]_D^{20} = -7.5° \pm 1°$ (c=1.2% in ethanol).

Analysis: $C_{22}H_{32}O_2$; Calculated: %C 80.44; %H 9.82; Found: 80.3; 9.7.

NMR Spectrum (CDCl$_3$- 60 MHz): Peaks at 1.19 ppm (doublet - J=8.5 Hz) (hydrogens of 2—CH$_3$ of cyclopropanol); at 1.37 ppm (doublet - J=5 Hz) (1-hydrogen of cyclopropane); at 1.7 ppm (hydrogens of terminal CH$_3$ of dimethylallyl of cyclopentene); at 1.78 ppm (hydrogens of 2—CH$_3$ of cyclopentene); at 2.89 ppm (1-hydrogens of dimethylallyl of cyclopentene); at 4.67 to 5.25 ppm (ethylenic hydrogens); at 5.63 ppm (1-hydrogen of cyclopentene).

EXAMPLE 19

(1RS) 2-methyl-3-(3-methyl-2-butenyl)-4-methylene-cyclopent-2-ene-1-yl (1R, trans) 2,2-dimethyl-3-cyclopentylidenemethylcyclopropane-1-carboxylate A solution of 2 g of (1RS) hydroxy-2-methyl-3-(3-methyl-2-butenyl)-4-methylene-cyclopent-2-ene in 5 ml of benzene was added over 10 minutes at 25° C. to a suspension of 3.08 g of (1R, trans) 2,2-dimethyl-3-cyclopentylidenemethylcyclopropane-1-carboxylic acid chloride in 10 ml of benzene and 1.22 ml of pyridine and the mixture was stirred under nitrogen at 20° C. for 16 hours. 20 ml of water were dried to the mixture which was stirred for 10 minutes and 20 ml of methylene chloride were added thereto. The mixture was stirred for 5 minutes and the decanted aqueous phase was extracted with methylene chloride. The combined organic phases were washed with water and the wash waters were extracted with methylene chloride. The combined organic phases were dried over magnesium sulfate and filtered and the filtrate was evaporated to dryness under reduced pressure. The residue was chromatographed over silica gel and was eluted with a 95-5 cyclohexane-ethyl acetate mixture containing 0.5°/$_{oo}$ triethylamine to obtain 2.448 g of (1RS) 2-methyl-3-(3-methyl-2-butenyl)-4-methylene-cyclopent-2-ene-1-yl (1R, trans) 2,2-dimethyl-3-cyclopentylidenemethyl-cyclopropane-1-carboxylate with a specific rotation of $[\alpha]_D^{20} = -19° \pm 1.5°$ (c=0.9% in ethanol).

Analysis: $C_{24}H_{34}O_2$; Calculated: %C 81.31; %H 9.66; Found: 81.4; 9.6.

NMR Spectrum (CDCl$_3$-60 MHz): Peaks at 1.20 ppm (doublet - J=7.5 Hz) (hydrogens of 2—CH$_3$ of cyclopropane); at 1.41 ppm (doublet - J=5.5 Hz) (1-hydrogen of cyclopropane); at 1.7 ppm (hydrogens of terminal CH$_3$— of dimethylallyl of cyclopentene); at 1.78 ppm (hydrogens of 2—CH$_3$ of cyclopentene); at 1.83 to 2.33 ppm (3-hydrogens of cyclopropane); at 2.27 ppm (2- and 5-hydrogens of cyclopentylidene); at 4.75 to 5.17 ppm (hydrogens of 4=CH$_2$ of cyclopentene); at 5.62 ppm (1-hydrogen of cyclopentene); 5—m (2-hydrogen of dimethylallyl).

EXAMPLE 20

(1RS) 2-methyl-3-(3-methyl-2-butenyl)-4-methylene-cyclopent-2-ene-1-yl (1R, trans) 2,2-dimethyl-3-(2-oxo-3-tetrahydrofuranylidenemethyl)-cyclopropane-1-carboxylate A solution of 3.85 g of (1R, trans) 2,2-dimethyl-3-(2-oxo-3-tetrahydrofuranylidenemethyl)-cyclopropane-1-carboxylic acid chloride in 30.6 ml of benzene was added over 15 minutes at 25° C. to a mixture of 2 g of 1RS-hydroxy-2-methyl-3-(3-methyl-2-butenyl)-4-methylene-cyclopent-2-ene in 5 ml of benzene and 1.22 ml of pyridine and the mixture was stirred under nitrogen for 16 hours. 30 ml of water were added to the mixture which was stirred for 5 minutes and then 10 ml of methylene chloride were added thereto. The mixture was stirred for 5 minutes and the decanted aqueous phase was extracted with methylene chloride. The combined organic phases were washed with water, dried over magnesium sulfate and filtered and the filtrate was evaporated to dryness under reduced pressure. The residue was chromatographed over silica gel and was eluted with a 7-3 benzene-ethyl acetate mixture containing 0.5°/$_{oo}$ triethylamine to obtain 2.933 g of (1RS) 2-methyl-3-(3-methyl-2-butenyl)-4-methylene-cyclopent-2-ene-1-yl (1R, trans) 2,2-dimethyl-3-(2-oxo-3-tetrahydrofuranylidenemethyl)cyclopropane-1-carboxylate with a specific rotation of $[\alpha]_D^{20} = +1.5° \pm 1.5°$ (c=0.7% in ethanol).

Analysis: $C_{23}H_{30}O_4$; Calculated: %C 74.56, %H 8.16; Found: 73.7, 8.1.

IR Spectrum (chloroform): Absorption at 1753–1718 cm$^{-1}$ (carbonyl of lactone and ester); at 1675–1633 cm$^{-1}$ (C=C); at 992–916 cm$^{-1}$ (—CH=CH$_2$).

EXAMPLE 21

(1RS) 2-methyl-3-(3-methyl-2-butenyl)-4-methylene-cyclopent-2-ene-1-yl (1R, cis) 2,2-dimethyl-3-(2,2-dibromoethenyl)-cyclopropane-1-carboxylate A solution of 1.02 g of 1RS-hydroxy-2-methyl-3-(3-methyl-2-butenyl)-4-methylene-cyclopent-2-ene in 5 ml of benzene was added over 20 minutes at 20°-25° C. to a suspension of 2.35 g of (1R, cis) 2,2-dimethyl-3-(2,2-dibromoethenyl)cyclopropane-1-carboxylic acid chloride in 10 ml of benzene and 0.65 ml of pyridine and the mixture was stirred at 20° C. for 16 hours. 30 ml of water were added to the mixture which was stirred for 10 minutes and 20 ml of methylene chloride were added thereto. The mixture was stirred for 10 minutes and the decanted aqueous phase was extracted with methylene chloride. The combined organic phases were washed with water, dried over magnesium sulfate and filtered and the filtrate was evaporated to dryness under reduced pressure. The residue was chromatographed over silica gel and was eluted with a 95-5 cyclohexane-ethyl acetate mixture containing 0.5‰ triethylamine to obtain 1.87 g of (1RS) 2-methyl-3-(3-methyl-2-butenyl)-4-methylene-cyclopent-2-ene-1-yl (1R, cis) 2,2-dimethyl-3-(2,2-dibromoethenyl)-cyclopropane-1-carboxylate with a specific rotation of $[\alpha]_D^{20} = -10° \pm 1°$ (c=1% in ethanol).

Analysis: $C_{20}H_{26}O_2Br_2$: Calculated: %C 52.42; %H 5.72; %Br 34.87; Found: 52.7; 5.9; 39.8.

NMR Spectrum (CDCl$_3$-60 MHz); Peaks at 1.26 ppm (doublet - J=2 Hz) (hydrogens of 2—CH$_3$ of cyclopropane); 1.7 ppm (hydrogens of CH$_3$ of 3-dimethylallyl chain of cyclopentene); at 1.78 ppm (hydrogens of 2—CH$_3$ of cyclopentene); at 2.92 ppm (doublet - J=7 Hz) (4hydrogens of dimethylallyl chain of cyclopentene); at 4.67 to 5 ppm hydrogens of 4=CH$_2$ of cyclopentene); at 5.08 ppm (triplet - J=7 Hz) (2-hydrogen of cyclopentene side chain); at 5.6 ppm (1-hydrogen of cyclopentene); at 6.8 ppm (double - J=7 Hz) (last ethylenic hydrogen of dibromovinyl).

EXAMPLE 22

(1S) 2-methyl-3-allyl-4-dicyanomethylene-cyclopent-2-ene-1-yl (1R, trans) 2,2-dimethyl-3-cyclopentylidenemethyl-cyclopropane-1-carboxylate 2 g of malonitrile, 580 mg of ammonium acetate and 2.4 ml of acetic acid were added with stirring to a mixture of 5 g of (1S) 2-methyl-3-allyl-4-oxo-cyclopent-2-ene-1-yl (1R, trans) 2,2-dimethyl-3-cyclopentylidenemethyl-cyclopropane-1-carboxylate in 20 ml of benzene and the mixture was refluxed for 18 hours. After the addition of 3 g of ammonium acetate and 2.5 ml of acetic acid, reflux was continued for 44 hours after which water was added to the mixture. The mixture was extracted with ether and the ether phase was washed with water, then saturated aqueous sodium bicarbonate solution and then with water, dried over magnesium sulfate and filtered. The filtrate was evaporated to dryness under reduced pressure and the residue was chromatographed over silica gel. Elution with a 95-5-0.1 benzene-ethyl acetate-triethylamine mixture yielded 1.296 g of (1S) 2-methyl-3-allyl-4-dicyanomethylenecyclopent-2-ene-1-yl (1R, trans) 2,2-dimethyl-3-cyclopentylidenemethyl-cyclopropane-1-carboxylate with a specific rotation of $[\alpha]_D^{20} = -130° \pm 2.5°$ (c=0.6% in ethanol).

Analysis: $C_{24}H_{28}O_2N_2$: Calculated: %C 76.56; %H 7.5; %N 7.4; Found: 76.5; 7.7; 7.1.

IR Spectrum (chloroform): Absorption at 2229 cm$^{-1}$ (—CN); at 1725 cm$^{-1}$ (ester carbonyl); at 1640-1617 cm$^{-1}$ (C=C).

EXAMPLE 23

(1S) 2-methyl-3-allyl-4-dichloromethylene-cyclopent-2-ene-1-yl (1R, trans) 2,2-dimethyl-3-cyclopentylidenemethyl-cyclopropane-1-carboxylate A solution of 7.56 g of chloroform in 36 ml of heptane was added at −20° C. over 75 minutes under an inert atmosphere to a mixture of 11.1 g of triphenylphosphine, 128 ml of heptane, 6 ml of tert.-butanol and 7.08 g of potassium tert.-butylate and the mixture was stirred at −20° C. for 20 hours to obtain 160 ml of an ylide solution. 80 ml of the solution were held at −20° C. and a solution of 2.3 g of (1S) 2-methyl-4-allyl-4-oxo-cyclopent-2-ene-1-yl (1R, trans) 2,2-dimethyl-3-cyclopentylidenemethyl-cyclopropane-1-carboxylate in 15 ml of tetrahydrofuran was added at −20° C. over 20 minutes to the other 80 ml of ylide solution. The temperature was allowed to rise to 25° C. and the mixture was held at 25° C. for 6 hours. The mixture was cooled to −20° C. and the remainder of the ylide solution was added thereto. The temperature was allowed to rise to room temperature and was then stirred under an inert atmosphere for 16 hours. The mixture was filtered and the filtrate was washed with ether. The filtrate was poured into an iced monosodium phosphate solution and the mixture was stirred and decanted. The aqueous phase was extracted with ether and the combined organic phases were washed with water until the wash water was neutral, dried over magnesium sulfate and filtered. The filtrate was evaporated to dryness under reduced pressure and the residue was chromatographed over silica gel. Elution with benzene containing 1‰ triethylamine yielded 2.22 g of (1S) 2-methyl-3-allyl-4-dichloromethylene-cyclopent-2-ene-1-yl (1R, trans) 2,2-dimethyl-3-cyclopentylidenemethyl-cyclopropane-1-carboxylate with a specific rotation of $[\alpha]_D^{20} = -89° \pm 2.2°$ (c=0.65% in ethanol).

Analysis: $C_{22}H_{28}O_2Cl_2$; Calculated: %C 66.83; %H 7.14; %Cl 17.94; Found: 66.9; 7.2; 17.7.

NMR Spectrum (CDCl$_3$-60 MHz): Peaks at 1.21 ppm (doublet - J=7 Hz) (hydrogens of 2—CH$_3$ of cyclopropane); at 1.42 ppm (doublet - J=5.5 Hz) (1-hydrogen of cyclopropane); at 0.178 ppm (3-hydrogens of allyl chain); oat 4.83 to 5.12 ppm (hydrogens of 4-methylene of cyclopentene and ethylenic hydrogen α to cyclopropane); at 5.33 to 5.17 ppm (2-hydrogen of allyl chain and 1-hydrogen of cyclopentene).

EXAMPLE 24

(1S) 2-methyl-3-allyl-4-dichloromethylene-cyclopent-2-ene-1-yl (1R, cis) 2,2-dimethyl-3-(2,2-difluoroethenyl)-cyclopropane-1-carboxylate A solution of 7.56 g of chloroform in 36 ml of heptane was added at −20° C. over one hour to a mixture of 128 ml of heptane, 6 ml of tert.-butanol, 7.08 g of potassium tert.-butylate and 11. 1 g of triphenylphosphine and the mixture was stirred for 20 hours at −20° C. to obtain 160 ml of an ylide solution. 80 ml of the solution was held at −20° C. and a solution of 2.2 g of (1S) 2-methyl-3-allyl-4-oxo-cyclopent-2-ene-1-yl (1R, cis) 2,2-dimethyl-3-(2,2-difluoroethenyl)-cyclopropane-1-carboxylate in 15 ml of tetrahydrofuran was added under a nitrogen atmosphere with stirring at −20° C. over 20 minutes to the other 80 ml of ylide solution. The temperature was allowed to rise to 25° C. and the mixture was held at 25° C. for 6 hours. The mixture was cooled to −20° C. and then the remaining 80 ml of ylide solution were rapidly added thereto. The temperature was allowed to rise to room temperature and the mixture was stirred under an inert atmosphere for 16 hours. The mixture was filtered and the filter was washed with ether. The filtrate was added to a monosodium phosphate solution and the mixture was stirred and decanted. The aqueous phase was extracted with ether and the combined organic phases were dried over sodium sulfate and was filtered. The filtrate was evaporated to dryness under reduced pressure and the residue was empasted with ether and filtered. The filtrate was evaporated and the oil residue was chromatographed over silica gel. Elution with a 4-6 benzene-cyclohexane mixture containing 1°/oo triethylamine yielded 2 g of (1S) 2-methyl-3-allyl-4-dichloromethylenecyclopent-2-ene-1-yl (1R, cis) 2,2-dimethyl-3-(2,2-difluoroethenyl)-cyclopropane-1-carboxylate with a specific rotation of $[\alpha]_D^{20} = -28° \pm 1.5°$ (c=0.8% in benzene).

Analysis: $C_{18}H_{20}Cl_2F_2O_2$: Calculated: %C 57.30, %H 5.35, %Cl 18.8, %F 10.07; Found: 56.9, 5.4, 19.0, 10.2.

IR Spectrum (chloroform): Absorption at 1742 cm$^{-1}$ (=CF$_2$); at 1720 cm$^{-1}$ (ester carbonyl); at 1647 cm$^{-1}$ (CH$_2$=CH—); at 1603 cm$^{-1}$

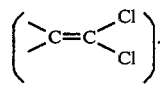

EXAMPLE 25

(1S) 2-methyl-3-allyl-4-dichloromethylene-cyclopent-2-ene-1-yl (1R, trans) 2,2-dimethyl-3-(2,2-difluoroethenyl)-cyclopropane-1-carboxylate

STEP A:
(1S)-acetoxy-2-methyl-3-allyl-4-oxo-cyclopent-2-ene 9.15 ml of triethylamine and 3.1 ml of acetic acid anhydride were added to a solution of 2 g of (1S)-hydroxy-2-methyl-3-allyl-4-oxo-cyclopentene-2-ene in 15 ml of methylene chloride and after 30 minutes of reaction, the mixture was poured into an aqueous saturated monosodium phosphate solution. The mixture was extracted with ether and the organic phase was washed with water, dried over magnesium sulfate and was filtered. The filtrate was evaporated to dryness to obtain 3.049 g of (1S)-acetoxy-2-methyl-3-allyl-4-oxocyclopent-2-ene-1-yl.

NMR Spectrum (CDCl$_3$-90 MHz): Peaks at 1.67 and 2.02 ppm (hydrogens of 2-CH$_3$ and 1-acetoxy); at 2.11 to 3.01 ppm (5-hydrogens of ring and 1-position of allyl); at 4.94 to 5.09 ppm (3-hydrogens of allyl); at 5.55 to 6 ppm (2-hydrogen of allyl).

STEP B:
(1S)-acetoxy-2-methyl-3-allyl-4-dichloromethylenecyclopent-2-ene

A solution of 75.6 g of chloroform in 60 ml of heptane was added with stirring at −20° C. over 90 minutes to a mixture of 111 g of ground triphenylphosphine, 1000 ml of heptane, 60 ml of tert.-butanol and 70.8 g of potassium tert.-butylate mixed at room temperature and the mixture was stirred at −20° C. for 5 hours and then stood at −20° C. for 16 hours to obtain an ylide solution. Part of the solution was kept under nitrogen at −20° C. and a solution of 26 g of the product of Step A in 140 ml of tetrahydrofuran was added at −20° C. under nitrogen with stirring to the balance of the ylide solution. The temperature was allowed to rise to room temperature and the mixture was stirred for 5 hours. After cooling the mixture to −20° C., the first portion of the ylide solution was added thereto under nitrogen and the temperature was allowed to rise to 20° C. The mixture was stirred under an inert atmosphere at 20° C. for 16 hours and was then filtered. The filtrate was added to an aqueous monosodium phosphate solution and the mixture was extracted with ether. The combined organic phases were dried over sodium sulfate and was filtered and the filtrate was evaporated to dryness under reduced pressure. The residue was chromatographed over silica gel and was eluted with an 8-2 benzene-ethyl acetate mixture containing 1°/oo triethylamine to obtain 14 g of (1S)-acetoxy-2-methyl-3-allyl-4-dichloromethylene-cyclopent-2-ene.

STEP C:
1S-hydroxy-2-methyl-3-allyl-4-dichloromethylenecyclopent-2-ene

A solution of 9.3 g of sodium carbonate in 195 ml of water was added with stirring to a solution of 14 g of the product of Step B in 350 ml of ethanol and after the addition of a little dioxane, the mixture was stirred for 4 days at 20° C. and was then evaporated to dryness. The residue was taken up in water and the solution was extracted with isopropyl ether. The organic phase was dried over sodium sulfate and was filtered. The filtrate was evaporated to dryness under reduced pressure to obtain 10.9 g of 1S-hydroxy-2-methyl-3-allyl-4-dichloromethylene-cyclopent-2-ene.

IR Spectrum (chloroform): Absorption at 3600–3587 cm$^{-1}$ (OH); at 1635–1600 cm$^{-1}$ (C=C).

NMR Spectrum (CDCl$_3$-60 MHz): Peaks at 1.77 to 3.17 ppm (5-hydrogens of ring); at 1.83 ppm (2-CH$_3$ of ring); at 3.27 ppm (doublet-J=7 Hz) (1-hydrogens of allyl); at 4.5 to 4.67 ppm (1-hydrogen of ring); at 4.83 to 5.25 ppm (3-hydrogens of allyl); at 5.5 to 6.33 ppm (2-hydrogen of allyl).

STEP D: (1S) 2-methyl-3-allyl-4-dichloromethylene-cyclopent-2-ene-1-yl (1R, trans) 2,2-dimethyl-3-(2,2-difluoroethenyl)cyclopropane-1-carboxylate A solution of 1.95 g of (1R, trans) 2,2-dimethyl-3-(2,2-difluoroethenyl)-cyclopropane-1-carboxylic acid chloride in 15 ml of benzene was added with stirring at 25°–30° C. to a mixture of 2.3 g of the product of Step C, 30 ml of benzene and 3 ml of pyridine and the mixture was stirred at 20° C. for 16 hours. The mixture was poured into water and the resulting mixture was extracted with isopropyl ether. The organic phase was dried over sodium sulfate and filtered and the filtrate was evaporated to dryness under reduced pressure. The residue was chromatographed over silica gel and was eluted with a 4-6 benzene-cyclohexane mixture containing 1°/oo triethylamine to obtain 2.1 g of (1S) 2-methyl-3-allyl-4-dichloromethylene-cyclopent-2-ene-1-yl (1R, trans) 2,2-dimethyl-3-(2,2-difluoromethyl)-cyclopropane-1-carboxylate with a specific rotation of $[\alpha]_D^{20} = -77.5° \pm 1.5°$ (c=1% in benzene).

Analysis: $C_{18}H_{20}F_2Cl_2O_2$: Calculated: %C 57.30, %H 5.34, %Cl 18.80, %F 10.07; Found: 57.3, 5.2, 19.8, 9.6.

IR Spectrum (chloroform): Absorption at 1745 cm$^{-1}$

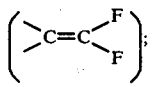

at 1720 cm$^{-1}$ (ester carbonyl); at 1638–1605 cm$^{-1}$ (C=C and conjugated C=C).

EXAMPLE 26

(1S) 2-methyl-3-allyl-4-dichloromethylene-cyclopent-2-ene-1-yl (1R, cis) 2,2-dimethyl-3-(2-fluoro-2-chloroethenyl)cyclopropane-1-carboxylate A solution of 2.1 g of (1R, cis) 2,2-dimethyl-3-(2-fluoro-2-chloroethenyl)-cyclopropane-1-carboxylic acid chloride in 10 ml of benzene was added dropwise with stirring at 25°–30° C. to a mixture of 2.3 g of (1S)-hydroxy-2-methyl-3-allyl-4-dichloromethylene-cyclopent-2-ene in 23 ml of benzene and 4 ml of pyridine and after stirring for 16 hours, the mixture was poured into water. The aqueous phase was extracted with ether and the combined organic phases were dried over sodium sulfate and filtered. The filtrate was evaporated to dryness under reduced pressure and the residue was chromatographed over silica gel. Elution with a 4-6 benzene-cyclohexane mixture containing 1°/$_{oo}$ triethylamine yielded 2.2 g of (1S) 2-methyl-3-allyl-4-dichloromethylene-cyclopent-2-ene-1-yl (1R, cis) 2,2-dimethyl-3-(2-fluoro-2-chloroethenyl)cyclopropane-1-carboxylate with a specific rotation of $[\alpha]_D^{20} = -13.5° \pm 2°$ (c=0.42% in benzene).

Analysis: $C_{18}H_{20}Cl_3FO_2$: Calculated: %C 54.91, %H 5.12, %Cl 27.01, %F 4.83; Found: 55.1, 5.2, 26.8, 4.9.

IR Spectrum (chloroform): Absorption at 1720 cm$^{-1}$ (ester carbonyl); at 1675 cm$^{-1}$ (CFCl=); at 1675–1637–1605 cm$^{-1}$ (CCl$_2$=, conjugated —C=C and C=C).

EXAMPLE 27

(1S) 2-methyl-3-allyl-4-dichloromethylene-cyclopent-2-ene-1-yl (1R, cis) 2,2-dimethyl-3-(2,2-dibromo-ethenyl)-cyclopropane-1-carboxylate A solution of 3.2 g of (1R, cis) 2,2-dimethyl-3-(2,2-dibromo-ethenyl)-cyclopropane-1-carboxylic acid chloride in 15 ml of benzene was added dropwise at 25°–30° C. to a mixture of 2.3 g of (1S)-hydroxy-2-methyl-3-allyl-4-dichloromethylene-cyclopent-2-ene in 30 ml of benzene and 3.5 ml of pyridine and the mixture was stirred at 20° C. for 16 hours and then poured into water. The decanted aqueous phase was extracted with isopropyl ether and the combined organic phases were dried over sodium sulfate and filtered. The filtrate was evaporated to dryness under reduced pressure and the residue was chromatographed over silica gel. Elution with a 4-6 benzene-cyclohexane mixture containing 2% triethylamine yielded 2.2 g of (1S) 2-methyl-3-allyl-4-dichloromethylenecyclopent-2-ene-1-yl (1R, cis) 2,2-dimethyl-3-(2,2-dibromoethenyl)-cyclopropane-1-carboxylate with a specific rotation of $[\alpha]_D^{20} = -6° \pm 2°$ (c=0.7% in benzene).

Analysis: $C_{18}H_{20}Br_2Cl_2O_2$: Calculated: %C 43.31, %H 4.04, %Cl 14.21, %Br 32.03; Found: 43.8, 4.0, 14.1, 31.8.

IR Spectrum (chloroform): Absorption at 1721 cm$^{-1}$ (ester carbonyl); at 1640–1607 cm$^{-1}$ (C=C and conjugated C=C); at 997 cm$^{-1}$ (C=CH$_2$).

EXAMPLE 28

(1S) 2-methyl-3-allyl-4-methylene-cyclopent-2-ene-1-yl (1R, trans) 2,2-dimethyl-3-(2,2-difluoro-ethenyl)-cyclopropane-1-carboxylate 3.88 g of (1R, trans) 2,2-dimethyl-3-(2,2-difluoroethenyl)-cyclopropane-1-carboxylic acid chloride were added over 5 minutes at 10° C. to a solution of 3 g of (1S)-hydroxy-2-methyl-3-allyl-4-methylene-cyclopent-2-ene in 30 ml of benzene and 9 ml of pyridine and after stirring for 4 hours at 20°–25° C., the mixturre was poured into ice water. The decanted aqueous phase was extracted with isopropyl ether and the combined organic phases were washed with water, dried over sodium sulfate and filtered. The filtrate was evaporated to dryness under reduced pressure and the residue was chromatographed over silica gel. Elution with a 6-4 cyclohexanebenzene mixture containing 1°/°° triethylamine yielded 5.6 g of pure (1S) 2-methyl-3-allyl-4-methylene-cyclopent-2-ene-1-yl (1R, trans) 2,2-dimethyl-3-(2,2-difluoro-ethenyl)-cyclopropane-1-carboxylate.

Analysis: $C_{18}H_{22}F_2O_2$ Calculated: %C 70.11, %H 7.19, %F 12.32; Found: 70.4, 7.3, 12.2.

IR Spectrum (chloroform): Absorption at 1742 cm$^{-1}$ (CF$_2$=CH—); at 1713 cm$^{-1}$ (ester carbonyl); at 1635 cm$^{-1}$ (CH$_2$=C<).

EXAMPLE 29

(1S) 2-methyl-3-allyl-4-dichlormethylene-cyclopent-2-ene-1-yl (d) α-isopropyl-α-(4-chlorophenyl)-acetate A solution of 2.3 g of (d) α-isopropyl-α-(4-chlorophenyl)-acetyl chloride in 10 ml of benzene was added dropwise with stirring at 25°–30° C. to a mixture of 2.3 g of 1S-hydroxy-2-methyl-3-allyl-4-dichloromethylene-cyclopent-2-ene in 23 ml of benzene and 4 ml of pyridine and after stirring for 16 hours at room temperature, the mixture was poured into water. The aqueous phase was extracted with isopropyl ether and the combined organic phases were dried over sodium sulfate and filtered. The filtrate was evaporated to dryness under reduced pressure and the residue was chromatographed over silica gel. Elution with a 4-6 benzene-cyclohexane mixture containing 1°/$_{oo}$ triethylamine yielded 2.7 g of (1S) 2-methyl-3-allyl-4-dichloromethylenecyclopent-2-ene-1-yl (d) α-isopropyl-α-(4-chlorophenyl)-acetate with a specific rotation of $[\alpha]_D^{20} = -105° \pm 3°$ (c=0.46% in benzene).

Analysis: $C_{21}H_{23}Cl_3O_2$: Calculated: %C 60.96, %H 5.60, %Cl 25.76; Found: 61.0, 5.6, 25.8.

IR Spectrum (chloroform): Absorption at 1728 cm$^{-1}$ (ester carbonyl); at 1638 cm$^{-1}$ (C=C); at 1604–1494 cm$^{-1}$ (conjugated C=C and aromatic ring).

EXAMPLE 30

(1S) 2-methyl-3-allyl-4-dichloromethylene-cyclopent-2-ene-1-yl (1R, cis) 2,2-dimethyl-3-(2,2-dichloroethenyl)-cyclopropane-1-carboxylate A solution of 2.2 g of (1R, cis) 2,2-dimethyl-3-(2,2-dichloroethenyl)-cyclopropane-1-carboxylic acid chloride in 5 ml of benzene was added at 20° C. to a solution of 2.3 g of 1S-hydroxy-2-methyl-3-allyl-4-dichloromethylene-cyclopent-2-ene in 30 ml of benzene and 5 ml of pyridine and after stirring at 20° C. for 16 hours, the mixture was poured into water. The aqueous phasee was extracted with ether and the combined organic phases were dried over sodium sulfate and filtered. The filtrate was evaporated to dryness under reduced pressure and the residue was chromatographed over silica gel. Elution with a 7-3 benzene-cyclohexane mixture containing 1‰ triethylamine yielded 1.9 g of (1S) 2-methyl-3-allyl-4-dichloromethylene-cyclopent-2-ene-1-yl (1R, cis) 2,2-dimethyl-3-(2,2-dichloroethenyl)-cyclopropane-1-carboxylate with a specific rotation of $[\alpha]_D^{20} = -9°$ (c=0.2% in benzene).

NMR Spectrum (CDCl$_3$-60 MHz): Peaks at 1.26–1.27 ppm (hydrogens of 2-CH$_3$ of cyclopropane); at 1.78–1.80 ppm (hydrogens of 2-CH$_3$ of cyclopentene); at 4.78–5.16 ppm (hydrogens of methylene of 3-allyl of cyclopentene); at 5.47–5.58 ppm (1-hydrogen of cyclopentene); at 5.50–6.33 ppm (2-hydrogen of allyl of cyclopentene); at 6.20–6.33 ppm (1-hydrogen of 3-vinyl of cyclopropyl).

EXAMPLE 31

(1S) 2-methyl-3-allyl-4-methylene-cyclopent-2-ene-1-yl (1R,cis) 2,2-dimethyl-3-[(E) 3-oxo-1-butenyl]-cyclopropane-1-carboxylate STEP A: Acetonylidene triphenylphosphorane A solution of 55 g of triphenylphosphine, 15.5 ml of chloroacetone and 165 ml of chloroform was refluxed for 45 minutes and after cooling to 20° C., the mixture was poured into 1.65 liters of ether. The mixture was vacuum filtered and the recovered product was washed with ether and dried under reduced pressure to obtain 26.9 g of acetonyltriphenylphosphonium chloride. The said product was added to 270 ml of aqueous 10% sodium carbonate solution and the mixture was stirred for 16 hours and was vacuum filtered. The product was washed with water and dried under reduced pressure to obtain 20.3 g of raw product which was crystallized from 50% aqueous methanol to obtain 16 g of acetonylidene triphenylphosphorane melting at 207°–208° C.

| UV Spectrum (ethanol): | | |
|---|---|---|
| Inflex. towards 220 nm | $E_1^1 = 906$ | |
| Max. towards 260 nm | $E_1^1 = 201$ | $\epsilon = 6400$ |
| Max. towards 267 nm | $E_1^1 = 209$ | $\epsilon = 6650$ |
| Max. towards 274 nm | $E_1^1 = 205$ | $\epsilon = 6500$ |
| Inflex. towards 283 nm | $E_1^1 = 179$ | |

STEP B: (1R, cis) 2,2-dimethyl-3-[(E)-3-oxo-1-butenyl]-cyclopropane-carboxylic acid A mixture of 14.21 g of the lactone of cis, 2,2-dimethyl-3S-(dihydroxymethyl)-cyclopropane-1R-carboxylic acid, 63.7 g of acetonylidene triphenylphosphorane, 100 ml of monoglyme and 1200 ml of benzene was refluxed for 4 hours, cooled to room temperature and evaporated to dryness. The oil residue was taken up in 200 ml of 1 N sodium hydroxide solution and 400 ml of methylene chloride and after stirring, the decanted aqueous phase was washed with methylene chloride. Concentrated hydrochloric acid was added to the aqueous phases to adjust the pH 1 and the mixture was extracted with ether. The ether phase was washed with water, dried and evaporated to dryness to obtain 13.5 g of product which was crystallized from isopropyl ether to obtain 10.95 g of (1R, cis) 2,2-dimethyl-3-[(E)-3-oxo-1-butenyl]-cyclopropane-carboxylic acid melting at 120° C. and having a specific rotation of $[\alpha]_D^{20} = -35.5° \pm 2°$ (c=0.6% in benzene).

IR Spectrum (chloroform): Absorption at 3500 cm$^{-1}$ (OH); at 1750 and 1755 cm$^{-1}$ (carbonyl); at 1665 cm$^{-1}$ (ketone); at 1612 and 980 cm$^{-1}$ (C=C).

STEP C: (1R, cis) 2,2-dimethyl-3-[(E)-3-oxo-1-butenyl]-cyclopropane-carboxylic acid chloride 2 ml of thionyl chloride were added at 5° to 7° C. to a solution of 3 g of the acid of Step B in 15 ml of methylene chloride and 15 ml of isoprene and the mixture was stirred at 5° C. for 15 minutes and at 20° C. for 3 hours. The mixture was evaporated to dryness under reduced pressure and the residue was dissolved in benzene. The solution was evaporated to dryness to obtain 3.3 g of raw (1R, cis) 2,2-dimethyl-3-[(E)-3-oxo-1-butenyl]-cyclopropane-carboxylic acid chloride which was used as is for the next step.

STEP D: (1S) 2-methyl-3-allyl-4-methylene-cyclopent-2-ene-1-yl (1R, cis) 2,2-dimethyl-3-[(E)-3-oxo-1-butenyl]-cyclopropane-carboxylate 1.5 ml of pyridine were added at 5° C. to a mixture of 3.3 g of the product of Step C, 2.71 g of 1S-hydroxy-2-methyl-3-allyl-4-methylene-cyclopent-2-ene and 50 ml of benzene and the mixture was stirred at 5° C. for 15 minutes and at 20° C. for 2 hours. The mixture was poured into 20 ml of 2 N hydrochloric acid and 100 ml of water at 5° C. and the decanted aqueous phase was extracted with ether. The organic phase was washed with water, dried and evaporated to dryness. The 7 g of residue were chromatographed over silica gel and were eluted with a 95-5 cyclohexane-ethyl acetate mixture containing 2‰ triethylamine to obtain 1.75 g of (1S) 2-methyl-3-allyl-4-methylene cyclopent-2-ene-1-yl (1R, cis) 2,2-dimethyl-3-[(E)-3-oxo-butenyl]-cyclopropane-carboxylate with a specific rotation of $[\alpha]_D^{20} = -47° \pm 2°$ (c=0.5% in benzene).

Analysis: C$_{20}$H$_{26}$O$_3$: molecular weight=314.42, Calculated: %C 76.4, %H 8.33; Found: 76.1, 8.3.

NMR Spectrum (CDCl$_3$-60 MHz): Peaks at 2.25 ppm (4-hydrogens of butenyl); at 6.05 to 6.32 ppm (2-hydrogen of butenyl); at 6.09 to 7.5 ppm (1-hydrogen of butenyl); at 1.25 to 1.37 ppm (hydrogens of 2-CH$_3$ of cyclopropane); at 2.5 to 5.75 ppm (1-hydrogen of cyclopentyl); at 1.77 ppm (hydrogens of 2-methylene of cyclopentyl ring); at 5.48 to 6.13 ppm (2-hydrogen of allyl); at 4.75 to 5.25 ppm (3-hydrogens of allyl and hydrogens of 4-methylene).

EXAMPLE 32

(1S) 2-methyl-3-allyl-4-methylene-cyclopent-2-ene-1-yl (1R, trans) 2,2-dimethyl-3[(E)-3-oxo-1-butenyl]-cyclopropane-1-carboxylate

STEP A: (1R, trans) 2,2-dimethyl-3-[(E)-3-oxo-1-butenyl]-cyclopropane-carboxylic acid A mixture of 10.66 g of (1R, trans) 2,2-dimethyl-3-formyl-cyclopropane-1-carboxylic acid, 47.76 g of acetonylidenetriphenylphosphorane, 600 ml of benzene and 60 ml of monoglyme was refluxed for 4 hours and was then evaporated to dryness. The residue was taken up in 200 ml of 1 N sodium hydroxide solution and 400 ml of methylene chloride and the mixture was energetically stirred and decanted. The aqueous phase was adjusted to a pH of 1 by addition of concentrated hydrochloric acid and was extracted with ether. The ether phase was dried and evaporated to dryness to obtain 13 g of product which was crystallized from toluene to obtain 10.28 g of (1R, trans) 2,2-dimethyl-3-[(E)-3-oxo-1-butenyl]-cyclopropane-carboxylic acid melting at 130° C. and having a specific rotation of $[\alpha]_D^{20} = +112.5° \pm 3°$ (c=0.4% in benzene).

IR Spectrum (chloroform): Absorption at 3500 cm$^{-1}$ (OH); at 1739 cm$^{-1}$ and 1695 cm$^{-1}$ (acid carbonyl); at 1657 cm$^{-1}$ (ketone); at 1614 cm$^{-1}$ and 975 cm$^{-1}$ (C=C).

STEP B: (1R, trans) 2,2-dimethyl-3-[(E)-3-oxo-1-butenyl]-cyclopropane-carboxylic acid chloride A mixture of 4 g of the product of Step A, 20 ml of isoprene and 3 ml of thionyl chloride was stirred at 20° C. for 5 hours and was then evaporated to dryness under reduced pressure to form raw (1R, trans) 2,2-dimethyl-3-[(E)-3-oxo-1-butenyl]-cyclopropane-carboxylic acid chloride which was used as is for the next step.

STEP C 5 ml of pyridine were added to a solution of 3.29 g of 1S-hydroxy-2-methyl-3-allyl-4-methylene-cyclopent-2-ene in 20 ml of benzene and after stirring at 20° C., a solution of the product of Step B in 20 ml of benzene was added thereto over 15 minutes. The mixture was stirred for 17 hours at 20° C. and was then poured into water. The aqueous phase was extracted with methylene chloride and the combined organic phases were dried and evaporated to dryness to obtain 12.7 g of residue which was chromatographed over silica gel. Elution while a 9-1 cyclohexane-ethyl acetate mixture containing 1°/$_{oo}$ triethylamine yielded 3.39 g of (1S) 2-methyl-3-allyl-4-methylene-cyclopent-2-ene-1-yl (1R, trans) 2,2-dimethyl-3-[(E)-3-oxo-1-butenyl]-cyclopropane-1-carboxylate Analysis: C$_{20}$H$_{26}$O$_3$: molecular weight=314.43, Calculated: %C 76.39, %H 8.34, Found: 76.6, 8.6.

IR Spectrum (CDCl$_3$-60 MHz): Peaks at 2.2 ppm (4-hydrogens of butenyl); at 6.08 to 6.35 ppm (2-hydrogen of butenyl); at 6.37 to 6.5 ppm and 6.63 to 6.76 ppm (1-hydrogen of butenyl); at 1.25 to 1.3 ppm (hydrogens and methyls of 2-position of cyclopropane ring); at 4.67 to 6.08 ppm (1-hydrogen of cyclopentyl); at 1.78 ppm (hydrogens of 2-CH$_3$ of cyclopentyl ring).

EXAMPLE 33

(1S) 2-methyl-3-allyl-4-methylene-cyclopent-2-ene-1-yl (1R, trans) 2,2-dimethyl-3-[2-methoxycarbonyl-(E)-ethenyl]-cyclopropane-carboxylate

STEP A: Triphenyl acetate of methylphosphonium bromide 76.5 g of methyl bromoacetate were added at 20° C. to a mixture of 131.14 g of triphenylphosphine and 600 ml of benzene and the mixture was stirred at 20° C. for 90 minutes and then at 10° C. for 2 hours. The mixture was filtered and the product was washed with benzene and then with petroleum ether and dried under reduced pressure to obtain 135.8 g of triphenyl acetate of methylphosphonium bromide melting at 200° C.

STEP B: (1R, trans) 2,2-dimethyl-3-[2-methoxycarbonyl-(E)-ethenyl]-cyclopropane-carboxylic acid 75.95 g of the product of Step A were added at 20° C. with stirring to a mixture of 7.19 g of sodium hydride as a 60% suspension in mineral oil and 200 ml of tetrahydrofuran and the mixture was stirred at 20° C. for 3 hours and was then cooled to 0° C. A solution of 20 g of (1R, trans) 2,2-dimethyl-3-formyl-cyclopropane-carboxylic acid in 100 ml of tetrahydrofuran was added to the mixture which was stirred at 0° C. for 2½ hours. After the temperature rose to 20° C., the mixture was stirred for 16 hours and was then poured into a mixture of 20 ml of concentrated hydrochloric acid and ice. The mixture was extracted with methylene chloride and the organic phase was washed with water, dried and evaporated to dryness. The 63.3 g of residue was chromatographed over silica gel and was eluted with an 8-2 benzene-ethyl acetate mixture containing 1°/$_{oo}$ acetic acid to obtain 22.51 g of (1R, trans) 2,2-dimethyl-3-[2-methoxycarbonyl-(E)-ethenyl]-cyclopropane-carboxylic acid with a specific rotation of $[\alpha]_D^{20} = +107° \pm 2°$ (c=0.88% in chloroform).

STEP C: (1R, trans) 2,2-dimethyl-3-[2-methoxycarbonyl-(E)-ethenyl]-cyclopropane-carboxylic acid chloride A mixture of 4 g of the product of Step A, 20 ml of isoprene and 3 ml of thionyl chloride was stirred at 20° C. for 5 hours and was evaporated to dryness under reduced pressure to obtain raw (1R, trans) 2,2-dimethyl-3-[2-methoxycarbonyl-(E)-ethenyl]-cyclopropane-carboxylic acid chloride which was used as is for the next step.

STEP D: (1S) 2-methyl-3-allyl-4-methylene-cyclopent-2-ene-1-yl (1R, trans) 2,2-dimethyl-3-[2-methoxycarbonyl-(E)-ethenyl]-cyclopropane-carboxylate 4 ml of pyridine were added to a solution of 3.03 g of 1S-hydroxy-2-methyl-3-allyl-4-methylene-cyclopent-2-ene in 20 ml of benzene and the solution was stirred at 20° C. while a solution of the product of Step C in 15 ml of benzene was added over 15 minutes. The mixture was stirred for 17 hours at 20° C. and was then poured into water. The mixture was extracted with methylene chloride and the organic phase was dried and evaporated to dryness. The 9.6 g of residue was chromatographed over silica gel and was eluted with a 9-1 cyclohexane-ethyl acetate mixture containing 1°/₀₀ triethylamine to obtain 3.08 g of (1S) 2-methyl-3-allyl-4-methylenecyclopent-2-ene-1-yl (1R, trans) 2,2-dimethyl-3-[2-methoxycarbonyl-(E)-ethenyl]-cyclopropane-carboxylate with a specific rotation of $[\alpha]_D^{20} = -20.5° \pm 1.5°$ (c=0.8% in chloroform).

NMR Spectrum (CDCl₃-60 MHz): Peaks at 3.73 ppm (hydrogens of CH₃O—); at 5.82 to 6.08 ppm (2-hydrogen of ethenyl); at 6.46 to 6.63 ppm and 6.73 to 6.9 ppm (1-hydrogen of ethenyl); at 1.23 to 1.28 ppm (hydrogens of 2-CH₃ of cyclopropane ring); at 1.77 ppm (hydrogens of 2-CH₃ of cyclopentyl); at 4.67 to 6.08 ppm (other hydrogens of substituents on cyclopentyl ring and 1-hydrogen of cyclopentyl ring).

EXAMPLE 34

(1S) 2-methyl-3-allyl-4-methylene-cyclopent-2-ene-1-yl
(1R, cis)
2,2-dimethyl-3-[2-methoxycarbonyl-(Z)-ethenyl]-cyclopropane-carboxylate

STEP A: (1R, cis) 2,2-dimethyl-3-[2-methoxycarbonyl-(E) and (Z)-ethenyl]-cyclopropane-carboxylic acid 116.8 g of triphenyl acetate of methylphosphonium bromide were added to a mixture of 11.15 g of sodium hydride as a 60% suspension in mineral oil and 300 ml of tetrahydrofuran and the suspension was stirred at 20° C. for 3 hours and then was cooled to 0° C. A solution of 20 g of the lactone of cis 2,2-dimethyl-3S-(dihydroxymethyl)-cyclopropane-carboxylic acid in 100 ml of tetrahydrofuran was added thereto over one hour. The mixture was stirred at 0° C. for 2 hours and then at 20° C. for 16 hours and was then poured into a mixture of 30 ml of concentrated hydrochloric acid and ice. The mixture was extracted with methylene chloride and the decanted organic phase was washed with water, dried and evaporated to dryness to obtain 82.2 g of residue. The latter was chromatographed over silica gel and was eluted with a 6-4 benzene-ethyl acetate mixture containing 1°/₀₀ acetic acid to obtain 2 g of the desired Z isomer with a specific rotation of $[\alpha]_D^{20} = +75.5° \pm 2°$ (c=1% in chloroform) and 6.5 g of the corresponding E isomer with a specific rotation of $[\alpha]_D^{20} = +9.5° \pm 1°$ (c=1% in chloroform).

IR Spectrum (chloroform)-Z isomer: Absorption at 1712 cm⁻¹ and 1695 cm⁻¹ (carbonyl); at 1637 cm⁻¹ and towards 1625 cm⁻¹ (C=C); at 980 cm⁻¹.

IR Spectrum (chloroform)-E isomer: Absorption at 1700 cm⁻¹ and 1710 cm⁻¹ (carbonyl); at 1647 cm⁻¹ and towards 1635 cm⁻¹ (C=C); at 980 cm⁻¹ (E double bond).

STEP B: (1R, cis) 2,2-dimethyl-3-[2-methoxycarbonyl-(Z)-ethenyl]-cyclopropane-carboxylic acid chloride A mixture of 1.8 g of the Z isomer of Step A, 10 ml of isoprene and 1 ml of thionyl chloride was stirred at 0° C. for 30 minutes and at 20° C. for 4 hours and was then evaporated to dryness under reduced pressure to obtain raw (1R, cis) 2,2-dimethyl-3-[2-methoxycarbonyl-(Z)-ethenyl]-cyclopropanecarboxylic acid chloride which was used as is for the next step.

STEP C: (1S) 2-methyl-3-allyl-4-methylene-cyclopent-2-ene-1-yl (1R, cis) 2,2-dimethyl-3-[2-methoxycarbonyl-(Z)-ethenyl]-cyclopropane-carboxylate 0.486 g of pyridine were added to a solution of 0.9 g of 1S-hydroxy-2-methyl-3-allyl-4-methylene-cyclopent-2-ene in 5 ml of benzene and a solution of 1.08 g of the product of Step B in 10 ml of benzene was added thereto with stirring at 10° C. The mixture was stirred at 20° C. for 16 hours and was then poured into water. The decanted organic phase was washed with water and the wash water was reextracted with benzene. The combined organic phases were dried and evaporated to dryness under reduced pressure. The 2.2 g of residue was chromatographed over silica gel and was eluted with benzene containing 1°/₀₀ triethylamine to obtain 0.54 g of (1S) 2-methyl-3-allyl-4-methylene-cyclopent-2-ene-1-yl (1R, cis) 2,2-dimethyl-3-[2-methoxycarbonyl-(Z)-ethenyl]-cyclopropanecarboxylate with a specific rotation of $[\alpha]_D^{20} = +45° \pm 1.5°$ (c=0.9% in chloroform).

Analysis: C₂₀H₂₆O₄; molecular weight=330.428, Calculated: %C 72.70, %H 7.93; Found: 72.8, 7.6.

NMR Spectrum (CDCl₃-60 MHz): Peaks at 3.75 ppm (hydrogens of CH₃O—); at 6.52 to 6.68 ppm and 6.71 to 6.86 ppm (1-hydrogen of ethenyl); at 5.83 to 6.02 ppm (2-hydrogen of ethenyl); at 1.27 to 1.32 ppm (hydrogens of 2-CH₃ of cyclopropane); at 5.5 to 5.83 ppm (1-hydrogen of cyclopentyl ring); at 1.78 ppm (hydrogens of 2-CH₃ of cyclopentyl ring); at 2.95 to 3.07 ppm (2-hydrogens of allyl); at 4.75 to 5.17 ppm (hydrogens of =CH₂ and 3-hydrogens of allyl).

EXAMPLE 35

(1S) 2-methyl-3-allyl-4-methylene-cyclopent-2-ene-1-yl
(1R, cis)
2,2-dimethyl-3-[2-methoxycarbonyl-(E)-ethenyl]-cyclopropane-carboxylate

STEP A: (1R, cis) 2,2-dimethyl-3-[2-methoxycarbonyl-(E)-ethenyl]-cyclopropane-carboxylic acid chloride 1.8 g of the E isomer of the acid of Step B of Example 34, 10 ml of isoprene and 1 ml of thionyl chloride was stirred at 0° C. for 30 minutes and at 20° C. for 4 hours and was then evaporated to dryness under reduced pressure to obtain raw (1R, cis) 2,2-dimethyl-3-[2-methoxycarbonyl-(E)-ethenyl]-cyclopropane-carboxylic acid chloride which was used as is for the next step.

STEP B: (1S) 2-methyl-3-allyl-4-methylene-cyclopent-2-ene-1-yl (1R, cis) 2,2-dimethyl-3-[2-methoxycarbonyl-(E)-ethenyl]-cyclopropane-carboxylate A solution of 1.65 g of the product of Step A in benzene was added at 0° C. over 15 minutes to a mixture of 1.36 g of 1S-hydroxy-2-methyl-3-allyl-4-cyclopent-2-ene, 10 ml of benzene and 0.7 ml of pyridine and the mixture was stirred at 20° C. for 16 hours and was then poured into water. The decanted organic phase was washed with water, dried and evaporated to dryness. The 3.2 g of residue were chromatographed over silica gel and were eluted with a 95-5 benzene-ethyl acetate mixture containing 1°/₀₀ triethylamine to obtain 0.564 g of (1S) 2-methyl-3-allyl-4-methylene-cyclopent-2-ene-1-yl (1R, cis) 2,2-dimethyl-3-[2-methoxycarbonyl-(E)- ethenyl]-cyclopropane-carboxylate with a specific rotation of $[\alpha]_D^{20} = -40° \pm 2.5°$ (c=0.5% in chloroform).

Analysis: $C_{20}H_{26}O_4$: Calculated: %C 72.70, %H 7.93; Found: 72.5, 8.2.

NMR Spectrum (CDCl$_3$-60 MHz): Peaks at 3.73 ppm (hydrogens of CH$_3$O—); at 5.83 to 6.1 ppm (2-hydrogen of ethenyl); at 7.08 at 7.58 ppm (1-hydrogen of ethenyl); at 1.23 to 1.36 ppm (hydrogen of 2-CH$_3$ of cyclopropane ring); at 5.58 ppm (1-hydrogen of cyclopentyl ring); at 1.77 ppm (hydrogens of 2-CH$_3$ of cyclopentyl ring); at 4.75 to 5.25 ppm (hydrogen of CH$_2$= and 3-hydrogens of allyl).

EXAMPLE 36

(1S) 2-methyl-3-allyl-4-methylene-cyclopent-2-ene-1-yl (1R, trans) 2,2-dimethyl-3-ethenyl-cyclopropane-carboxylate

STEP A: (1R, trans) 2,2-dimethyl-3-ethenyl-cyclopropane-carboxylic acid

A solution of 115 g of potassium tert.-butylate in 200 ml of dimethylformamide was added at −60° C. to a mixture of 70 g of (1R, trans) 2,2-dimethyl-3-formyl-cyclopropane carboxylic acid in 500 ml of dimethylformamide and 210 g of triphenylmethylphosphonium bromide and the temperature was then allowed to rise to 10° C. The suspension was poured into iced water and was acidified and extracted with benzene. The organic phase was dried and evaporated to dryness to obtain 62.2 g of (1R, trans) 2,2-dimethyl-3-ethenyl-cyclopropane-carboxylic acid which was used as is for the next step.

STEP B: (1S) 2-methyl-3-allyl-4-methylene-cyclopent-2-ene-1-yl (1R, trans) 2,2-dimethyl-3-ethenyl-cyclopropane-carboxylate 4.4 g of dicyclohexylcarbodiimide were added with stirring at 0° C. to a mixture of 3 g of 1S-hydroxy-2-methyl-3-allyl-4-methylene-cyclopent-2-ene, 100 ml of methylene chloride, 3 g of the product of Step A and 0.3 g of 4-dimethylamino-pyridine and the mixture was stirred at 0° C. for 10 minutes. The temperature was allowed to rise to 20° C. and the mixture was stirred at 20° C. for 3 hours and was filtered. The filtrate was washed with water, dried and evaporated to dryness and the 5.6 g of residue were chromatographed over silica gel. Elution with benzene containing 1‰ triethylamine yielded 4.5 g of (1S) 2-methyl-3-allyl-4-methylene-cyclopent-2-ene-1-yl (1R, trans) 2,2-dimethyl-3-ethenyl-cyclopropane-carboxylate with a specific rotation of $[\alpha]_D^{20} = -72.5° \pm 2.5°$.

Analysis: $C_{18}H_{24}O_2$; molecular weight=272.37, Calculated: %C 79.37, %H 8.88; Found: 79.4 9.0.

IR Spectrum (chloroform): Absorption at 1713 cm$^{-1}$ (ester carbonyl); at 1656 cm$^{-1}$ (conjugated system); at 1389 cm$^{-1}$ and 1379 cm$^{-1}$ (gem dimethyl); at 985 and 914 cm$^{-1}$ (vinyl); at 866 cm$^{-1}$ (conjugated double bond).

EXAMPLE 37

(1S) 2-methyl-3-allyl-4-methylene-cyclopent-2-ene-1-yl (1R, cis) 2,2-dimethyl-3-ethenyl-cyclopropane-carboxylate

STEP A: (1R, cis) 2,2-dimethyl-3-ethenyl-cyclopropane-carboxylic acid

A mixture of 5 g of the lactone of 2,2-dimethyl-3S-(dihydroxymethyl)-cyclopropane-1R-carboxylic acid, 15 g of triphenylmethylphosphonium bromide and 40 ml of dimethylformamide at 20° C. was cooled to −60° C. and a solution of 8.2 g of potassium tert.-butylate in 10 ml of dimethylformamide was added thereto over one hour. The temperature was allowed to rise towards 0° C. over about 90 minutes and the mixture was poured into an ice-water mixture. The mixture was washed with methylene chloride and was adjusted to a pH of 1 by addition of hydrochloric acid. The aqueous phase was extracted with benzene and the benzene phase was washed with water, dried and evaporated to dryness to obtain 4.9 g of (1R, cis) 2,2-dimethyl-3-ethenyl-cyclopropane-carboxylic acid.

STEP B: (1S) 2-methyl-3-allyl-4-methylene-cyclopent-2-ene-1-yl (1R, cis) 2,2-dimethyl-3-ethenyl-cyclopropane-carboxylate Using the procedure of Step B of Example 36, 3 g of 1S-hydroxy-2-methyl-3-allyl-4-methylene-cyclopent-2-ene and 3 g of the product of Step A were reacted and after chromatography over silica gel with benzene containing 1‰ triethylamine as the eluant, 2.063 g of (1S) 2-methyl-3-allyl-4-methylene-cyclopent-2-ene-1-yl (1R, cis) 2,2-dimethyl-3-ethenyl-cyclopropane-carboxylate with a specific rotation of $[\alpha]_D^{20} = -31.5° \pm 2°$ (c=0.7% in chloroform) were obtained.

Analysis: $C_{18}H_{24}O_2$: Calculated: %C 79.37, %H 8.88; Found: 79.2, 8.8.

IR Spectrum (chloroform): Absorption at 1711 cm$^{-1}$ (ester carbonyl); at 1630 cm$^{-1}$ (conjugated C=C); at 1387 and 1376 cm$^{-1}$ (gem dimethyl); at 990-910 cm$^{-1}$ (vinyl deformation).

NMR Spectrum (CDCl$_3$-60 MHz): Peaks at 1.18 to 1.3 ppm (hydrogens of 2-CH$_3$ of cyclopropane); at 4.75 to 6.5 ppm (hydrogens of ethenyl); at 5.58 ppm (1-hydrogen of cyclopentyl ring); at 1.75 ppm (hydrogen of 2-CH$_3$ of cyclopentyl ring); at 2.93 to 3.03 ppm (1-hydrogens of allyl); 4.75 to 6.5 ppm (3-hydrogens of allyl and of methylene).

EXAMPLE 38

1S 2-methyl-3-allyl-4-methylene-cyclopent-2-ene-1-yl (1R, trans) 2,2-dimethyl-3-(2-fluoro-2-chloro-ethenyl)-cyclopropane-carboxylate Using the procedure of Step B of Example 36, 3.9 g of (1R, trans) 2,2-dimethyl-3-(2-fluoro-2-chloro-ethenyl)-cyclopropane-carboxylic acid [Brown, Structure Activity Studies of halopyrethroids, 1974, p. 27, North Texas State University] and 3.04 g of 1S-hydroxy-2-methyl-3-allyl-4-methylene-cyclopent-2-ene were reacted to obtain after chromatography over silica gel and elution with a 97-3 petroleum ether (b.p.=40°-70° C.)-ether mixture containing 1‰ triethylamine. 2.08 g of (1S) 2-methyl-3-allyl-4-methylene-cyclopent-2-ene-1-yl (1R, trans) 2,2-dimethyl-3-(2-fluoro-2-chloroethenyl)-cyclopropane-carboxylate with a specific rotation of $[\alpha]_D^{20} = -56° \pm 2.5°$ (c=1% in chloroform).

IR Spectrum (chloroform): Absorptions at 1713 cm$^{-1}$ (ester carbonyl); at 1670 and 1982 cm$^{-1}$ (conjugated system); at 1390 and 1379 cm$^{-1}$ (gem dimethyl); at 990 and 916 cm$^{-1}$ (vinyl deformation).

NMR Spectrum (CDCl$_3$-60 MHz): Peaks at 4.38 to 4.52 ppm and 4.75 to 5.25 ppm (1-hydrogen of ethenyl); at 1.48 to 1.57 ppm and 1.51 to 1.6 ppm (1-hydrogen of cyclopropane ring); at 5.58 ppm (1-hydrogen of cyclopentyl ring); at 1.78 ppm (hydrogens of 2-CH$_3$ of cyclopentyl); at 5.5 to 6.17 ppm (2-hydrogens of allyl); at 4.75 to 5.25 ppm (3-hydrogens of allyl and hydrogens of CH$_2$=).

EXAMPLE 39

(1S) 2-methyl-3-allyl-4-methylene-cyclopent-2-ene-1-yl (1R, trans) 2,2-dimethyl-3-cyclobutylidenemethyl)-cyclopropane-carboxylate 7.5 g of (1R, trans) 2,2-dimethyl-3-cyclobutylidenemethyl-cyclopropane-carboxylic acid chloride (described in French patent of addition No. 93,112) were added at 10° C. over 30 minutes to a mixture of 6 g of 1S-hydroxy-2-methyl-3-allyl-4-methylene-cyclopent-2-ene, 6 ml of benzene and 4 ml of pyridine and the mixture was stirred at 20° C. for 17 hours and was then poured into water. The mixture was extracted with methylene chloride and the organic phase was dried and evaporated to dryness. The 12.8 g of residue were chromatographed over silica gel and were eluted with a 95-5 cyclohexane-ethyl acetate mixture containing 1°/$_{oo}$ triethylamine to obtain 3.63 g of (1S) 2-methyl-3-allyl-4-methylene-cyclopent-2-ene-1-yl (1R, trans) 2,2-dimethyl-3-cyclobutylidenemethyl)-cyclopropane-carboxylate with a specific rotation of $[\alpha]_D^{20} = -76.5° \pm 2.5°$ (c=0.7% in chloroform).

Analysis: C$_{21}$H$_{28}$O$_2$: Calculated: %C 80.73, %H 9.03; Found: 80.5, 9.0.

NMR Spectrum (CDCl$_3$-60 MHz): Peaks at 1.38 to 1.47 ppm (1-hydrogen of cyclopropanering); at 1.13 to 1.25 ppm (hydrogens of 2-methyls of cyclopropane ring); at 1.78 ppm (hydrogens of 2-CH$_3$ of cyclopentyl ring); at 5.48 to 6.17 ppm (2-hydrogens of allyl and 1-hydrogen of cyclopentyl); at 4.67 to 5.17 ppm (3-hydrogens of allyl, hydrogens of methylene and hydrogen of butylidene double bond).

IR Spectrum (chloroform): Absorption at 1709 cm$^{-1}$ (ester carbonyl); at 1630 cm$^{-1}$ (conjugated double bond); at 1377 cm$^{-1}$ (gem dimethyl); at 988 and 915 cm$^{-1}$ (CH=CH$_2$ deformation).

EXAMPLE 40

(1S) 2-methyl-3-allyl-4-methylene-cyclopent-2-ene-1-yl (1R, trans) 2,2-dimethyl-3-[2-(E) and (Z)-cyanoethenyl]-cyclopropane-1-carboxylate STEP A: (1R, trans) 2,2-dimethyl-3-[(E) and (Z)-cyanoethenyl]-cyclopropane-carboxylic acid A solution of 31.9 g of diethyl cyanomethylphosphonate in 45 ml of glyme was added at 20° C. over 30 minutes to a mixture of 8.64 g of sodium hydride as a 50% suspension in mineral oil and 150 ml of glyme and the mixture was stirred at 20° C. for one hour and was then cooled to −15° C. A solution of 13 g of (1R, trans) 2,2-dimethyl-3-formyl-cyclopropane-carboxylic acid in 70 ml of glyme were added at −15° C. to the mixture at the mixture was stirred at 0° C. for one hour and at 20° C. for 3 hours. The mixture was evaporated to dryness and the residue was cooled and added to 100 ml of 1 N sodium hydroxide solution. The suspension was washed with methylene chloride and was acidified by addition of about 11 ml of concentrated hydrochloric acid. The mixture was extracted with methylene chloride and the organic phase was dried and evaporated to dryness to obtain 14.5 g of residue which were chromatographed over silica gel. Elution with a 6-4 benzene-ethyl acetate mixture containing 1°/$_{oo}$ acetic acid helded 14 g of (1R, trans) 2,2-dimethyl-3-[(E) and (Z)-cyanoethenyl]-cyclopropane-carboxylic acid.

STEP B: (1R, trans) 2,2-dimethyl-3-[2-(E) and (Z)-cyanoethenyl]-cyclopropane-carboxylic acid chloride A mixture of 14 g of the product of Step A, 70 ml of petroleum ether (b.p.=60°-80° C.) and 28 ml of thionyl chloride was refluxed for 4 hours and then was evaporated to dryness to obtain 16 g of (1R, trans) 2,2-dimethyl-3-[2-(E) and (Z)-cyanoethenyl]-cyclopropane-carboxylic acid chloride which was used as is for the next step.

STEP C: (1S) 2-methyl-3-allyl-4-methylene-cyclopent-2-ene-1-yl (1R, trans) 2,2-dimethyl-3-[2-(Z) and (E)-cyanoethenyl]-cyclopropane-carboxylate Using the procedure of Step B of Example 39, 9.4 g of (1S)-hydroxy-2-methyl-3-allyl-4-methylene-cyclopent-2-ene and 10.9 g of the product of Step B were reacted to obtain after chromatography over silica gel and elution with a 9-1 cyclohexane-ethyl acetate mixture containing 1°/$_{oo}$ triethylamine 2.2 g of the (E) isomer of the desired ester with a specific rotation of $[\alpha]_D^{20} = -15° \pm 2°$ (c=0.7% in benzene) and 2 g of the (Z) isomer of the desired ester with a melting point ∼94° C. and a specific rotation of $[\alpha]_D^{20} = -94° \pm 3°$ (c=0.5% in benzene).

Analysis: E isomer -C$_{19}$H$_{23}$NO$_2$, Calculated: %C 76.73, %H 7.80, %N 4.71; Found: 76.8, 7.7, 4.5.

NMR Spectrum (CDCl$_3$-60 MHz): Peaks at 3.18 to 5.27 ppm (2-hydrogen of ethenyl); at 6.15 to 6.32 ppm and 6.42 to 6.58 ppm (1-hydrogen of ethenyl); at 1.22 to 1.28 ppm (hydrogens of 2-CH$_3$ of cyclopropane ring); at 5.58 ppm (1-hydrogen of cyclopentyl ring); at 1.78 ppm (hydrogens of 2-CH$_3$ of cyclopentyl ring); at 2.93 to 3.03 ppm (1-hydrogens of allyl); at 5.5 to 6.16 ppm (2-hydrogen of allyl); at 4.75 to 5.17 ppm (3-hydrogens of allyl and hydrogens of methylene).

Analysis: Z-isomer—C$_{19}$H$_{23}$NO$_2$; Calculated: %C 76.73, %H 7.80, %N 4.71; Found: 76.2, 7.8, 4.5, NMR Spectrum (CDCl$_3$—60 MHz): Peaks at 5.23 to 5.42 ppm (2-hydrogen of ethenyl); at 3.92 to 6.08 ppm and 6.1 to 6.27 ppm (1-hydrogen of ethenyl); at 1.27 and 1.34 ppm (hydrogen of 2-CH$_3$ of cyclopropane ring); at 5.58 ppm (1-hydrogen of cyclopentyl ring); at 1.78 ppm (1-hydrogen of 2-CH$_3$ of cyclopentyl ring); at 2.93 to 3.03 ppm (1-hydrogens of allyl); at 5.42 to 6.25 ppm (1-hydrogen of allyl); at 4.75 to 5.25 ppm (3-hydrogens of allyl and hydrogens of methylene).

EXAMPLE 41

(1R) 2-methyl-3-allyl-4-methylene-cyclopent-2-ene-1-yl (1R, trans) 2,2-dimethyl 3-[2-methyl-1-propenyl]-cyclopropane carboxylate Using the procedure of Example 1, 2.6 g of (1R, trans) 2,2-dimethyl-3-(2-methyl-1-propenyl)-cyclopropane-carboxylic acid chloride and 2 g of 1R-hydroxy-2-methyl-3-allyl-4-methylene-cyclopent-2-ene were reacted to obtain after chromatography over silica gel and elution with a 95-5 cyclohexane-ethyl acetate mixture containing 1°/$_{oo}$ triethylamine 1.532 g of (1R) 2-methyl-3-allyl-4-methylene-cyclopent-2-1-yl (1R, trans) 2,2-dimethyl 3-[2-methyl-1-propenyl]-cyclopropane-carboxylate.

NMR Spectrum (CDCl$_3$—60 MHz): Peaks at 1.12 to 1.27 ppm (hydrogens of 2-CH$_3$ of cyclopropane ring); at 1.69 to 1.77 ppm (hydrogens of 2-CH$_3$ of cyclopentyl ring); at 1.33 to 1.42 ppm (1-hydrogens of cyclopropane ring); at 1.93 and 3.02 ppm (3-hydrogen of cyclopropane ring); at 4.75 and 5.17 ppm (hydrogens of methylene of cyclopentyl ring and 1-hydrogen of propenyl); at 5.5 and 6.03 ppm (2-hydrogen of allyl).

EXAMPLE 42

(1S)
2-methyl-3-allyl-4-cyanomethylene-cyclopent-2-ene-1-yl (1R, trans)
2,2-dimethyl-3-(2-methyl-1-propenyl)-cyclopropane-carboxylate

STEP A:
1S-hydroxy-2-methyl-3-allyl-4-cyanomethylene-cyclopent-2-ene 19.4 ml of O,O-diethyl cyanomethylphosphonate were slowly added to a mixture of 4.8 g of sodium hydride as a 50% mineral oil suspension in 200 ml of monoglyme and the mixture was stirred for 30 minutes and then was added at 5° C. to a solution of 15.22 g of 1S-hydroxy-2-methyl-3-allyl-4-oxo-cyclopent-2-ene in 20 ml of monoglyme over 20 minutes and the mixture was stirred at 5° C. for 15 minutes and at 20° C. for 20 hours. The mixture was evaporated to dryness under reduced pressure and the residue was taken up at 5° C. in a mixture of 100 ml of 1 N hydrochloric acid and 200 ml of water. The mixture was extracted with ether and the organic phase was washed with water, dried and evaporated to dryness. The 18 g of residue were chromatographed over silica gel and was eluted with a 95-5 methylene chloride-ethyl acetate mixture and then 6-4 toluene-ethyl acetate to obtain 8.76 g of 1S-hydroxy-2-methyl-3-allyl-4-cyanomethylene-cyclopent-2-ene with a specific rotation of $[\alpha]_D^{20} = -140° \pm 3°$ (c=0.42% in tolune).

Analysis: C$_{11}$H$_{13}$NO: molecular weight=175.23 Calculated: %C 75.39 %H 7.47, %N 7.99; Found: 75.3, 7.5, 7.8.

IR Spectrum (chloroform): Absorption at 3600 cm$^{-1}$ (OH); at 2205 cm$^{-1}$ conjugated CN); at 1636 and 1611 cm$^{-1}$ (conjugated C=C); at 990-919 cm$^{-1}$ (CH=CH$_2$ deformation).

NMR Spectrum (CDCl$_3$—60 MHz): Peaks at 2.33 to 3.5 ppm (5-hydrogens); at 4.72 ppm (1-hydrogen); at 1.93 ppm (hydrogens of 2-CH$_3$); at 2.33 to 3.5 ppm (1-hydrogens of allyl); at 5.42 to 6.08 ppm (2-hydrogen of allyl); at 4.75 to 5.33 ppm (3-hydrogens of allyl and hydrogen of cyanomethylene).

STEP B: (1S)
2-methyl-3-allyl-4-cyanomethylene-cyclopent-2-ene-1-yl (1R, trans)
2,2-dimethyl-3-(2-methyl-1-propenyl)-cyclopropane-1-carboxylate 2 ml of pyridine were added at 5° C. to a mixture of 3 g of (1S)-hydroxy-2-methyl-3-allyl-4-cyanomethylene-cyclopent-2-ene, 3.3 g of the product of Step A and 30 ml of benzene and the mixture was stirred at 5° C. for 15 minutes and at 20° C. for 2 hours. The mixture was poured into 100 ml of water at 5° C. containing 5 ml of 1 N hydrochloric acid and was extracted with ether. The organic phase was washed with water, dried and evaporated to dryness and the 6 g of residue were chromatographed over silica gel. Elution with an 8-2 methylene chloride-cyclohexane mixture yielded 3.5 g of (1S) 2-methyl-3-allyl-4-cyanomethylene-cyclopent-2-ene-1-yl (1R, trans) 2,2-dimethyl-3-(2-methyl-1-propenyl)-cyclopropane-1-carboxylate with a melting point <50° C. and a specific rotation of $[\alpha]_D^{20} = -152° \pm 3.5°$ (c=1% in benzene).

Analysis: C$_{21}$H$_{27}$NO$_2$: Calculated: %C 77.5, %H 8.36, %N 4.30; Found: 77.6, 8.4, 4.0.

IR Spectrum (chloroform): Absorption at 1715 cm$^{-1}$ (ester carbonyl); at 2210 cm$^{-1}$ (conjugated C≡N); at 1637 and 1614 cm$^{-1}$ (conjugated C=C).

NMR Spectrum (CDCl$_3$—60 MHz): Peaks at 1.7-1.71 ppm (hydrogens of 2-CH$_3$ of propenyl and 3-hydrogens of propenyl); at 1.14 and 1.28 ppm (hydrogens of 2-CH$_3$ of cyclopropane ring); at 5.67 ppm (1-hydrogen of cyclopentyl ring); at 1.9 ppm (hydrogens of 2-CH$_3$ of cyclopentyl ring).

EXAMPLE 43

(1S)
2-methyl-3-allyl-4-cyanomethylene-cyclopent-2-ene-1-yl (1R, cis)
2,2-dimethyl-3-(2,2-dibromo-ethenyl)-cyclopropane-1-carboxylate Using the process of Example 42, 2 g of 1S-hydroxy-2-methyl-3-allyl-4-cyanomethylene-cyclopent-2-ene and 3.7 g of (1R, cis) 2,2-dimethyl-3-(2,2-dibromo-ethenyl)-cyclopropane-carboxylic acid chloride were reacted to obtain after chromatography over silica gel and elution with a 8-2 methylene chloride-cyclohexane mixture 3.9 g of (1S) 2-methyl-3-allyl-4-cyanomethylene-cyclopent-2-ene-1-yl (1R, cis) 2,2-dimethyl-3-(2,2-dibromo-ethenyl)-cyclopropane-1-carboxylate with a specific rotation of $[\alpha]_D^{20} = -23° \pm 2.5°$ (c=0.5% in benzene).

Analysis: C$_{19}$H$_{21}$Br$_2$NO$_2$: Calculated: %C 50.13, %H 4.65, %N 3.07; Found: 50.2, 4.6, 2.8.

IR Spectrum (chloroform): Absorption at 1720 cm$^{-1}$ (carbonyl); at 2210 cm$^{-1}$ (conjugated CN); at 1637 and 1615 cm$^{-1}$ (conjugated C=C).

NMR (CDCl$_3$—60 MHz): Peaks at 6.75 to 6.88 ppm (1-hydrogen of ethenyl); at 1.27 and 1.3 ppm (hydrogens of 2-CH$_3$ of cyclopropane ring); at 5.67 to 5.75 ppm (1-hydrogen of cyclopentyl ring); at 1.9 ppm (hydrogens of 2-CH$_3$ of cyclopentyl ring); at 2.95 to 3.05 ppm (1-hydrogens of allyl); at 5.5 to 6.17 ppm (2-hydrogen of allyl); at 4.83 to 5.17 ppm (3-hydrogens of allyl and hydrogen of methylene).

EXAMPLE 44

(1S)
2-methyl-3-allyl-4-(E)-benzylidene-cyclopent-2-ene-1-yl (1R, trans)
2,2-dimethyl-3-(2-methyl-1-propenyl)-cyclopropane-carboxylate

STEP A:
1S-hydroxy-2-methyl-3-allyl-4-(E)-benzylidene-cyclopent-2-ene 90 ml of tert.-butanol were added to a mixture of 22 g of potassium tert.-butylate in 250 ml of tetrahydrofuran and 76.4 g of triphenylbenzylphosphonium chloride were slowly added thereto. The mixture was stirred for one hour at 23° C. and then a solution of 29.8 g of 1S-hydroxy-2-methyl-3-allyl-4-oxo-cyclopent-2-ene in 10 ml of tetrahydrofuran was slowly added thereto. The mixture was refluxed for 24 hours and was cooled to 20° C. and poured into an iced aqueous monosodium phosphate solution. The mixture was extracted with ether and the ether phase was washed with water, dried and evaporated to dryness. The 81.5 g of residue was chromatographed over silica gel and was eluted with a 1—1 cyclohexane-ethyl acetate mixture to obtain 25.5 g of 1S-hydroxy-2-methyl-3-allyl-4-(E)-benzylidene-cyclopent-2-ene with a melting point <50° C.

IR Spectrum (chloroform): Absorption at 3600 cm$^{-1}$ (OH); at 1635-1625 cm$^{-1}$ (conjugated system); at 1597-1488 cm$^{-1}$ (aromatic bonds); at 999-914 cm$^{-1}$ (allyl).

NMR Spectrum (CDCl$_3$—60 MHz): Peaks at 4.66 ppm (1-hydrogen); at 1.89 ppm (hydrogens of 2-CH$_3$); at 3.03 and 3.12 ppm (1-hydrogens of allyl); at 4.83 to 5.25 ppm (3-hydrogens of allyl); at 5.55 to 6.16 ppm and (2-hydrogens of allyl); at 6.28 ppm (hydrogen of benzylidene); at 7.32 ppm (aromatic hydrogens).

STEP B: (1S) 2-methyl-3-allyl-4-(E)-benzylidene-cyclopent-2-ene-1-yl (1R, trans) 2,2-dimethyl-3-(2-methyl-1-propenyl)-cyclopropanecarboxylate Using the procedure of Step B of Example 42, 3.4 g of 1S-hydroxy-2-methyl-3-allyl-4-(E)-benzylidene-cyclopent-2-ene and 2.8 g of (1R, trans) 2,2-dimethyl-3-(2-methyl-1-propenyl)-cyclopropane-carboxylic acid chloride acid chloride were reacted to obtain after chromatography over silica gel and elution with 98-2 cyclohexane-ethyl acetate mixture containing 1% triethylamine 1.92 g of (1S) 2-methyl-3-allyl-4-(E)-benzylidencyclopent-2-ene-1-yl (1R, trans) 2,2-dimethyl-3-(2-methyl-1-propenyl)-cyclopropane-carboxylate with a specific rotation of $[\alpha]_D^{20} = -171° \pm 3.5°$ (c=0.5% in chloroform).

Analysis: C$_{26}$H$_{32}$O$_2$: Calculated: %C 82.9, %H 8.56; Found: 83.0, 8.7.

IR Spectrum (chloroform): Absorption at 1709 cm$^{-1}$ (ester carbonyl); at 1634-1625 cm$^{-1}$ (conjugated C=C); at 1594-1570-1487 cm$^{-1}$ (aromatic bonds); at 985-913 cm$^{-1}$ (allyl).

NMR Spectrum (CDCl$_3$—60 MHz): Peaks at 1.7 to 1.72 ppm (hydrogens of 2-CH$_3$ of propenyl and 3-hydrogens of propenyl); at 4.75 to 5.25 ppm (1-hydrogen of propenyl); at 1.12 and 1.29 ppm (hydrogens of 2-CH$_3$ of cyclopropane ring); at 1.37 and 1.45 ppm (1-hydrogen of cyclopropane ring); at 5.75 ppm (1-hydrogen of cyclopentyl ring); at 1.83 ppm (hydrogens of 2-CH$_3$ of cyclopentyl ring); at 3.05 and 3.15 ppm (1-hydrogens of allyl); at 4.75 to 5.25 ppm (3-hydrogens of allyl); at 6.32 ppm (hydrogen or carbon of benzylidene); at about 7.30 ppm (hydrogens of phenyl).

EXAMPLE 45

(1S) 2-methyl-3-allyl-4-(cyanoethoxycarbonyl)-methylene-cyclopent-2-ene-1-yl (1R, trans) 2,2-dimethyl-3-(2-methyl-1-propenyl)cyclopropane-carboxylate (1S)-hydroxy-2-methyl-3-allyl-4-(cyanoethoxycarbonyl)-methylene-cyclopent-2-ene A mixture of 3.1 g of 1S-hydroxy-2-methyl-3-allyl-4-oxo-methylene-cyclopent-2-ene, 4.52 g of ethyl cyanoacetate, 0.7 g of ammonium acetate, 1 ml of acetic acid and 50 ml of toluene was refluxed for 6 hours and the water of reaction was distilled. The mixture was cooled to 20° C. and the mixture was diluted with ether. The decanted ether phase was washed with water, dried and evaporated to dryness. The 4.15 g of residue was chromatographed over silica gel and was eluted with a 6-4 benzene-ethyl acetate mixture to obtain 1.06 g of (1S) hydroxy-2-methyl-3-allyl-4-(cyanoethoxycarbonyl)-methylene-cyclopent-2-ene with a specific rotation of $[\alpha]_D^{20} = -87° \pm 2°$ (c=0.9% in chloroform):

IR Spectrum (chloroform): Absorption at 3600 cm$^{-1}$ (OH); at 2220 cm$^{-1}$ (—CN); at 1718 cm$^{-1}$ (ester carbonyl); at 1637, 1616 and 1507 cm$^{-1}$ (conjugated C=C); at 990-918 cm$^{-1}$ (CH=CH$_2$).

NMR Spectrum (CDCl$_3$—60 MHz): Peaks at 1.22, 1.33, 1.45, 4.11, 4.23, 4.35 and 4.47 ppm (COOEt); at 2.06 ppm (hydrogens of 2-CH$_3$); at 2.58 ppm (hydrogen of OH); at 2.75 to 4 ppm (5-hydrogens); at 3.42 to 3.53 ppm (1-hydrogens of allyl); at 4.75 ppm (1-hydrogen); at 4.66 to 5.25 ppm (3-hydrogens of allyl); 5.67 to 6.25 ppm (2-hydrogen of allyl).

STEP B: (1S) 2-methyl-3-allyl-4-(cyanoethoxycarbonyl)-methylene-cyclopent-2-ene-1-yl (1R, trans) 2,2-dimethyl-3-(2-methyl-1-propenyl)-cyclopropanecarboxylate Using the procedure of Step B of Example 42, 2.5 g of the product of Step A and 1.9 g of (1R, trans) 2,2-dimethyl-3-(2-methyl-1-propenyl)-cyclopropane-carboxylic acid chloride were reacted to obtain after chromatography over silica gel and elution with a 97-3 toluene-ethyl acetate mixture 2.37 g of (1S) 2-methyl -3-allyl-4-(cyanoethoxycarbonyl)-methylene-cyclopent-2-ene-1-yl (1R, trans) 2,2-dimethyl-3-(2-methyl-1-propenyl)-cyclopropane-carboxylate with a specific rotation of $[\alpha]_D^{20} = -93° \pm 2°$ (c=1% in chloroform).

Analysis: C$_{24}$H$_{31}$O$_4$N: Calculated: %C 72.52, %H 7.86, %N 3.52; Found: 72.8, 7.7, 3.5.

IR Spectrum (chloroform): Absorption at 2218 (conjugated —CN); at 1719 cm$^{-1}$ (ester carbonyl); at 1637-1618-1570 cm$^{-1}$ (conjugated system); at 991-998 cm$^{-1}$ (CH=CH$_2$ deformation).

NMR Spectrum (CDCl$_3$—60 MHz): Peaks at 1.7 ppm (hydrogens of 2-CH$_3$ of propenyl and 3-hydrogens of propenyl); at 4.75 to 5.25 ppm (1-hydrogen of propenyl); at 1.13 to 1.27 ppm (hydrogens of 2-CH$_3$ of cyclopropane ring); at 5.67 to 5.75 ppm (1-hydrogen of cyclopentyl ring); at 1.98 ppm (hydrogens of 2-CH$_3$ of cyclopentyl ring); at 3.43 to 3.55 ppm (1-hydrogens of allyl); at 4.75 to 5.25 ppm (3-hydrogens of allyl); at 1.22-1.33-1.45-4.1-4.22-4.33 and 4.45 ppm (hydrogens of ethyl).

EXAMPLE 46

(1S) 2-methyl-3-allyl-4-fluorochloromethylene-cyclopent-2-ene-1-yl (1R, trans) 2,2-dimethyl-3-(2-methyl-1-propenyl)-cyclopropanecarboxylate A mixture of 70 ml of n-heptane, 3.4 g of potassium tert.-butylate and 2.85 g of tert.-butanol was stirred at 20° and was then heated to 50° C. for 15 minutes and was then cooled to 20° C. A mixture of 7.86 g of triphenylphosphine in 70 ml of n-heptane was added thereto and after cooling the mixture to 0° C., a solution of 3.9 g of difluorochloromethane in 40 ml of n-heptane was added thereto over 30 minutes. A mixture of 6.28 g of (1S) 2-methyl-3-allyl-4-oxo-cyclopent-2-ene-1-yl (1R, trans) 2,2-dimethyl-3-(2-methyl-1-propenyl)-cyclopropane-carboxylate in 10 ml of tetrahydrofuran was added to the mixture at 0° C. and the mixture was stirred at 20° C. for 24 hours and at 60° C. for one hour and then cooled to 20° C. The mixture was evaporated to dryness under reduced pressure and the residue was empasted with 200 ml of petroleum ether (b.p. =40°-70° C.) and was filtered. The filter was rinsed with petroleum ether and the filtrate was washed with aqueous saturated monosodium phosphate solution, with water, dried and evaporated to dryness to obtain 15 g of residue. The latter was chromatographed over silica gel and was eluted with a 95-5 cyclohexane-ethyl acetate mixture containing 1°/oo triethylamine and a second time with a 5—5 toluene-cyclohexane mixture to obtain 0.8 g of (1S) 2-methyl-3-allyl-4-fluorochloromethylene-cyclopent-2-ene-1-yl (1R, trans) 2,2-dimethyl-3-(2-methyl-1-propenyl)-cyclopropane-carboxylate with a specific rotation of $[\alpha]_D^{20} = -98° \pm 3°$ (c=0.5% in benzene).

Analysis: $C_{20}H_{26}ClFO_2$: Calculated: %C 68.07, %H 7.42, %Cl 10.04, %F 5.38; Found: 68.1, 7.3, 10.2, 5.3.

NMR Spectrum (CDCl$_3$-60 MHz): Peaks at 1.7 and 1.72 ppm (hydrogens of 2-CH$_3$ of propenyl and 3-hydrogens of propenyl); at 4.85-4.97 ppm (1-hydrogen of propenyl); at 1.13 to 1.27 ppm (hydrogens of 2-CH$_3$ of cyclopropane ring); at 1.34-1.43 ppm (1-hydrogen of cyclopropane ring); at 5.53 to 5.65 (ppm (1-hydrogen of cyclopentyl ring); at 1.7 ppm (hydrogens of 2-CH$_3$ of cyclopentyl); at 5.5 to 6.18 ppm (2-hydrogen of allyl); at 4.83 to 5.17 ppm (3-hydrogens of allyl).

EXAMPLE 47

(1S)
2-methyl-3-allyl-4-dichloromethylene-cyclopent-2-ene-1-yl (1R, cis)
2,2-dimethyl-3-(2-methyl-1-propenyl)-cyclopropane-carboxylate Using the procedure of Step B of Example 42, 2.3 g of 1S-hydroxy-2-methyl-3-allyl-4-dichloromethylene-cyclopent-2-ene and 2 g of (1R, cis) 2,2-dimethyl-3-(2-methyl-1-propenyl)-cyclopropane-carboxylic acid chloride were reacted to obtain after chromatography over silica gel and elution with a 6-4 benzene-cyclohexane mixture containing 1°/oo triethylamine 1.5 g of (1S) 2-methyl-3-allyl-4-dichloromethylene-cyclopent-2-ene-1-yl (1R, cis) 2,2-dimethyl-3-(2-methyl-1-propenyl)-cyclopropane-carboxylate with a specific rotation of $[\alpha]_D^{20} = -16.5° \pm 1.5°$ (c=0.7% in benzene).

Analysis: $C_{20}H_{26}Cl_2O_2$: Calculated: %C 65.04, %H 7.10, %Cl 19.20; Found: 64.9, 7.0, 19.3.

IR Spectrum (chloroform): Absorption at 1719 cm$^{-1}$ (ester carbonyl); at 1634 and 1600 cm$^{-1}$ (conjugated C=C); at 1384 cm$^{-1}$ (gem dimethyls); at 995-917 cm$^{-1}$ (CH=CH$_2$).

NMR Spectrum (CDCl$_3$-60 MHz): Peaks at 1.7 and 1.77 ppm (hydrogens of 2-CH$_3$ of propenyl and 3-hydrogens of propenyl); at 5.32-5.45 ppm (1-hydrogen of propenyl); at 1.2-1.26 ppm (hydrogens of 2-CH$_3$ of cyclopentyl); at 5.45-5.58 ppm (1-hydrogen of cyclopentyl); at 1.7-1.77 ppm (hydrogens of 2-CH$_3$ of cyclopentyl ring); at 5.5 to 6.33 ppm (2-hydrogen of allyl); at 4.75 to 5.17 ppm (3-hydrogens of allyl).

EXAMPLE 48

(1S)
2-methyl-3-allyl-4-dichloromethylene-cyclopent-2-ene-1-yl (1R, cis)
2,2-dimethyl-3-(2-oxo-2,3,4,5-tetrahydro-3-thiophenylidenemethyl)-cyclopropane-carboxylate Using the procedure of Step B of Example 42, 2.3 g of 1S-hydroxy-2-methyl-3-allyl-4-dichloromethylene-cyclopent-2-ene and 2.6 g of (1R, cis) 2,2-dimethyl-3-(2-oxo-3,4,5,6-tetrahydro-3-thiophenyldenemethyl)-cyclopropane-carboxylic acid chloride [described in French Pat. No. 2,097,244] were reacted to obtain after chromatography over silica gel and elution with a 25-175 petroleum ether-ethyl acetate mixture containing 1°/oo triethylamine 3.2 g of (1S) 2-methyl-3-allyl-4-dichloromethylene-cyclopent-2-ene-1-yl (1R, cis) 2,2-dimethyl-3-(2-oxo-2,3,4,5-tetrahydro-3-thiophenylidenemethyl)-cyclopropane-carboxylate with a specific rotation of $[\alpha]_D^{20} = +9° \pm 1°$ (c=1% in benzene).

Analysis: $C_{21}H_{24}Cl_2O_3S$: Calculated: %C 59.01, %H 5.66, %Cl16.60, %F 7.50; Found: 58.7, 5.8, 16.4, 7.3.

IR Spectrum (chloroform): Absorption at 1703 cm$^{-1}$ (ester carbonyl); at 1678 cm$^{-1}$ (carbonyl of thiolactone); at 1630 cm$^{-1}$ (C=C).

NMR Spectrum (CDCl$_3$-60 MHz): Peaks at 2.83 to 3.5 ppm (hydrogens of thiophenylidene ring); at 6.75-6.92 ppm (hydrogen of thiophenylidenemethyl); at 1.27 and 1.35 ppm (hydrogens of 2-CH$_3$ of cyclopropane); at 5.48-5.93 ppm (1-hydrogen of cyclopentyl ring); at 1.77 ppm (hydrogens of 2-CH$_3$ of cyclopentyl ring); at 2.83 to 3.5 ppm (1-hydrogens of allyl); at 4.75 to 5.17 ppm (3-hydrogens of allyl); at 5.5 to 6.25 ppm (1-hydrogen of allyl).

EXAMPLE 49

(1S)
2-methyl-3-allyl-4-dichloromethylene-cyclopent-2-ene-1-yl (1R, trans) 2,2-dimethyl-3-(2-fluoro-2-chloro-(E) and (Z)-ethenyl)-cyclopropane-carboxylate Using the procedure of Step B of Example 42, 2.5 g of 1S-hydroxy-2-methyl-3-allyl-4-dichlormethylene-cyclopent-2-ene and 2.4 g of (1R, trans) 2,2-dimethyl-3-(2-fluoro-2-dichloro-(E) and (Z)-ethenyl)-cyclopropane-carboxylic acid chloride were reacted to obtain after chromatography over silica gel and elution with a 9-1 benzene-ethyl acetate mixture containing 1°/oo triethylamine 1.92 g of (1S) 2-methyl-3-allyl-4-dichloromethylene-cyclopent-2-ene-1-yl (1R, trans) 2,2-dimethyl-3-(2-fluoro-2-chloro-(E) and (Z)-ethenyl)-cyclopropane-carboxylate with a specific rotation of $[\alpha]_D^{20} = -64° \pm 2.5°$ (c=0.6% in chloroform).

Analysis: $C_{18}H_{20}Cl_3FO_2$: Calculated: %C 54.91, %H 5.12, %Cl 27.01, %F 4.82; Found: 55.1, 5.0, 27.0, 4.9.

IR Spectrum (chloroform): Absorption at 1716 cm$^{-1}$ (ester carbonyl); at 1670 cm$^{-1}$ (C=C); at 1632-1600 cm$^-$ (conjugated system); at 1380 cm$^{-1}$ (gem dimethyl); at 900 and 990 cm$^{-1}$ (CH=CH$_2$ deformation).

NMR Spectrum (CDCl$_3$-60 MHz): Peaks at 4.35-4.48 ppm and 4.8-4.93 ppm and 4.95 to 5.25 ppm (1-hydrogen of ethenyl); at 1.15-1.27 ppm (hydrogens of 2-CH$_3$ of cyclopropane); at 5.58 ppm (1-hydrogen of cyclopentyl ring); at 1.77 ppm (hydrogens of 2-CH$_3$ of cyclopentyl ring); at 5.42 to 6.25 ppm (2-hydrogen of allyl); at 4.75 to 5.16 ppm (3-hydrogens of allyl).

EXAMPLE 50

(1S)
2-methyl-3-allyl-4-dichloromethylene-cyclopent-2-ene-1-yl (1R, trans) 2,2-dimethyl-3-[2-(E) and (Z)-cyanoethenyl]-cyclopropane-carboxylate Using the procedure of Step B of Example 42, 2.5 g of 1S-hydroxy-2-methyl-3-allyl-4-dichloromethylene-cyclopent-2-ene and 2.1 g of (1R, trans) 2,2-dimethyl-3-[2-(E) and (Z)-cyanoethenyl]-cyclopropane carboxylic acid chloride were reacted to obtain after chromatography over silica gel and elution with a 9-1 benzene-ethyl acetate mixture containing 1‰ triethylamine 0.981 g of (1S) 2-methyl-3-allyl-4-dichloromethylene-cyclopent-2-ene-1-yl (1R, trans) 2,2-dimethyl-3-[2-(E) and (Z)-cyanoethenyl]-cyclopropane-carboxylate with a specific rotation of $[\alpha]_D^{20} = -50° \pm 1.5°$ (c = 1% in chloroform).

IR Spectrum (chloroform): Absorption at 2218 cm$^{-1}$ (—CN); at 1720 cm$^{-1}$ (ester carbonyl); at 1628,1618-1602 cm$^{-1}$ (conjugated C=C); at 1390-1380 cm$^{-1}$ (gem dimethyl); at 990-900 cm$^{-1}$ (allyl); at 968 cm$^{-1}$ (trans CH=CH).

NMR Spectrum (CDCl$_3$-60 MHz): Peaks at 4.83 to 6.67 ppm (1-and 2-hydrogens of ethenyl); at 1.25-1.32-1.37 ppm (hydrogens of 2-CH$_3$ of cyclopropane); at 5.58 ppm (1-hydrogen of cyclopentyl ring); at 1.8 ppm (hydrogens of 2-CH$_3$ of cyclopentyl ring); at 5.5 to 6.33 ppm (1-hydrogen of allyl); at 4.83 to 5.17 ppm (3-hydrogens of allyl).

EXAMPLE 51

(1S)
2-methyl-3-allyl-4-dichloromethylene-cyclopent-2-ene-1-yl (1R, cis) 2,2-dimethyl-3-[2-(E) and (Z)-cyanoethenyl]-cyclopropane-carboxylate Using the procedure of Step B of Example 42, 2.5 g of 1S-hydroxy-2-methyl-3-allyl-4-dichloromethylene-cyclopent-2-ene and 2.1 g of (1R, cis) 2,2-dimethyl-3-[2-(E) and (Z)-cyanoethenyl]-cyclopropane carboxylate were reacted to obtain after chromatography over silica gel and elution with a 9-1 benzene-ethyl acetate mixture containing 1‰ triethylamine 1.692 g of (1S) 2-methyl-3-allyl-4-dichloromethylene-cyclopent-2-ene-1-yl (1R, cis) 2,2-dimethyl-3-[2-(E) and (Z)-cyanoethenyl]-cyclopropane-carboxylate with a specific rotation of $[\alpha]_D^{20} = -6° \pm 2°$ (c = 0.5% in chloroform).

IR Spectrum (chloroform): Absorption at 2210 cm$^{-1}$ (conjugated CN); at 1718 cm$^{-1}$ (ester carbonyl); at 1340-1621-1600 cm$^{-1}$ (C=C); at 1390-1380 cm$^{-1}$ (gem dimethyl); at 990-900 cm$^{-1}$ (allyl); at 970 cm$^{-1}$ (trans CH=CH).

NMR Spectrum (CDCl$_3$-60 MHz): Peaks at 5.16 to 5.66 ppm (2-hydrogen of ethenyl); at 5.72 to 7.22 ppm (1-hydrogen of ethenyl); at 1.24-1.3-1.32 ppm (hydrogens of 2-CH$_3$ of cyclopropane ring); at 5.58 ppm (1-hydrogen of cyclopentyl ring); at 1.76 ppm (hydrogens of 2-methyl of cyclopentyl ring); at 5.5 to 6.17 ppm (2-hydrogen of allyl); at 4.75 to 5.17 ppm (3-hydrogens of allyl).

EXAMPLE 52

(1S)
2-methyl-3-allyl-4-dichloromethylene-cyclopent-2-ene-1-yl (1R, trans) 2,2-dimethyl-3-[2-methoxycarbonyl-(E)-ethenyl]-cyclopropane-carboxylate A mixture of 0.5 g of (1R, trans) of 2,2-dimethyl-3-[2-methoxycarbonyl-(E)-ethenyl]-cyclopropane-carboxylic acid, 10 ml of methylene chloride, 20 mg of 4-dimethylaminopyridine and 0.52 g of dicylohexylcarbodiimide was stirred at 20° C. for one hour and 0.54 g of 1S-hydroxy-2-methyl-3-allyl-4-dichloromethylene-cyclopent-2-ene were added thereto. The mixture was stirred at 20° C. for 2 hours and was filtered and the filtrate was washed with water, dried and evaporated to dryness. The 1.7 g of residue was chromatographed over silica gel and was eluted with a 9-1 benzene-ethyl acetate mixture containing 1‰ triethylamine to obtain 0.8 g of (1S) 2-methyl-3-allyl-4-dichloromethylene-cyclopent-2-ene-1-yl (1R, trans) 2,2-dimethyl-3-[2-methoxycarbonyl-(E)-ethenyl]-cyclopropane-carboxylate with a specific rotation of $[\alpha]_D^{20} = -27.5° \pm 2°$ (c = 0.4% in chloroform).

IR Spectrum (chloroform): Absorption at 1715 cm$^{-1}$ (ester carbonyl); at 1649-1635-1602 cm$^{-1}$ (conjugated C=C); at 1391-1380 cm$^{-1}$ (gem dimethyl); at 916 cm$^{-1}$ (deformation of CH=CH$_3$); at 980 cm$^{-1}$ (trans CH=CH).

NMR Spectrum (CDCl$_3$-60 MHz): Peaks at 3.69 ppm (hydrogens of CH$_3$O-); at 6.05-5.8 ppm (2-hydrogen of ethenyl); at 6.43-6.6 ppm and 6.68-6.85 ppm (1-hydrogen of ethenyl); at 1.23 and 1.29 ppm (hydrogens of 2-CH$_3$ of cyclopropane ring); at 5.58 ppm (1-hydrogen of cyclopentyl ring); at 1.77 ppm (hydrogens of 2-CH$_3$ of cyclopentyl ring); at 4.75 to 5.17 ppm (3-hydrogens of allyl).

EXAMPLE 53

(1S)
2-methyl-3-allyl-4-dichloromethylene-cyclopent-2-ene-1-yl (1R, trans) 2,2-dimethyl-3-(2-methyl-1-propenyl)-cyclopropane-carboxylate 8.2 ml of tert.-butanol were added at 20° C. to a mixture of 170 ml of n-heptane and 9.8 g of potassium tert.-butylate followed by the addition of 23 g of triphenylphosphine and after cooling the mixture to −20° C., a solution of 8 ml of chloroform in 20 ml of n-heptane were slowly added thereto. The mixture was stirred at −20° C. for one hour and then a solution of 7.86 g of (1R, trans) 2,2-dimethyl-3-(2-methyl-1-propenyl)-cyclopropane-carboxylic acid in 20 ml of tetrahydrofuran was slowly added thereto at −20° C. The mixture was then stirred at −20° C. for one hour, 0° C. for one hour and 20° C. for 12 hours and was evaporated to dryness under reduced pressure. The 21 g of residue were empasted with petroleum ether (b.p. 40°-70° C.) and was filtered and the filtrate was washed with aqueous saturated monosodium in phosphate solution and then with water, dried and evaporated to dryness. The 11 g of residue was chromatographed twice over silica gel with elution with a 98-2 cyclohexane-ethyl acetate mixture containing 1‰ triethylamine and then with a 6-4 cyclohexane-toluene mixture to obtain 1.95 g of (1S) 2-methyl-3-allyl-4-dichloromethylene-cyclopent-2-ene-1-yl (1R, trans) 2,2-dimethyl-3-(2-methyl-1-propenyl)- cyclopropane-carboxylate with a specific rotation of $[\alpha]_D^{20} = -95.5° \pm 2.5°$ (c=0.7% in benzene).

Analysis: $C_{20}H_{26}Cl_2O_2$: Calculated: %C 65.04, %H 7.09, %Cl 19.19; Found: 65.0, 7.0, 19.0.

IR Spectrum (chloroform): Absorption at 1700 cm$^{-1}$ (ester carbonyl); at 1638-1605 cm$^{-1}$ (conjugated C=C); at 1381 cm$^{-1}$ (gem dimethyl); at 994-918 cm$^{-1}$ (allyl).

NMR Spectrum (CDCl$_3$-60 MHz): Peaks at 1.72 ppm (hydrogens of 2-CH$_3$ of propenyl and 3-hydrogens of propenyl); at 4.83 to 5.17 ppm (1-hydrogen of propenyl); at 1.15-1.28 ppm (hydrogens of 2-CH$_3$ of cyclopropane ring); at 1-1.44 ppm (1-hydrogen of cyclopropane ring); at 5.5 to 5.58 ppm (1-hydrogen of cyclopentyl); at 1.78 ppm (hydrogens of 2-CH$_3$ of cyclopentyl ring); at 5.5 to 5.25 ppm (2-hydrogens of allyl); at 4.83 to 5.17 ppm (3-hydrogens of allyl).

EXAMPLE 54

(1S) 2-methyl-3-allyl-4-dicyanomethylene-cyclopent-2-ene-1-yl (1R, trans) 2,2-dimethyl-3-(2-methyl-1-propenyl)-cyclopropane-carboxylate STEP A: 1S-hydroxy-2-methyl-3-allyl-4-dicyanomethylene-cyclopent-2-ene Using the procedure of Example 45, 45 g of 1S-hydroxy-2-methyl-3-allyl-4-oxo-cyclopent-2-ene and 24 g of malonitrile were reacted to obtain after chromatography over silica gel and elution with a 6-4 toluene-ethyl acetate mixture and then an 8-2 toluene-ethyl acetate mixture 34.9 g of (1S) 2-methyl-3-allyl-4-cyanomethylene-cyclopent-2-ene with a specific rotation of $[\alpha]_D^{20} = -203° \pm 4°$ (c=0.5% in benzene).

Analysis: $C_{12}H_{12}N_2O$: Calculated: %C 71.98, %H 6.04, %N 13.99; Found: 71.8, 6.2, 13.8.

IR Spectrum (chloroform): Absorption at 3600 cm$^{-1}$ (OH); at 2222 cm$^{-1}$ (CN); at 1637, 1611 and 1567 cm$^{-1}$ (conjugated double bond); at 990 and 920 cm$^{-1}$ (CH=CH$_2$ deformation).

NMR Spectrum (CDCl$_3$-60 MHz): Peaks at 4.75 ppm (1-hydrogen); at 2.58 ppm (hydrogen of OH); at 2.07 ppm (hydrogens of 2-CH$_3$); at 3.25 to 3.42 ppm (1-hydrogens of allyl); at 5.5 to 6.25 ppm (2-hydrogen of allyl); at 4.67 to 5.25 ppm (3-hydrogens of allyl).

STEP B: (1S) 2-methyl-3-allyl-4-cyanomethylene-cyclopent-2-ene-1-yl (1R, trans) 2,2-dimethyl-3-(2-methyl-1-propenyl)-cyclopropane-carboxylate 1.5 ml of pyridine were added at 5° C. to a mixture of 3 g of the product of Step A, 3 g of (1R, trans) 2,2-dimethyl-3-(2-methyl-1-propenyl)-cyclopropane-carboxylic acid chloride and 50 ml of benzene and the mixture was held at 5° C. for 15 minutes, at 20° C. for 2 hours and was then poured into a mixture of 18 ml of 2 N hydrochloric acid and 100 ml of water at 5° C. The mixture was extracted with ether and the organic phase was washed with water, dried and evaporated to dryness. The 6.5 g of residue was chromatographed over silica gel and was eluted with a 97-3 toluene-ethyl acetate mixture to obtain 4.93 g of (1S) 2-methyl-3-allyl-4-cyanomethylene-cyclopent-2-ene-1-yl (1R, trans) 2,2-dimethyl-3-(2-methyl-1-propenyl)-cyclopropane-carboxylate with a specific rotation of $[\alpha]_D^{20} = -162.5° \pm 3.5°$ (c=0.6% in benzene).

Analysis: $C_{22}H_{26}N_2O_2$: Calculated: %C 75.39, %H 7.47, %N 7.99; Found: 75.3, 7.6, 7.9.

IR Spectrum (chloroform): Absorption at 2220 cm$^{-1}$ (conjugated CN); at 1712 cm$^{-1}$ (ester carbonyl); at 1640-1617-1570 cm$^{-1}$ (conjugated system); at 995-920 cm$^{-1}$ (allyl).

NMR Spectrum (CDCl$_3$-60 MHz): Peaks at 1.73 ppm (hydrogens of 2-CH$_3$ of propenyl and 3-hydrogens of propenyl); at 4.83-4.96 ppm (1-hydrogen of propenyl); at 1.36-1.45 ppm (1-hydrogen of cyclopropane ring); at 1.17-1.29 ppm (hydrogens of 2-CH$_3$ of cyclopropane ring); at 5.67 ppm (1-hydrogen of cyclopentyl); at 2.03 ppm (hydrogens of 2-CH$_3$ of cyclopentyl); at 3.33-3.43 ppm (1-hydrogens of allyl); at 5.58 to 6.25 ppm (2-hydrogen of allyl); at 4.92 to 5.25 ppm (3-hydrogens of allyl).

EXAMPLE 55

(1S) 2-methyl-3-allyl-4-methylene-cyclopent-2-ene-1-yl (1R, cis) 2,2-dimethyl-3-ethynyl-cyclopropane-carboxylate STEP A: (1R, cis) 2,2-dimethyl-3-ethynyl-cyclopropane-carboxylic acid A mixture of 100 ml of tetrahydrofuran and 100 ml of ether were slowly added with stirring at −55° C. to a solution of 20 g of 4-butyllithium in 100 ml of cyclohexane and then a solution of 15 g of (1R, cis) 2,2-dimethyl-3-(2,2-dichlorovinyl)-cyclopropane-carboxylic acid in 20 ml of ether and 20 ml of tetrahydrofuran was added thereto with stirring at −62° C. The temperature was allowed to rise with stirring to room temperature over 48 hours and was then cooled to 5° C. 9 ml of isopropanol and then 100 ml of 2 N sulfuric acid were added to the reaction mixture and the decanted aqueous phase was extracted with ether. The organic phase was washed with water, dried and evaporated to dryness under reduced pressure. The residue was taken up in 5 ml of petroleum ether and the mixture was iced and filtered. The recovered product was dried to obtain 4.7 g of (1R, cis) 2,2-dimethyl-3-ethynylcyclopropane-carboxylic acid.

STEP B: (1R, cis) 2,2-dimethyl-3-ethynyl-cyclopropanecarboxylic acid chloride

A mixture of 7 g of the product of Step A, 45 ml of petroleum ether (b.p.=40°-70° C.) and 15 ml of thionyl chloride was refluxed for 3 hours and was evaporated to dryness under reduced pressure. The residue was rectified to obtain 7 g of (1R, cis) 2,2-dimethyl-3-ethynyl-cyclopropane-carboxylic acid chloride.

STEP C: (1S) 2-methyl-3-allyl-4-methylene-cyclopent-2-ene-1-yl (1R, cis) 2,2-dimethyl-3-ethynyl-cyclopropane-carboxylate Using the procedure of Step B of Example 54, 2.5 g of 1S-hydroxy-2-methyl-3-allyl-4-methylene-cyclopent-2-ene and 2.5 g of the product of Step B were reacted to obtain after chromatography over silica gel and elution with a 95-5 petroleum ether (b.p.=40°-70° C.)-ether mixture containing 1°/$_{oo}$ triethylamine 1.26 g of (1S) 2-methyl-3-allyl-4-methylene-cyclopent-2-ene-1-yl (1R, cis) 2,2-dimethyl-3-ethynylcyclopropane-carboxylate with a specific rotation of $[\alpha]_D^{20} = -83° \pm 3°$ (c=0.6% in chloroform).

IR Spectrum (chloroform): Absorption at 3300 cm$^{-1}$ (CH of ethenyl); at 2225 cm$^{-1}$ (C≡C); at 1728 cm$^{-1}$ (ester carbonyl); at 1390 and 1379 cm$^{-1}$ (gem dimethyl); at 1692 cm$^{-1}$ (C≡C).

NMR Spectrum (CDCl$_3$-60 MHz): Peaks at 2.1 ppm (3-hydrogen of ethynyl); at 1.18 to 1.38 ppm (hydrogens of 2-methyl of cyclopropane ring); towards 1.7 ppm 1- and 3-hydrogens of cyclopropane ring); at 4.6 to 5.25 ppm (hydrogens of CH$_2$= and 3-hydrogens of allyl); at 2.9 and 3 ppm (1-hydrogens of allyl); at 5.48 to 6.16 ppm (2-hydrogens of allyl); at 1.78 ppm (hydrogen of 2-CH$_3$ of cyclopentyl ring); at 5.66 ppm (1-hydrogen of cyclopentyl ring).

EXAMPLE 56

(1S) 2-methyl-3-allyl-4-methylene-cyclopent-2-ene-1-yl (1R, trans) 2,2-dimethyl-3-ethynyl-cyclopropane-carboxylate Using the procedure of Example 54, 1.2 g of (1R, trans) 2,2-dimethyl-3-ethynyl-cyclopropane-carboxylic acid chloride [prepared from (1R, trans) 2,2-dimethyl-3-(2,2-dichlorovinyl)-cyclopropane carboxylic acid by the process of Example 55] and 1.4 g of 1S-hydroxy-2-methyl-3-allyl-4-methylene-cyclopent-2-ene were reacted to obtain after chromatography over silica gel and elution with a 95–5 petroleum ether (b.p.=40°–70° C.)-ether mixture containing 1°/$_{oo}$ triethylamine 0.83 g of (1S) 2-methyl-3-allyl-4-methylenecyclopent-2-ene-1-yl (1R, trans) 2,2-dimethyl-3-ethynyl-cyclopropane-carboxylate with a specific rotation of $[\alpha]_D^{20} = -39.5° \pm 1.5°$ (c=1.5% in chloroform).

IR Spectrum (chloroform): Absorption at 3300 cm$^{-1}$ (CH of ethynyl); at 1712 cm$^{-1}$ (ester carbonyl); at 1633 cm$^{-1}$ (conjugated C=C); at 2225 cm$^{-1}$ (C≡C); at 985–915 cm$^{-1}$ (allyl).

NMR Spectrum (CDCl$_3$-60 MHz): Peaks at 1.95 ppm (3-hydrogen of ethynyl) at 1.23 and 1.3 ppm (hydrogens of 2-CH$_3$ of cyclopropane ring); toward 5.58 ppm (1-hydrogen of cyclopentyl); at 1.8 ppm (hydrogens of 2-CH$_3$ of cyclopentyl ring); at 4.75 to 5.16 ppm (hydrogens of CH$_2$= and 3-hydrogens of allyl); at 5.52 to 6.23 ppm (2-hydrogens of allyl); at 2.94 to 3 ppm (1-hydrogens of allyl).

EXAMPLE 57

(1S) 2-methyl-3-allyl-4-methylene-cyclopent-2-ene-1-yl 2,2,3, 3-tetramethyl-cyclopropane-carboxylate A solution of 6.54 g of dicyclohexyldicarbodiimide in 10 ml of methylene chloride was slowly added at 0° C. with stirring to a mixture of 3.72 g of 2,2,3,3-tetramethyl-cyclopropane carboxylic acid, 100 ml of methylene chloride, 4.33 g of 1S-hydroxy-2-methyl-3-allyl-4-methylene-cyclopent-2-ene and 0.4 ml of dimethylamino-pyridine and the mixture stood at room temperature for 27 hours and was filtered. The filtrate was evaporated to dryness and the residue was taken up in petroleum ether. The solution was washed with water, dried and evaporated to dryness and the residue was chromatographed over silica gel. Elution with a 9–1 petroleum ether (b.p.=40°-70° C.)-ether containing 1°/$_{oo}$ triethylamine yielded 4.1 g of (1S) 2-methyl-3-allyl-4-methylene-cyclopent-2-ene-1-yl 2,2,3,3-tetramethyl-cyclopropane-carboxylate with a specific rotation of $[\alpha]_D^{20} = -56° \pm 2.5°$ (c=0.7% in ethanol).

IR Spectrum (chloroform): Absorption at 1710 cm$^{-1}$ (ester carbonyl); at 1632 cm$^{-1}$ (conjugated C=C); at 1394–1380 cm$^{-1}$ (gme dimethyl); at 990–915 cm$^{-1}$ (allyl); at 866 cm$^{-1}$ (methylene).

NMR Spectrum (CDCl$_3$-60 MHz): Peaks at 1.17 and 1.25 ppm (hydrogens of 2- and 3-CH$_3$ of cyclopropane); at 5.58 ppm (1-hydrogen of cyclopentyl); at 4.73 to 5.2 ppm (hydrogens of methylene and 3-hydrogens of allyl); at 5.5 to 6.16 ppm (2-hydrogens of allyl); at 2.95 to 3.05 ppm (1-hydrogens of allyl); at 1.8 ppm (hydrogen of 2-(CH$_3$ of cyclopentyl ring).

EXAMPLE 58

(1S) 2-methyl-3-allyl-4-methylene-cyclopent-2-ene-1-yl (1R, cis) 2,2-dimethyl-3-[2-(E) and (Z)-cyano-2-phenyl-ethenyl]-cyclopropane-carboxylate STEP A: (1R, cis) 2,2-dimethyl-3-[2-(E) and (Z)-cyano-2-phenyl-etheny]-cyclopropane-carboxylic acid 5.8 g of benzyl cyanide and then 7.1 g of the lactone of (cis) 2,2-dimethyl-3S-dihydroxymethyl-cyclopropane-1-carboxylic acid were added to a solution of 3.5 g of potassium methylate in 70 ml of methanol and the mixture was refluxed for 90 minutes and then was evaporated to dryness. The residue was taken up in 75 ml of N hydrochloric acid and 30 ml of ether and the mixture was stirred at room temperature for 15 minutes. The mixture was extracted with ethyl acetate and the organic phase was dried and evaporated to dryness. The product was washed with petroleum ether (b.p.=40° to 70° C.) and dried to obtain 9.5 of (1R, cis) 2,2-dimethyl-3-[2-(E) and (Z)-cyano-2-phenyl-ethenyl]-cyclopropane-carboxylic acid.

IR Spectrum (chloroform): Absorption at 3500 cm$^{-1}$ (OH of acid); at 2215 cm$^{-1}$ (conjugated (CN); at 1730–1695 cm$^{-1}$ (carbonyl); at 1607 cm$^{-1}$ (shoulder), 1598 and 1493 cm$^{-1}$ (aromatic); at 690 cm$^{-1}$ (phenyl).

STEP B: (1S) 2-methyl-3 -allyl-4-methylene-cyclopent-2-ene-1-yl (1R, cis) 2,2-dimethyl-3-[2-(E) and (Z)-cyano-2-phenylethenyl]-cyclopropane carboxylate A solution of 3.3 g of the product of Step A in 4 ml of thionyl chloride was heated at 80° C. for 15 minutes to form the corresponding acid chloride which was dissolved in 50 ml of benzene and 2.57 g of 1S-hydroxy-2-methyl-3-allyl-4-methylene-cyclopent-2-ene and 1.9 ml of pyridine were added thereto. The mixture was stirred at room temperature for 16 hours and was poured into 200 ml of benzene. The organic phase was washed with 30 ml of N hydrochloric acid solution, then with 15 ml of M potassium bicarbonate solution, then with 30 ml of water, dried and evaporated to dryness. The residue was chromatographed over silica gel and was eluted with a 9–1 cyclohexane-ethyl acetate mixture to obtain 3.4 g of (1S) 2-methyl-3-allyl-4-methylene-cyclopent-2-ene-1-yl (1R, cis) 2,2-dimethyl-3-[2-(E) and (Z)-cyano-2-phenyl-ethenyl]-cyclopropane carboxylate with a specific rotation of $[\alpha]_D^{20} = -39.5° \pm 2.5°$ (c=0.5% in benzene).

IR Spectrum (chloroform): Absorption at 2215 cm$^{-1}$ (conjugated CN); at 1711 cm$^{-1}$ (ester carbonyl); at 1631–1603 cm$^{-1}$ (C=C and conjugate); at 1596–1490 cm$^{-1}$ (aromatic); at 990–913 cm$^{-1}$ (allyl: deformation); at 864 cm$^{-1}$ (C=C of methylene and allethrolone).

NMR Spectrum (CDCl$_3$-60 MHz): Peaks at 1.35 and 1.38 ppm (hydrogens of 2-CH$_3$ of cyclopropyl); at 1.78 ppm (hydrogens of 2-CH$_3$ of cyclopentyl ring); at 4.75 to 5.25 ppm (hydrogens of methylene); at 5.5 to 6.16 ppm (2-hydrogens of allyl); towards 5.58 ppm (1-hydrogen of cyclopentyl); at 7.17 to 7.66 ppm (aromatic hydrocarbons).

INSECTICIDAL ACTIVITY

A. Knockdown Activity against Houseflies

The test compounds dissolved in equal volumes of acetone and kerosene were directly sprayed on 3 day old female houseflies in a Kearns and March chamber with a volume of 2×0.2 ml. 50 insects were used in each test and readings were taken 2,4,6,8,10 and 15 minutes after the spraying and compared to controls to determine $KT_{50}$ for the test compounds with and without piperonyl butoxide synergist.

B. Lethal Activity against Houseflies

1 μl of an acetone solution of the test compounds was applied topically to the dorsal thorax of groups of 50 female houseflies 4 days old with an Arnold micromanipulator and the number of dead insects was determined 24 hours later. The tests were effected without and with 10 parts by weight of piperonyl butoxide per part by weight of test compound and $DL_{50}$ (dose in nanograms to kill 50% of the insects) was determined.

C. Insecticidal Activity against Spodoptera Littoralis

1 μl of an acetone solution of compound A was topically placed on the dorsal thorax of each insect using 15 Spodoptera littoralis caterpillars in the 4th larva stage for each dose. After this treatment, the individuals were placed in an artifical nutritive medium (Poitout medium) and the degree of efficacity was determined in nanogram per insect after 24 and 48 hours.

D. Insecticidal Activity against Epilachna Varivestris

The test was effected by topical application as in test C using Epilachna varivestris in the last larvae stage and after treatment, the individuals were fed bean plants. The mortality was determined after 72 hours.

E. Insecticidal Activity against Sitophilus Granarius and Tribolium Castaneum Using the procedure of test C, an acetone solution of compound A was topically applied to Sitophilus granarius and the insects were then placed in wheat. The mortality was determined 24 and 48 hours and 6 and 7 days after treatment.

F. Insecticidal Activity against Blatella germanica (adult males)

The test carried out is a test by film on glass. 1.54 cm3 of an acetone solution at 10 mg/l of the product to be tested, is deposited in Petri boxes of 154 cm2, then the 0.1 mg of active material per m2.

Afterwards, the insects are taken out of the Petri box and transferred to clean glass jars. The mortality control is made at the end of 24 hours, 48 hours and 6 days.

G. Insecticidal Activity against Aphis Craccivora

A microdrop of an actone solution of the test compound was topically applied to Aphis Craccivora and the mortality was 100% after 24 and 48 hours.

H. Lethal Activity against Aedes Aegypti

This test was the O.M.S. method wherein 20 adult insects were placed in contact with a sheet of filter paper which had been treated by placing 180 ml of an acetone solution of the test compound with a pipette on the paper. The contamination was effected 24 hours after treatment of the paper and the $DL_{50}$ was determined. The test was repeated twice for each dose.

I. Knockdown Activity against Aedes Aegypti

The test method was analogous to that described above for the lethal test except that the counting of the dead insects were determined at 2 minute intervals until all the insects were knocked down to ascertain the $KT_{50}$ (knock down time 50).

The test results are summarized in the following Tables for (1S) 2-methyl-3-allyl-4-methylene-cyclopent-2-ene-1-yl(1R, trans) 2,2-dimethyl-3-(2-methyl-1-propenyl)-cyclopropane-carboxylate [compound A], (1S) 2-methyl-3-allyl-4-methylene-cyclopent-2-ene-1-yl (1R, trans) 2,2-dimethyl-3-cyclopentylidenemethyl-cyclopropane-1-carboxylate [compound B], (1S) 2-methyl-3-allyl-4-methylene-cyclopent-2-ene-1-yl (1R, trans) 2,2-dimethyl-3-(2,2-dichloroethenyl)-cyclopropane-1-carboxylate [compound C], (1S) 2-methyl-3-allyl-4-methylenecyclopent-2-ene-1-yl (1R, trans) 2,2-dimethyl-3-(2,2-dibromoethenyl)-cyclopropane-carboxylate [compound D], (1RS) 2-methyl-3-(3-methyl-2-butenyl)-4-methylene-cyclopent-2-ene-1-yl (1R, trans) 2,2-dimethyl-3-cyclopentylidenemethyl-cyclopropane-carboxylate [compound E], (1S) 2-methyl-3-allyl-4-dichloromethylene-cyclopent-2-ene-1-yl (1R, cis) 2,2-dimethyl-3-(2,2-difluoroethenyl)-cyclopropane-carboxylate [compound F], (1S) 2-methyl-3-allyl-4-methylene-cyclopent-2-ene-1-yl (1R, trans) 2,2-dimethyl-3-(2,2-difluoroethenyl)-cyclopropane-carboxylate [compound G], (1S) 2-methyl-3-allyl-4-methylene-cyclopent-2-ene-1-yl (1R, cis) 2,2-dimethyl-3-(2,2-difluoroethenyl)-cyclopropane-carboxylate ]compound H], (1S) 2-methyl-3-allyl-4-methylene-cyclopent-2-ene-1-yl (1R, trans) 2,2-dimethyl-3-[2-(Z)-cyanoethenyl]-cyclopropane-carboxylate [compound I], (1S) 2-methyl-3-allyl-4-methylene-cyclopent-2-ene-1-yl (1R, trans) 2,2-dimethyl-3-(2-fluoro-2-chloro-ethenyl)-cyclopropane-carboxylate [compound J], (1S) 2-methyl-3-allyl-4-methylenecyclopent-2-ene-1-yl (1R, trans) 2,2-dimethyl-3-cyclobutylidenemethyl-cyclopropane-carboxylate [compound K], (1S) 2-methyl-3-allyl-4-methylene-cyclopent-2-ene-1-yl (1R, cis) 2,2-dimethyl-3-ethynyl-cyclopropane-carboxylate [compound L], and (S) dichloromethylene-allethrolone (1R, cis) 2,2-dimethyl-3-(2,2-dichloroethenyl)-cyclopropane-carboxylate [compound M].

TABLE I

| A. Knockdown against Houseflies | | | | | | | | | |
|---|---|---|---|---|---|---|---|---|---|
| Product | | Doses in mg/L | 2 mn | 4 mn | % KD 6 mn | 8 mn | 10 mn | 15 mn | $KT_{50}$ en mn |
| A | without synergist | 500 | 0 | 0 | 6.7 | 33.3 | 56.7 | 93.3 | 8.8 |
| B | with synergist without | 500 | 3.3 | 6.7 | 30.0 | 56.7 | 73.3 | 96.7 | 7.0 |

TABLE I-continued

A. Knockdown against Houseflies

| Product | | Doses in mg/L | % KD | | | | | | $KT_{50}$ en mn |
|---|---|---|---|---|---|---|---|---|---|
| | | | 2 mn | 4 mn | 6 mn | 8 mn | 10 mn | 15 mn | |
| | synergist with | 500 | 0 | 3.3 | 6.7 | 16.7 | 43.3 | 76.7 | 11.0 |
| | synergist | 500 | 0 | 3.3 | 16.7 | 33.3 | 63.3 | 100 | 9.5 |
| C | | 1,000 | 4 | 28 | 54 | 86 | 98 | — | 100 | 8.7 |
| | | 500 | 1.8 | 1.8 | 8.8 | 31.6 | 70.2 | — | 91.2 | 14.5 |
| | | 250 | 0 | 0 | 2 | 9.8 | 17.6 | 35.3 | 60.8 | 26.0 |
| D | without synergist with | 491 | 0 | 0 | 38 | 74 | 92 | 100 | 6.5 |
| | synergist | 507 | 0 | 18 | 74 | 98 | 100 | 100 | 5.2 |
| G | without synergist | | | | | | | | 3.6 |
| I | without synergist | | | | | | | | 2.64 |
| J | without synergist | | | | | | | | 5.2 |
| K | without synergist | | | | | | | | 5 |
| L | without synergist | | | | | | | | 5.9 |

TABLE II

B. Lethal Activity against Houseflies

| Product | | Doses in ng per insect | Number of insects | % of mortality at 24 hours | $DL_{50}$ in ng per insects |
|---|---|---|---|---|---|
| | | 500 | 30 | 100 | |
| | | 250 | 30 | 100 | |
| | | 100 | 60 | 100 | |
| A | without synergist | 50 | 92 | 96.7 | 32 |
| | | 37.5 | 59 | 84.7 | |
| | | 25 | 90 | 47.8 | |
| | | 10 | 90 | 3.3 | |
| | | 500 | 30 | 100 | |
| A | with synergist | 100 | 30 | 100 | |
| | | 25 | 90 | 100 | 13 |
| | | 20 | 90 | 92.2 | |
| | | 15 | 89 | 68.5 | |
| | | 10 | 120 | 24.2 | |
| | | 100 | 60 | 100 | |
| | | 50 | 60 | 100 | |
| | | 25 | 60 | 100 | |
| B | | 15 | 60 | 100 | 5.19 |
| | | 10 | 90 | 100 | |
| | | 7.5 | 60 | 93.3 | |
| | | 5 | 120 | 43.8 | |
| | | 1 | 90 | 4.0 | |
| | | 10 | | 83.3 | |
| C | without synergist | 7.5 | | 61 | 6.3 |
| | | 6.3 | | 5 | 37.1 |
| | | 2.5 | | 11 | |
| | with synergist | 7.5 | | 85.8 | |
| | | 5 | | 40.4 | 5.4 |
| | | 2.5 | | 6.7 | |
| | | 1 | | 5.6 | |
| DD | without synergist | 100 | | 93.3 | |
| | | 50 | | 85.0 | 24.0 |
| | | 25 | | 55.0 | |
| | | 10 | | 6.7 | |
| | | 100 | | 100 | |
| | with synergist | 50 | | 83.3 | 8.5 |
| | | 10 | | 53.2 | |
| | | 1 | | 20.0 | |
| F | without synergist | | | | 36.2 |
| | with synergist | | | | 26.3 |
| G | without synergist | | | | 2.7 |
| | with synergist | | | | 2.8 |
| J | without synergist | | | | 14.5 |
| K | without | | | | 12.8 |

TABLE II-continued

B. Lethal Activity against Houseflies

| Product | | Doses in ng per insect | Number of insects | % of mortality at 24 hours | $DL_{50}$ in ng per insects |
|---|---|---|---|---|---|
| | synergist | | | | |

TABLE III

C. Activity against Spodoptera Littoralis

| Product | | Doses in nanograms per insect | % of mortality after | | |
|---|---|---|---|---|---|
| | | | 24 h | 48 h | 6 days |
| A | with synergist | 200 | 100 | 100 | 100 |
| | | 20 | 100 | 96.1 | 96.1 |
| B | | 1000 | 100 | 100 | |
| | | 100 | 100 | 100 | |
| | | 10 | 70.0 | 100 | |
| C | | 100 | 100 | 100 | |
| | | 10 | 100 | 100 | |
| D | with synergist | 1000 | 100 | 100 | |
| | | 100 | 100 | 100 | |
| | | 50 | 80.0 | 80.0 | |
| E | with synergist | 1000 | 100 | 100 | |
| | | 100 | 60 | 60 | |
| F | without synergist | | | 37.6 | |

TABLE IV

D. Activity against Epilachna Varivestris

| Product | | $DL_{50}$ in nanograms |
|---|---|---|
| F | without synergist | 5.4 |
| G | without synergist | 4.5 |
| H | without synergist | 3.5 |
| I | without synergist | 4.77 |
| J | without synergist | 2.24 |
| K | without synergist | 2.16 |

TABLE V

E. Activity against *Sitophilus Granarius*

| Product | | Doses in nanograms per insect | % of mortality after 24 h | 48 h | 6 days |
|---|---|---|---|---|---|
| A | synergist | 200 | 100 | 100 | 100 |
| | | 20 | 100 | 96.1 | 96.1 |
| B | | 200 | 100 | 100 | 100 |
| | | 20 | 98.0 | 98.0 | 94.1 |

TABLE V'

| Product | Doses in mg/liter | mg per Kg wheat (ppm) | Efficacity after 7 days |
|---|---|---|---|
| C | 200 | 10 | 100 |
| | 20 | 1 | 100 |
| D | 200 | 10 | 100 |
| | 20 | 1 | 100 |
| E | 200 | 10 | 100 |
| | 20 | 1 | 98 |

TABLE VI

G. Activity against *Aphis Graccivora*

| Product | Doses in manograms per insect | % of mortality after 1 h | 2 h | 24 h | 48 hr |
|---|---|---|---|---|---|
| A | 20 | 100 | 100 | 100 | 100 |
| | 2 | 100 | 100 | 95.0 | 100 |
| | control | 0 | 0 | 0 | 0 |
| B | 20 | 80.0 | 75.0 | 100 | 100 |
| | 2 | 50.0 | 65.0 | 100 | 100 |
| C | 20 | 100 | 100 | 100 | 100 |
| | 2 | 15 | 35 | 100 | 100 |
| D with synergist | 20 | 70.0 | 90.0 | 100 | 100 |
| | 2 | 25.0 | 40.0 | 65.0 | 85.0 |

TABLE VII

H. Lethal Activity against *Aedes Aegypti*

| Product | Doses in mg/m² | % of mortality after 1 h | 24 h | DL$_{50}$ After 24 h |
|---|---|---|---|---|
| B | 10 | 100 | 100 | |
| | 5 | 100 | 100 | 0.75 |
| | 1 | 45 | 80 | |
| | 0.5 | 8.3 | 12.5 | |

TABLE VII'

I. Knockdown Activity against *Aedes Aegypti*

| Product | Doses in mg/m² | % knocked down insects after 2 mn | 4 mn | 6 mn | 8 mn |
|---|---|---|---|---|---|
| B | 83.3 | 0 | 31.9 | 76.5 | 100 |

TABLE VIII

E. Activity against *Tribulium Castaneum*

| Product | Doses in namograms per insect | % of mortality after 24 h | 48 h | 6 days |
|---|---|---|---|---|
| A with synergist | 200 | 100 | 100 | 100 |
| | 20 | 30.0 | 24.0 | 30.0 |
| B | 200 | 100 | 100 | 100 |
| | 20 | 86.0 | 80.0 | 82.0 |
| C | 200 | 10 | | 100 |

TABLE VIII-continued

E. Activity against *Tribulium Castaneum*

| Product | Doses in namograms per insect | % of mortality after 24 h | 48 h | 6 days |
|---|---|---|---|---|
| | 20 | 1 | | 100 |

TABLE VIII'

| Product | mg/liter | mg per Kg of wheat ppm | % efficacity after 7 days |
|---|---|---|---|
| D with synergist | 200 | 10 | 100 |
| | 20 | 1 | 100 |

TABLE IX

F. Activity against *Blatella Germanica*

| Product | Doses in nanograms per insect | % of mortality after | | |
|---|---|---|---|---|
| | | 24 h | 48 h | 8 days |
| D with synergist | 1000 | 100 | 100 | 100 |
| | 100 | 100 | 100 | 100 |
| | 50 | 100 | 90.0 | 80.0 |
| | | 24 h | 48 h | 6 days |
| E with synergist | 1000 | 100 | 100 | 100 |
| | 500 | 70 | 100 | 100 |

The said tests show that compounds A to L have a good insecticidal activity.

ACARICIDAL ACTIVITY

The acaricidal activity of compound M was studied with *Tetranychus Urticae* at 22° C.±1° C. at 50% relative humidity against bean plants. The tests were effected in 3 simultaneous series at doses of 5, 2.5 and 1.25 g/hl with each series being run twice using 50 acariens in each test. The percent of mortality after 24 hours on each leaf and percent of repulsion after 24 hours was determined. Certain compounds, of which compound M is one, have a repulsive effect against acariens which keep them from the plants. The test showed generally that acariens are repelled for 24 hours rapidly killing and is incorporated as a percent of the total efficacy.

TABLE X

| Product | Dose in g/hl | % mortality after 24 h Test 1 | Test 2 | Average | % repulsive after 24h Test 1 | Test 2 | Average | % Total efficacy after 24h |
|---|---|---|---|---|---|---|---|---|
| M | 5.0 | 60 | 26 | 43 | 40 | 60 | 50 | 93 |
| | 2.5 | 16 | 20 | 18 | 84 | 60 | 72 | 90 |
| | 1.25 | 16 | 0 | 8 | 84 | 70 | 77 | 85 |
| Control | — | — | — | — | — | — | — | 0 |

The results of Table X show that compound M has a good acaricidal activity.

Six simultaneous series of tests with bean plants were conducted with 50 acariens (*Tetranychus urticae*) per bean plant and per dose. Compound M was applied at doses of 10-5-2, 5-1, 25-0, 625-0 and 312 g/hl on plants in the open air and reading were taken 24, 48 and 72 hours after treatment to determine the number of live and dead acariens on the plant and off the plant (repulsive effect) and the results are reported in Table XI.

TABLE XI

| Doses in g/hl | % of Controls | | | | | | | | | | % total mortality at 72 h |
|---|---|---|---|---|---|---|---|---|---|---|---|
| | 24 h | | | | 48 h | | | | 72 h | | |
| | On Plant | | Off Plant | | On Plant | | Off Plant | | On Plant | | Off Plant | |
| | Live | Dead | L | D | L | D | L | D | L | D | L | D | |
| 10 | 30 | 70 | 0 | 0 | 0 | 92 | 8 | 0 | 0 | 92 | 0 | 8 | 100 |
| 5 | 46 | 44 | 10 | 0 | 0 | 90 | 10 | 0 | 0 | 90 | 0 | 10 | 100 |
| 2,5 | 50 | 30 | 20 | 0 | 22 | 58 | 4 | 16 | 0 | 80 | 0 | 20 | 100 |
| 1,25 | 40 | 0 | 60 | 0 | 40 | 0 | 12 | 48 | 0 | 40 | 0 | 60 | 100 |
| 0,625 | 40 | 0 | 60 | 0 | 40 | 0 | 6 | 54 | 40 | 0 | 0 | 60 | 60 |
| 0,312 | 100 | 0 | 0 | 0 | 86 | 14 | 0 | 0 | 78 | 22 | 0 | 0 | 22 |

The results of Table XI show that the open air tests on fields confirm the laboratory tests and the total activity of compound M appears to be greater out of the laboratory as the total percentage of dead is about equal to 100% at 2.5 g/l as compared to 85 in the laboratory. The mortality or repulsive effect is very long, even after 48 and 72 hours.

EXAMPLE A

An emulsifiable concentrate was prepared consisting of 1.25 g of (1S) 2-methyl-3-allyl-4-methylene-cyclopent-2-ene-1-yl (1R, trans) 2,2-dimethyl-3-(2,2-difluoro-ethenyl)-cyclopropane-carboxylate, 1 g of piperonyl butoxide, 0.25 g of Tween 80, 0.1 g of 2,4-dimethyl-6-tert.-butyl-phenol and 97.4 g of water.

EXAMPLE B

A fumigant composition was prepared from a homogenous composition consisting of 1.25 g of (1S) 2-methyl-3-allyl-4-methylene-cyclopent-2-ene-1-yl (1R, trans) 2,2-dimethyl-3-(2,2-difluoro-ethenyl)-cyclopropane-carboxylate, 25 g of powdered leaves of Macillus Thumbergii, 40 g of powdered cedar needles, 32.75 g of pine wood powder, 0.5 g of vert brillant and 0.5 g of p-nitrophenol.

EXAMPLE C

An emulsifiable concentrate was prepared as a homogenous mixture of 2 g of (1S) 2-methyl-3-allyl-4-methylene-cyclopent-2-ene-1-yl (1R, trans) 2,2-dimethyl-3-(2,2-dichloroethenyl)-cyclopropane-carboxylate, 20 g of Tween 80, 0.1 g of 2,4-dimethyl-6-tert.-butyl-phenol and 77.9 g of xylene.

EXAMPLE D

An ixodicide for veterinary use was prepared containing 4 g of (1S) 2-methyl-3-allyl-4-methylene-cyclopent-2-ene-1-yl (1R, trans) 2,2-dimethyl-3-(2,2-difluoro-ethenyl)-cyclopropane-carboxylic, 2.5 g of piperonyl butoxide, 10 g of Polysorbate 80, 25 g of Trifon X 100, 1 g of tocopherol acetate and 100 ml of ethanol.

Various modifications of the compounds and methods of the invention may be made without departing from the spirit or scope thereof and it is to be understood that the invention is intended to be limited only as defined in the appended claims.

We claim:

1. An ester of the formula

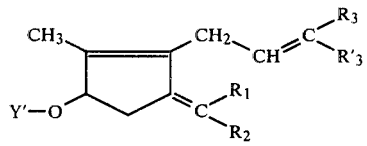

wherein $R_1$ and $R_2$ are individually selected from the group consisting of hydrogen, halogen, alkyl of 1 to 6 carbon atoms, phenyl, naphthyl, alkoxy-carbonyl of 2 to 5 carbon atoms and —CN, $R_3$ and $R_3'$ are individually selected from the group consisting of hydrogen, halogen, alkenyl of 2 to 3 carbon atoms and alkyl of 1 to 3 carbon atoms, $Y'$ is selected from the group consisting of

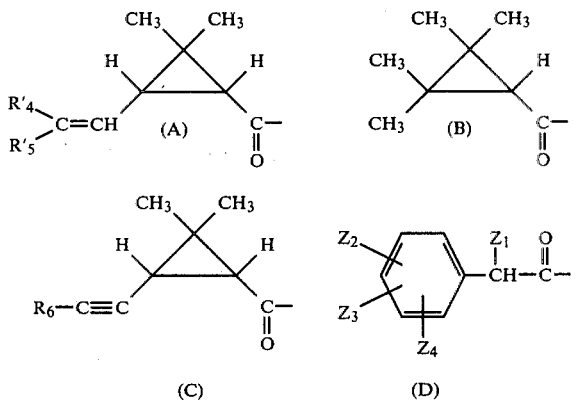

$R_4'$ and $R_5'$ are individually selected from the group consisting of hydrogen, alkyl of 1 to 4 carbon atoms, fluorine, bromine, chlorine or $R_4'$ and $R_5'$ together with the carbon atom to which they are attached form a hydrocarbon ring of 3 to 7 chain members or $R_4'$ is cyano and $R_5'$ is phenyl or $R_4'$ is hydrogen and $R_5'$ is selected from the group consisting of cyano,

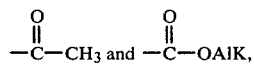

AlK is alkyl of 1 to 4 carbon atoms, the double bond in the 1-position of the vinyl side chain of formula (A) having (E) or (Z) configuration, $R_6$ is selected from the group consisting of hydrogen, alkyl of 1 to 4 carbon atoms and alkoxycarbonyl of 2 to 5 carbon atoms, the substituents on the cyclopropane ring of formula (A) and (C) have the cis or trans, racemic or optically active configuration, $Z_1$ is alkyl of 1 to 4 carbon atoms, $Z_2$, $Z_3$ and $Z_4$ are individually selected from the group consisting of hydrogen, alkyl of 1 to 4 carbon atoms, alkoxy of 1 to 4 carbon atoms, alkylthio of 1 to 4 carbon atoms and halogen and the asymetric carbon of formula (D) may be (S) or (R) configuration or a racemic mixture thereof and the carbon atom in the 1-position of the alcohol moiety may have (R), (S) or racemic configuration.

2. A compound of claim 1 of the formula

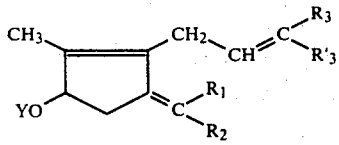

wherein $R_1$, $R_2$, $R_3$ and $R_3'$ have the definition of claim 1 and Y is selected from the group consisting of

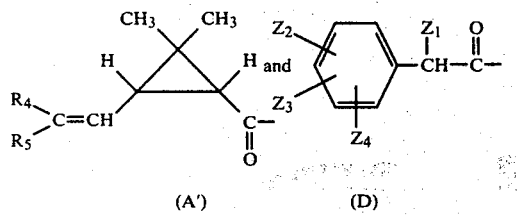

wherein $Z_1$, $Z_2$, $Z_3$ and $Z_4$ have the definitions of claim 1, $R_4$ and $R_5$ are individually selected from the group consisting of hydrogen, alkyl of 1 to 4 carbon atoms, fluorine, chlorine and bromine or $R_4$ is hydrogen and $R_5$ is selected from the group consisting of —CN,

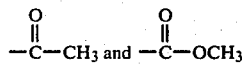

or $R_4$ and $R_5$ together with the carbon atom to which they are attached form a hydrocarbon ring of 3 to 7 ring members and the substituent of A' on the cyclopropane ring gives a cis or trans or racemic or optically active configuration and the double bond in the 1-position of the side chain may have (E) or (Z) configuration.

3. A compound of claim 2 wherein Y has the formula

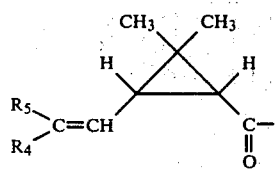

4. A compound of claim 2 wherein Y is

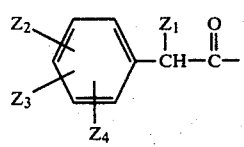

5. A compound of claim 3 wherein $R_1$, $R_2$, $R_4$ and $R_5$ are halogen and $R_3$ and $R_3'$ are hydrogen.

6. A compound of claim 3 wherein $R_1$, $R_2$, $R_3$ and $R_3'$ are hydrogen and $R_4$ and $R_5$ together with the carbon atom to which they are attached form a hydrocarbon ring.

7. A compound of claim 3 wherein $R_1$, $R_2$, $R_3$ and $R_3'$ are hydrogen and $R_4$ and $R_5$ are halogen.

8. A compound of claim 1 selected from the group consisting of (1S) 2-methyl-3-allyl-4-methylene-cyclopent-2-ene-1-yl (1R, trans) 2,2-dimethyl-3-cyclopentylidenemethyl-cyclopropane-1-carboxylate; (1S) 2-methyl-3-allyl-4-methylenecyclopent-2-ene-1-yl (1R, trans) 2,2-dimethyl-3-(2,2-difluoroethenyl)-cyclopropane-1-carboxylate; (1S) 2-methyl-3-allyl-4-methylene-cyclopent-2-ene-1-yl (1R, trans) 2,2-dimethyl-3-(2,2-dichloroethenyl)-cyclopropane-1-carboxylate; (1S) 2-methyl-3-allyl-4-methylene-cyclopent-2-ene-1-yl (1R, trans) 2,2-dimethyl-3-[2-(Z)-cyanoethenyl]-cyclopropane-1-carboxylate; (1S) 2-methyl-3-allyl-4-methylene-cyclopent-2-ene-1-yl (1R, trans) 2,2-dimethyl-3-(2-chloro-2-fluoro-ethenyl)-cyclopropane-1-carboxylate; (1S) 2-methyl-3-allyl-4-methylenecyclopent-2-ene-1-yl (1R, trans) 2,2-dimethyl-3-cyclobutylidenemethyl-cyclopropane-1-carboxylate and (1S) 2-methyl-3-allyl-4-methylene-cyclopent-2-ene-1-yl (1R, cis) 2,2-dimethyl-3-ethynyl-cyclopropane-1-carboxylate.

9. An insecticidal composition comprising an insecticidally effective amount of at least one compound of claim 1 and an inert carrier.

10. A composition of claim 9 wherein the active compound has the formula

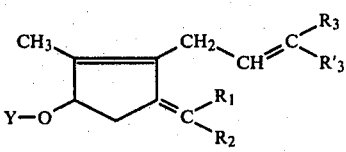

wherein $R_1$, $R_2$, $R_3$ and $R_3'$ have the definitions of claim 1 and Y is selected from the group consisting of

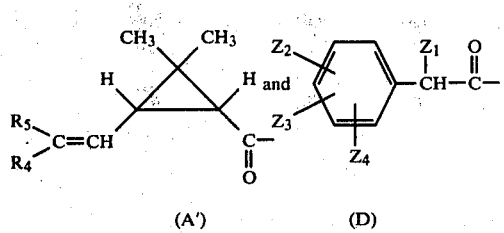

11. A composition of claim 10 wherein Y has the formula

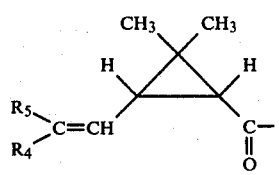

12. A composition of claim 10 wherein Y is

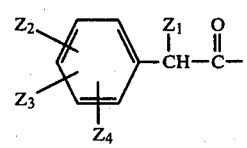

13. A composition of claim 11 wherein $R_1$, $R_2$, $R_4$ and $R_5$ are halogen and $R_3$ and $R_3'$ are hydrogen.

14. A composition of claim 11 wherein $R_1$, $R_2$, $R_3$ and $R_3'$ are hydrogen and $R_4$ and $R_5$ together with the carbon atom to which they are attached form a hydrocarbon ring.

15. A composition of claim 11 wherein $R_1$, $R_2$, $R_3$ and $R_3'$ are hydrogen and $R_4$ and $R_5$ are halogen.

16. Animal feed containing an acaricidally effective amount of at least one compound of claim 1.

17. A method of killing insects comprising contacting insects with an insecticidally effective amount of at least one compound of claim 1.

18. The method of claim 17 wherein the active compound has the formula

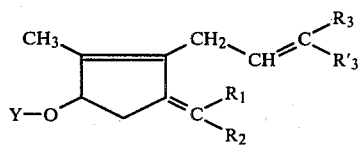

wherein $R_1$, $R_2$, $R_3$ and $R_3'$ have the definitions of claim 1 and Y is selected from the group consisting of

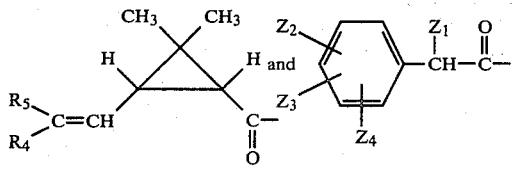

(A')  (D)

wherein $Z_1$, $Z_2$, $Z_3$ and $Z_4$ have the definitions of claim 1, $R_4$ and $R_5$ are individually selected from the group consisting of hydrogen, alkyl of 1 to 4 carbon atoms, fluorine, chlorine and bromine or $R_4$ is hydrogen and $R_5$ is selected from the group consisting of —CN,

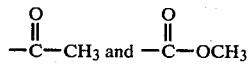

or $R_4$ and $R_5$ together with the carbon atom to which they are attached form a hydrocarbon ring of 3 to 7 ring members and the substituent of A' on the cyclopropane ring gives a cis or trans or racemic or optically active configuration and the double bond in the 1-position of the side chain may have (E) or (Z) configuration.

19. The method of claim 17 wherein the active compound has the formula

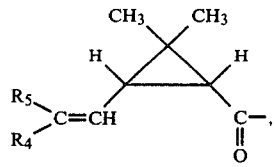

20. A method of claim 18 wherein Y is

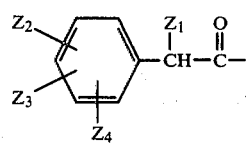

21. A method of claim 18 wherein $R_1$, $R_2$, $R_4$ and $R_5$ are halogen and $R_3$ and $R_3'$ are hydrogen.

22. A method of claim 19 wherein $R_1$, $R_2$, $R_3$ and $R_3'$ are hydrogen and $R_4$ and $R_5$ together with the carbon atom to which they are attached form a hydrocarbon ring.

23. A method of claim 19 wherein $R_1$, $R_2$, $R_3$ and $R_3'$ are hydrogen and $R_4$ and $R_5$ are halogen.

24. A method of combatting acariens comprising contacting acariens with an acaricidally effective amount of at least one compound of claim 1.

25. The method of claim 24 wherein the compound is applied to plants to be protected.

26. A method of combatting nematodes comprising contacting nematodes with nematocidally effective amount of at least one compound of claim 1.

27. A method of combatting fungi comprising contacting fungi with a fungicidally effective amount of at least one compound of claim 1.

28. A method of protecting animals against pests comprising administering to animals a pesticidally effective amount of least one compound of claim 1.

* * * * *

UNITED STATES PATENT AND TRADEMARK OFFICE
CERTIFICATE OF CORRECTION

PATENT NO. : 4,356,187
DATED : October 26, 1982                    Page 1 of 3
INVENTOR(S) : JACQUES MARTEL ET AL.

It is certified that error appears in the above-identified patent and that said Letters Patent is hereby corrected as shown below:

Column 4, line 38: "metal said" should read -- metal salt --.
Column 5, line 44; Column 13, line 31:
    "cyanoe-" should read -- cyano- --.
Column 5, line 45; Column 13, line 32; Column 15, line 30;
Column 26, line 18; Column 50, line 45:
    "thenyl" should read -- ethenyl --.
Column 6, line 5: "butoxye-" should read -- butoxy- --.
Column 6, line 6: "thoxy" should read -- ethoxy --.
Column 7, line 37: "tetrahydroph-" should be -- tetrahydro- --.
Column 7, line 38: "thalimidomethanol" should read
    -- phthalimidomethanol --.
Column 8, line 35: "1-S-hydroxy" should be -- 1S-hydroxy --.
Column 12, line 37: "-CH-" should read -- $-CH_2-$ --.
Column 12, line 38: Delete "$_2-$", first occurrence.
Column 12, second line from bottom: "-61.5° ± .15°" should
    read -- -61.5° ± 1.5° --.
Column 13, line 40: Delete "CN"
                                                                                                           CN
Column 13, line 41: (>CH = CH)" should read -- ( CH = CH)
Column 13, line 44; Column 15, line 4; Column 26, line 38:
    "$CH_2$ = C<" should read -- $CH_2$ = C
Column 15, line 9: "dichloroethyl" should read
    -- dichloroethenyl --.

UNITED STATES PATENT AND TRADEMARK OFFICE
CERTIFICATE OF CORRECTION

PATENT NO. : 4,356,187

DATED : October 26, 1982

INVENTOR(S) : JACQUES MARTEL ET AL.

It is certified that error appears in the above-identified patent and that said Letters Patent is hereby corrected as shown below:

Column 15, line 29: "dichloroe-" should read -- dichloro- --.

Column 22, line 39: "±2.2°" should read -- ± 2.5° --.

Column 26, line 17; Column 50, line 44: "difluoroe-" should read -- difluoro- --.

Column 28, line 52: "2 $^o/_{oo}$" should read -- 1$^o/_{oo}$ --.

Column 30, line 35: "63.3 g" should read -- 65.3 g --.

Column 30, line 38; Column 31, line 3; Column 44, line 21: "methox-" should read -- methoxy- --.

Column 30, line 39; Column 31, line 4; Column 44, line 22: "ycarbonyl" should read -- carbonyl --.

Column 31, line 32: "dihydrox-" should read -- dihydroxy- --.

Column 31, line 33: "ymethyl" should read -- methyl --.

Column 44, line 8: After "..trans)", delete "of".

Column 49, lines 48-51: Correct this paragraph to read:

-- The test carried out is a test by film on glass. 1.54 cm$^3$ of an acetone solution at 10 mg/l of the product to be tested, is deposited in Petri boxes of 154 cm$^2$, then the acetone is allowed to evaporate; the film corresponds to 0.1 mg of active material per m$^2$. --

Column 51, Table II, the values for "C without synergist"
which read " 6.3   5   37.1"
should be deleted
and replaced by   --   5   37.1 --

UNITED STATES PATENT AND TRADEMARK OFFICE
CERTIFICATE OF CORRECTION

PATENT NO. : 4,356,187

DATED : October 26, 1982

INVENTOR(S) : JACQUES MARTEL ET AL.

It is certified that error appears in the above-identified patent and that said Letters Patent is hereby corrected as shown below:

Column 55, line 59: "carboxylic" should read -- carboxylate --.

Signed and Sealed this

Tenth Day of May 1983

[SEAL]

Attest:

GERALD J. MOSSINGHOFF

Attesting Officer

Commissioner of Patents and Trademarks